(12) United States Patent
Aldridge et al.

(10) Patent No.: US 9,023,652 B2
(45) Date of Patent: May 5, 2015

(54) ORGANOMETALLIC SENSOR DEVICE

(75) Inventors: Simon Aldridge, Oxford (GB); Ian A. Fallis, Cardiff (GB)

(73) Assignee: University College Cardiff Consultants Ltd., Cardiff South Wales (GB)

( * ) Notice: Subject to any disclaimer, the term of this patent is extended or adjusted under 35 U.S.C. 154(b) by 648 days.

(21) Appl. No.: 12/448,415

(22) PCT Filed: Dec. 21, 2007

(86) PCT No.: PCT/GB2007/004938
§ 371 (c)(1),
(2), (4) Date: Oct. 7, 2009

(87) PCT Pub. No.: WO2008/078092
PCT Pub. Date: Jul. 3, 2008

(65) Prior Publication Data
US 2010/0285602 A1    Nov. 11, 2010

(30) Foreign Application Priority Data
Dec. 22, 2006 (GB) .................................. 0625789.3

(51) Int. Cl.
*G01N 31/22* (2006.01)
*G01N 27/333* (2006.01)
(Continued)

(52) U.S. Cl.
CPC ........ *G01N 27/3335* (2013.01); *G01N 33/0049* (2013.01); *G01N 33/0057* (2013.01); *C07F 17/02* (2013.01); *C09B 57/00* (2013.01)

(58) Field of Classification Search
None
See application file for complete search history.

(56) References Cited

U.S. PATENT DOCUMENTS 4,629,697 A * 12/1986 Limbach et al. ................. 435/26
5,334,513 A *  8/1994 Skold et al. .................... 435/7.92
2004/0058194 A1 *  3/2004 Stossel et al. ................... 428/690

FOREIGN PATENT DOCUMENTS

JP         A-9-178724       7/1997

OTHER PUBLICATIONS

Bresner, C. et al. "Selective Electrochemical Detection of Hydrogen Fluoride by Ambiphilic Ferrocene Derivatives," Angew. Chem. Int. Ed. 2005, 44, 3606-3609.*

(Continued)

*Primary Examiner* — Yelena G Gakh
*Assistant Examiner* — Michelle Adams
(74) *Attorney, Agent, or Firm* — Oliff PLC

(57) ABSTRACT

The present invention relates to detectors for detecting fluorine-containing compounds and/or cyanide containing compounds, including hydrogen fluoride (HF) or HCN gas, hydrofluoric acid in solution, selected chemical warfare agents, selected industrial chemicals which may be hydrolyzed to release HF or HCN gas, compounds containing a cyanide group, and compounds that can release HF or HCN. The detectors comprise i) an organometallic component containing at least one bis-substituted boryl group of the formula —B($R^B$)($R^{B'}$) wherein each $R^B$ and each $R^{B'}$ is independently selected from H, halogen, $C_{1-6}$ alkyl, $OR^6$, $N(R^6)(R^7)$, $SR^6$, $C_{3-20}$ aryl or heteroaryl, and $C_{3-20}$ cycloalkyl or heterocloalkyl groups, each of which may be optionally substituted, ii) a Lewis base component, and iii) a solid matrix component. The invention also relates to novel organometallic compounds containing at least one bis-substituted boryl group and their use in detectors for fluorine containing compounds and/or cyanide containing compounds.

18 Claims, 19 Drawing Sheets

(51) Int. Cl.
  *G01N 33/00* (2006.01)
  *C07F 17/02* (2006.01)
  *C09B 57/00* (2006.01)
  *G01N 21/62* (2006.01)

(56) References Cited

OTHER PUBLICATIONS

Shiratori, H. et al. "Change of electron-transfer path-selectivity in a triad by F-coordination at a boronate-ester bridge," Chem. Commun., 1999, 2181-2182.*

Melaimi, M. et al. "A Heteronuclear Bidentate Lewis Acid as a Phosphorescent Fluoride Sensor," J. Am. Chem. Soc. 2005, 127, 9680-9681.*

Dusemund, C. et al. "Selective Fluoride Recognition with Ferroceneboronic Acid," J. Chem. Soc., Chem. Commun., 1995, 333-334.*

Yamaguchi, S. et al. "Colorimetric Fluoride Ion Sensing by Boron-Containing p-Electron Systems," J. Am. Chem. Soc. 2001, 123, 11372-11375.*

Heilmann, J. B. et al. "A Synthetic Route to Borylene-Bridged Poly(ferrocenylene)s," Angew. Chem. Int. Ed. 2006, 45, 920-925, published online Dec. 30, 2005.*

Broomsgrove, A. E. J. et al. "AND/NOT Sensing of Fluoride and Cyanide Ions by Ferrocene-Derivatised Lewis Acids" Chem. Eur. J. 2008, 4, 7525-7529.*

Broomsgrove, A. E. J. et al. "Evaluation of Electronics, Electrostatics and Hydrogen Bond Cooperativity in the Binding of Cyanide and Fluoride by Lewis Acidic Ferrocenylboranes," Inorg. Chem., 2010, 49 (1), pp. 157-173.*

Arimori et al., "Synthesis and structural characterisation of the first bis(bora)calixarene: a selective, bidentate, fluorescent fluoride sensor," Chem. Commun., Jun. 2004, p. 1640-1641, XP-002473973.

Aldridge et al., "Multidentate Lewis acids: synthesis, structure and mode of action of a redox-based fluoride ion sensor," Chem Comm, Mar. 2002, p. 740-741, XP-002473972.

Badugu et al., "Cyanide-sensitive fluorescent probes," Dyes and Pigments, 2005, p. 49-55, XP-004524130.

Cooper et al., "Selective Fluorescence detection of fluoride using boronic acids," Chem. Commun., 1998, XP-001037341.

Bresner et al., "Fluoride anion binding by cyclic boronic esters: influence of backbone chelate on receptor integrity," Dalton Transactions 2006, p. 3660-3667, XP-002473974.

Norrild et al., "Crystal structures of 2-(N,N-dimethylaminoalkyl)ferroceneboronic acids and their diol derivatives. The quest for a B-N intramolecular bond in the solid state," J. Chem. Soc. Perkin Trans, 2001, p. 727-732, XP-002473971.

Yamamoto et al., "Visual sensing of fluoride ion and saccharides utilizing a coupled redox reaction of ferrocenylboronic acids and dye molecules," Chem. Commun. 3, 1996, p. 407-408, XP-009097586.

Nicolas et al., "Electrochemical sensing of fluoride and sugars with a boronic acid-substituted bipyridine Fe(II) complex in solution and attached onto an electrode surface," Electrochimica Acta, 2001, p. 1179-1190, XP-002473970.

Ahlers et al., "Molecular Recognition of Cyanide by a Dicopper(II) Macrocyclic Ionophore: Construction of a Cyanide-Selective Liquid-Membrane Electrode," Agnew. Chem. Int. Ed. Eng 35, 1996, p. 2141-2143.

Hudnall et al., "Ammonium Boranes for the Selective Complexation of Cyanide or Fluoride Ions in Water," J. American Chemical Society, Sep. 2007, p. 11978-11986.

Badugu et al., "Enhanced Fluorescence Cyanide Detection at Physiologically Lethal Levels: Reduced ICT-Based Signal Transduction," J. American Chemical Society, 2005, p. 3635-3641.

* cited by examiner

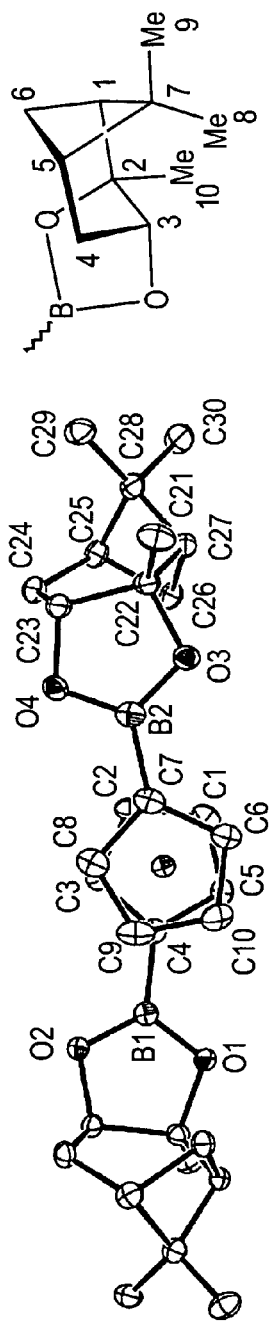
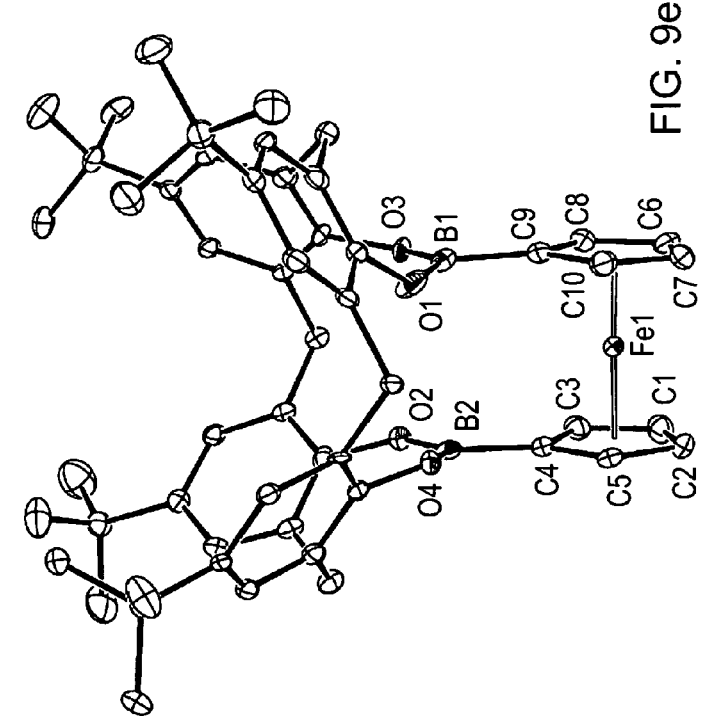
FIG. 9d
FIG. 9e

ORGANOMETALLIC SENSOR DEVICE

TECHNICAL FIELD

The present proposals relate to detectors for fluorine-containing compounds, including hydrogen fluoride (HF) gas, hydrofluoric acid in solution, selected chemical warfare agents, and selected industrial chemicals which may be hydrolysed to release HF gas. The proposals also relate to detectors for cyanide-containing compounds, including hydrogen cyanide (HCN) gas, hydrocyanic acid in solution, selected chemical warfare agents, and selected industrial chemicals which may be hydrolysed to release HCN gas. Furthermore, the proposals relate to novel organometallic compounds and their use in detectors for fluorine containing compounds, compounds containing a cyanide group, and compounds that can release HF or HCN.

BACKGROUND

HF is an extremely toxic and corrosive substance that is manufactured on a large scale for a range of industrial chemical processes. For example, HF is used extensively in the nuclear fuels industry for the hydro fluorination of uranium dioxide ($UO_2$) to afford uranium tetrafluoride, required as a pre-enrichment feedstock for $UF_6$ production. Acid fluorides are used on a small scale in chemical research and fine chemical products and are also constituents of some chemical weapons agents (CWAs), for example the military acetylcholine esterase inhibitors (nerve agents) Sarin (GB, methylphosphonofluoridic acid 1-methylethylester), Soman (GD, methylphosphonofluoridic, 1,2,2-trimethylpropyl ester) and cyclohexylsarin (GF, methylphosphonofluoridic, cyclohexylester). Sarin is fatal in minute doses (0.01 mg of Sarin and per kg of body weight), is readily manufactured from basic starting materials with minimal apparatus and knowledge, and thus represent a credible terrorist threat. For example, 19 fatalities were caused by terrorist Sarin gas attacks on the Tokyo underground in 1994 and 1995.

In addition, some toxic industrial chemicals (TICs) contain fluorine atoms and can liberate HF or fluoride ions, for example in solution or in the gas phase.

Furthermore compounds which contain the cyanide ion tend to have the potential to release toxic hydrogen cyanide (HCN) under appropriate conditions. For example, the chemical warfare nerve agent Tabun (GA) releases HCN on hydrolysis under appropriate pH conditions.

Therefore, the detection of both fluoride and cyanide ions is thought to be important in environmental and industrial monitoring and for security and military purposes to detect certain chemical warfare agents.

Existing technology used, for example by UK armed forces and airport security systems, to detect noxious airborne agents, such as HF or HCN, is based upon ion mobility spectrometry, in which the diffusion of airborne contaminants is measured after ionisation with a radioactive source (usually $^{63}Ni$). Current devices may be portable IMS (ion mobility spectroscopy) devices including the man-portable chemical agent detector (MCAD), the lightweight chemical agent detector (LCAD) and the handheld chemical agent monitor (CAM (RTM)), all of which are manufactured by Smiths Detection. These devices are effective in detecting low levels of airborne agents, such as HF or HCN, but are susceptible to false positives and, due to the sophisticated nature of the technology involved, are fragile, and hence costly due to the persistent need to replace components. Furthermore, this fragility means that these devices cannot readily be used in situations in which they would be required to withstand rough handling (e.g. many military operations). Thus there is a need for simple robust technology to categorically identify these dangerous agents.

It is important to note that there are no innocuous vaporous sources of fluoride or cyanide and thus the ability to detect such materials is of industrial, civilian and military importance. Furthermore, because ambient levels of hydrogen fluoride and hydrogen cyanide are negligible, any detection of gaseous hydrogen fluoride, hydrogen cyanide or an airborne material that may release or be hydrolysed to hydrogen fluoride or hydrogen cyanide gas or the fluoride or cyanide anion ($F^-$ or $CN^-$) can lead to a definitive identification of the presence of one of these dangerous agents.

Organometallic compounds that selectively bind fluoride ions in gaseous or aqueous form are known. For example, organometallic compounds based on ferrocene boronic esters have been shown to selectively bind fluoride anions with a change in the redox properties of the compound on fluoride binding [e.g., "Fluoride anion binding by cyclic boronic esters: influence of backbone chelate on receptor integrity", C. Bresner et al., *Dalton Trans.*, 2006, 3660-3667; "Multidentate Lewis acids: synthesis, structure and mode of action of a redox-based fluoride ion sensor", S. Aldridge et al., *Chem. Commun.*, 2002, 740-741; "Selective Electrochemical Detection of Hydrogen Fluoride by Ambiphilic Ferrocene Derivatives", C. Bresner et al., Angew. Chem. Int. Ed. 2005, 44, 3606-3609; "Hydrogen-bonding motifs in the solid-state structure of ferroceneboronic acid", C. Bresner et al., Acta Cryst. (2004). E60, m441-m443].

In addition a number of systems containing either an array of hydrogen-bond donors or appropriately spaced transition metal centres are known to be usable for detection of cyanide (Ahlers et al., Angew. Chem. Int. Ed. Eng. 1996, 35, 2141-2143) and the binding of cyanide by three-coordinate boranes is also known (R. Badugu et al. J. Am. Chem. Soc., 2005, 127, 3635-3641), even offering the possibility for sequestering cyanide from aqueous solution. Furthermore, the groups of both Jäkle and Gabbai have demonstrated the use of Lewis acid receptors containing the $BMes_2$ ($Mes=2,4,6-Me_3C_6H_2$) function to detect cyanide, in one case offering selective detection in the presence of fluoride in aqueous solution (T. W. Hudnall and F. P. Gabbai, *J. Am. Chem. Soc.*, 2007, 129, 11978-11986).

SUMMARY

The present application provides a detector and a method for detecting fluorine-containing compounds. The detector and detection method are both based on a mixture or collection of components or a series of independent steps which produce a detectable response, for example a colorimetric, electrochemical or fluorescence response, when exposed to a source of fluorine atoms, e.g., hydrogen fluoride, hydrofluoric acid, or a fluorine containing CWA/TIC or precursor thereof. A preferred aspect of the proposed detector and method is the ability to detect hydrogen fluoride from air within a solid-state chemical formulation.

These proposals also provide a detector and a method for detecting cyanide-containing compounds. The detector and detection method are both based on a mixture or collection of components or a series of independent steps which produce a detectable response, for example a colorimetric, electrochemical or fluorescence response, when exposed to a source of cyanide atoms, e.g., hydrogen cyanide, hydrocyanic acid, or a cyanide-containing CWA/TIC or precursor thereof. A preferred aspect of the proposed detector and method is the ability to detect hydrogen cyanide from air within a solid-state chemical formulation.

TICs which may be detectable by the fluoride detector and methods described in the present proposals include (but are not limited to) chemicals which either give rise to HF on hydrolysis or are direct sources of HF, including hydrogen fluoride gas, hydrofluoric acid, acetyl fluorides, sulfur tetrafluoride, diethylamino sulfur trifluoride, cyanogen fluoride, and fluoropyridinium salts.

Similarly, TICs which may be detectable by the cyanide detector and methods described include (but are not limited to) chemicals that give rise to HCN on hydrolysis or are direct sources of HCN or the cyanide anion ($CN^-$).

CWAs which may be detectable by the fluoride detector and methods described in the present proposals include (but are not limited to) compounds listed in Schedules 1-3 of the Chemical Weapons Convention (and their commonly used simulants) which give rise to HF on hydrolysis, including military acetyl-choline esterase inhibitors (nerve agents) such as Sarin (GB, methylphosphonofluoridic acid 1-methylethylester), cyclohexylsarin (GF, methylphosphonofluoridic, cyclohexylester), Soman (GD, methylphosphonofluoridic, 1,2,2-trimethylpropyl ester), and DFPs (dialkyl fluorophosphates) such as diisopropyl fluorophosphate, and other fluorine-containing CWAs. Also included are precursors to CWAs such as alkyl (e.g., Me, Et, n-Pr or i-Pr) phosphonyldifluorides (such as DF: Methylphosphonyldifluoride).

CWAs detectable by the cyanide detector and methods described herein include (but are not limited to) chemical weapons compounds which give rise to HCN on hydrolysis, including Tabun (GA).

The present proposals provide a fluoride detector comprising an organometallic compound substituted with at least one bis-substituted boryl substituent, wherein in the presence of a fluorine-containing compound, the boron centre of the bis-substituted boryl group forms a bond to a fluorine atom from the fluorine-containing compound, said bonding resulting in a detectable change in the organometallic compound.

The present proposals also provide a method comprising exposing to a test environment an organometallic compound substituted with at least one bis-substituted boryl substituent, detecting a change or lack of a change in the organometallic compound, and relating the change or lack of a change to the presence or absence of a fluorine-containing compound in the test environment.

These proposals also provide a cyanide detector comprising an organometallic compound substituted with at least one bis-substituted boryl substituent, wherein in the presence of a cyanide-containing compound, the boron centre of the bis-substituted boryl group forms a bond to a cyanide atom from the cyanide-containing compound, said bonding resulting in a detectable change in the organometallic compound.

Hence these proposals include a detector for detecting an analyte compound which is a fluorine-containing compound or a cyanide-containing compound, said detector comprising:

i) an organometallic compound having at least one bis-substituted boryl group of the formula $—B(R^B)(R^{B'})$, wherein each $R^B$ and each $R^{B'}$ is independently selected from H, halogen, $C_{1-6}$ alkyl, $OR^X$, $N(R^X)(R^Y)$, $SR^X$, $C_{3-20}$ aryl or heteroaryl, and $C_{3-20}$ cycloalkyl or heterocycloalkyl groups, each of which may be optionally substituted, wherein each $R^X$ and $R^Y$ group is selected from H, $C_{1-6}$ alkyl, $C_{3-20}$ cycloalkyl, and $C_{5-20}$ aryl, each of which may be optionally substituted, or is linked to another $R^X$ or $R^Y$ group;

ii) a Lewis base; and iii) a solid matrix component;

wherein in the presence of a fluorine-containing compound, the organometallic compound i) forms a complex with one or more fluorine atoms from the fluorine-containing compound to produce a detectable change; and/or in the presence of a cyanide-containing compound, the organometallic compound i) forms a complex with one or more cyanide groups from the cyanide-containing compound to produce a detectable change.

For example, the organometallic compound may be a compound according to formula A

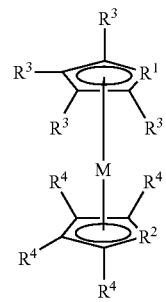

Formula A wherein:

the one or more $—B(R^B)(R^{B'})$ groups are either $—B(R^5)(R^{5'})$ or $—B(R^8)(R^{8'})$;

M is a metal atom selected from Fe, Ru, Os, Co, Cr, and Ni;

each $R^1$ is independently $—C(R^3)—$ or $—C(R^3)—C(R^3)—$;

each $R^2$ is independently $—C(R^4)—$ or $—C(R^4)—C(R^4)—$;

each $R^3$ is independently selected from H, $C_{1-6}$ alkyl, $C_{1-6}$ alkoxy, and $—B(R^5)(R^{5'})$;

each $R^5$ and each $R^{5'}$ is independently selected from H, halogen, $C_{1-6}$ alkyl, $OR^6$, $N(R^6)(R^7)$, $SR^6$, $C_{3-20}$ aryl or heteroaryl, and $C_{3-20}$ cycloalkyl or heterocycloalkyl groups, each of which may be optionally substituted;

each $R^4$ is independently selected from H, $C_{1-6}$ alkyl, $C_{1-6}$ alkoxy, and $—B(R^8)(R^{8'})$;

each $R^8$ and each $R^{8'}$ is independently selected from H, halogen, $OR^9$, $N(R^9)(R^{10})$, $SR^6$, $C_{3-20}$ aryl or heteroaryl, and $C_{3-20}$ cycloalkyl or heterocycloalkyl groups, each of which may be optionally substituted;

$R^6$, $R^{6'}$, $R^7$, $R^{7'}$, $R^9$, $R^{9'}$, $R^{10}$, and $R_{10'}$ are each independently selected from H, $C_{1-6}$ alkyl, $C_{3-20}$ cycloalkyl, and $C_{5-20}$ aryl, each of which may be optionally substituted; or one or more of $R^6$, $R^{6'}$, $R^9$, and $R^{9'}$ is independently linked to one or more other $R^6$, $R^{6'}$, $R^9$, or $R^{9'}$ groups; or one $R^6$ and one $R^{6'}$ group on one compound of formula A link to one $R^6$ and one $R^{6'}$ groups on a second independently defined compound of formula A to form a dimer, wherein the linkage between the two independent compounds of formula A is selected from

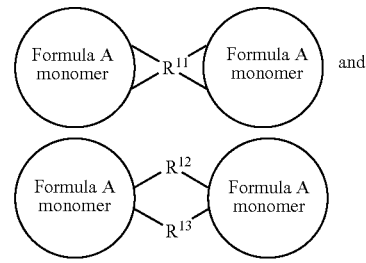

in which

R$^{11}$ is selected from a C$_{5-20}$ tetradentate aromatic group, C$_{8-32}$ tetradentate cycloalkane, and tetradentate group having the formula

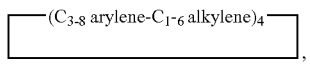

each of which may be optionally substituted, and

R$^{12}$ and R$^{13}$ are each independently selected from C$_{1-6}$ alkylene, C$_{3-20}$ cycloalkylene, C$_{3-20}$ arylene, C$_{1-6}$ heteroalkylene, C$_{3-20}$ heterocycloalkylene, and C$_{3-20}$ heteroarylene each of which may be optionally substituted.

Furthermore, the present proposals provide a method of sample analysis comprising the steps of:

a) exposing a detector according to any one of the preceding claims to a sample which may or may not contain a fluorine-containing compound and/or a cyanide-containing compound;

b) identifying the presence or absence of the detectable change in the detector;

c) correlating the presence or absence of the detectable change in the detector with the presence or absence of a fluorine-containing compound and/or a cyanide containing compound; and d) providing an output to indicate the presence or absence of a fluorine-containing compound and/or a cyanide containing compound.

For example, to detect cyanide-containing compounds, this may be a method comprising exposing to a test environment an organometallic compound substituted with at least one bis-substituted boryl substituent, detecting a change or lack of a change in the organometallic compound, and relating the change or lack of a change to the presence or absence of a cyanide-containing compound in the test environment.

In addition, the present proposals include novel organometallic compounds, which may be useful in detectors and methods described herein.

BRIEF DESCRIPTION OF FIGURES

FIG. 8a—Crystal structure of compound 1$^s$
FIG. 8b—Crystal structure of compound 1$^c$
FIG. 8c—Crystal structure of compound 1$^{pin}$
FIG. 8d—Crystal structure of compound 1$^e$
FIG. 8e—Crystal structure of compound 1$^{pr}$
FIG. 8f—Crystal structure of compound 1$^{pip}$
FIG. 8g—Crystal structure of compound 1$^m$
FIG. 8h—Crystal structure of compound 1$^{bn}$ FIG. 9a-e show the crystal structures of various organometallic compounds useful in the described detectors. In each case hydrogen atoms have been omitted for clarity and ORTEP ellipsoids set at the 50% probability level.

FIG. 9a—Crystal structure of compound 2$^s$
FIG. 9b—Crystal structure of compound 2$^s$.2(C$_6$H$_6$)
FIG. 9c—Crystal structure of compound 2$^e$
FIG. 9d—Crystal structure of compound 2$^{pin}$
FIG. 9e—Crystal structure of compound 2$^{ca}$

FIG. 11a—Crystal structure of compound 4$^s$
FIG. 11b—Crystal structure of compound 4$^{pin}$
FIG. 11c—Crystal structure of compound 4$^e$

FIG. 12a—Crystal structure of compound 5$^{ca}$
FIG. 12b—Crystal structure of compound 5$^{co}$

FIG. 17a 6b with F$^-$;
FIG. 17b 6b with CN$^-$;
FIG. 17c 1$^s$* with F$^-$;
FIG. 17d 1$^s$* with CN$^-$.

DETAILED DESCRIPTION

Fluoride Detectors

Figure 1:
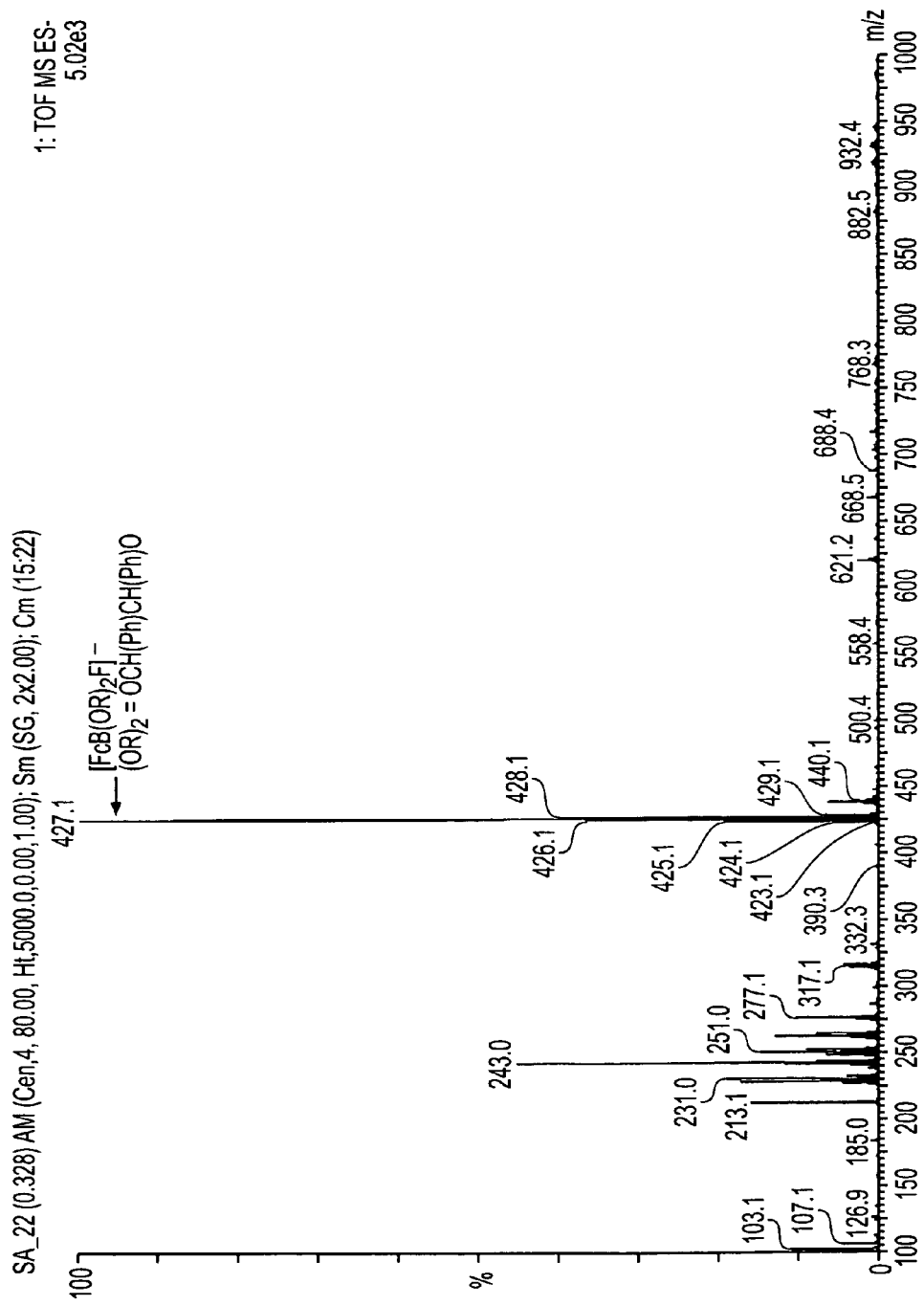
FIG. 1 shows a negative ion mass spectrograph of the [1$^{so}$F.]$^-$ ion.

In one aspect, the fluoride detector according to the present proposals comprises an indicator component which provides a sensory output initiated by the detectable change in the organometallic compound on exposure to the fluorine-containing compound. For example, the detectable change in the organometallic compound may be an electrochemical change which may initiate a colour change in the indicator component. Preferably, where the detector does not include an indicator component, the detectable change in the organometallic compound may itself be a sensory output (e.g., a colour change).

Preferably, the indicator component provides an audible, or visible (i.e. optical) output initiated by the detectable change in the organometallic compound on exposure to the fluorine-containing compound.

Preferably, the fluoride detector comprises a chemical amplifying system that amplifies the detectable change in the organometallic compound by using a chemical reaction. In one preferred embodiment, the chemical amplifying system comprises a chemical reaction (known as an orthogonal reaction) which is promoted or catalysed by the complex between the organometallic compound and at least one fluorine atom. This means that when even only a small number of fluorine atoms are bound by the boron centre of the organometallic compound, the resultant complex acts as a catalyst for the orthogonal reaction, which forms a part of the chemical amplifying system, and produces a large amount of the product of the orthogonal reaction. In one embodiment, the product of the orthogonal reaction acts as the indicator component (for example, the product may have a particularly distinctive colour that is easily visible when it is produced). Preferably, the product of the orthogonal reaction acts on the indicator component causing it to produce a sensory output.

The organometallic compound may be a compound having a metal atom coordinated by n-electrons from at least one cyclic ligand.

In one embodiment, the organometallic compound is a sandwich compound having a metal atom coordinated by n-electrons from exactly two cyclic ligands or a half-sandwich compound having a metal atom coordinated by n-electrons from exactly one cyclic ligand.

Preferably, the cyclic ligand(s) comprise a ring system containing 3-20 atoms, preferably 5-12 atoms, preferably 5-8 atoms, preferably 5 or 6 atoms, and most preferably 5 atoms.

Preferably, the cyclic ligand(s) are optionally substituted cyclopentadienyl ligands.

In preferred embodiments, one or both of the two substituents on the bis-substituted boryl substituent of the organometallic compound are independently selected from an ether group (—OR), an amino group (—NRR'), a sulphide group (—SR), an ester group (—C(=O)OR), and an amide group (—C(=O)NRR'). In one preferred aspect, both of the substituents on the bis-substituted boryl substituent are the same. Preferably, the bis-substituted boryl substituent is a diether boryl substituent or a diester boryl substituent.

Preferably, the bis-substituted boryl substituent on the organometallic compound is a cyclic diether boryl substituent (i.e. a boronic ester), e.g. having the formula

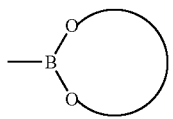

Preferably, the organometallic compound comprises a transition metal atom.

Preferably, the organometallic compound contains exactly one transition metal atom.

Preferably, the organometallic compound comprises a metal atom selected from Fe, Ru, Os, Co, Cr, Ni, and preferably Fe.

In preferred embodiments, the organometallic compound comprises a sandwich compound (i.e. one having a metal centre and two ring ligands) having a metal centre selected from Fe, Ru, Os, Co, Cr, and Ni, with one or two cyclopentadienyl or arene ligands or with two different arene ligands.

In one embodiment, the organometallic compound comprises a half-sandwich compound (i.e. one having a metal centre and only one ring ligand) having a metal centre selected from Fe, Ru, Os, Co, Cr, and Ni, with one cyclopentadienyl or arene ligands.

Preferably, the organometallic compound comprises a core selected from:

(sandwich compounds) $Fe(C_5\ ring)_2$, $Fe(C_6\ ring)_2$, $Ru(C_5\ ring)_2$, $Ru(C_6\ ring)_2$, $Co(C_6\ ring)_2$, $Co(C_6\ ring)_2$, $Cr(C_5\ ring)_2$, $Cr(C_6\ ring)_2$, $Ni(C_5\ ring)_2$, $Ni(C_6\ ring)_2$, $Fe(C_5\ ring)(C_6\ ring)$, $Ru(C_5\ ring)(C_6\ ring)$, $Os(C_5\ ring)(C_6\ ring)$, $Cr(C_5\ ring)(C_6\ ring)$, $Ni(C_5\ ring)(C_6\ ring)$;

(half-sandwich compounds) $Fe(C_5\ ring)$, $Fe(C_6\ ring)$, $Ru(C_5\ ring)$, $Ru(C_6\ ring)$, $Os(C_5\ ring)$, $Os(C_6\ ring)$, $Cr(C_5\ ring)$, $Cr(C_6\ ring)$, $Ni(C_5\ ring)$, $Ni(C_6\ ring)$.

Preferably, the detector according to the present proposals comprises:

i) either an organometallic compound comprising a unit according to formula I'

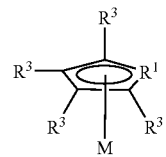

Formula I' or an organometallic compound according to formula I

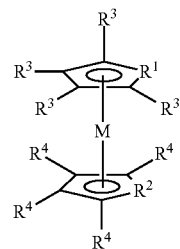

Formula I wherein:

M is a metal atom selected from Fe, Ru, Os, Co, Cr, and Ni, preferably Fe.

Each $R^1$ is independently —$C(R^3)$— or —$C(R^3)$—$C(R^3)$—;

Each $R^2$ is independently —$C(R^4)$— or —$C(R^4)$—$C(R^4)$—;

Each $R^3$ is independently selected from H, $C_{1-6}$ alkyl, $C_{1-6}$ alkoxy, and —$B(R^5)(R^{5'})$;

Each $R^5$ is independently selected from H, halogen, $C_{1-6}$ alkyl, $OR^5$, $N(R^5)(R^7)$, and $SR^6$;

Each $R^{5'}$ is independently selected from H, halogen, $C_{1-6}$ alkyl, $OR^{6'}$, $N(R^{6'})(R^{7'})$, and $SR^{6'}$)

Each $R^4$ is independently selected from H, $C_{1-6}$ alkyl, $C_{1-6}$ alkoxy, and —$B(R^8)(R^{8'})$;

Each $R^8$ is independently selected from H, halogen, $OR^9$, $N(R_9)(R^{10})$, and $SR^9$;

Each $R^{8'}$ is independently selected from H, halogen, $OR^{9'}$, $N(R^{9'})(R^{10'})$, and $SR^{9'}$;

$R^7$, $R^{7'}$, $R^{10}$, and $R^{10'}$ are each independently selected from H, $C_{1-6}$ alkyl, $C_{3-20}$ cycloalkyl, and $C_{6-20}$ aryl, each of which may be optionally substituted;

$R^6$, $R^{6'}$, $R^9$, and $R^{9'}$ are each independently selected from H, $C_{1-6}$ alkyl, $C_{3-20}$ cycloalkyl, and $C_{5-20}$ aryl, each of which may be optionally substituted; or each $R^6$, $R^{6'}$, $R^9$, and $R^{9'}$ may independently be linked to one or more other $R^6$, $R^{6'}$, $R^9$, or $R^{9'}$ groups. In one aspect, the linker group may be derived from one of the following groups by removal of the appropriate number of hydrogen atoms: $C_{1-6}$ alkyl, $C_{1-6}$ alkyl-Het-$C_{1-6}$ alkyl, $C_{3-20}$ cycloalkyl, $C_{5-20}$ aryl, $C_{1-6}$ alkyl-$C_{3-20}$ cycloalkyl-$C_{1-6}$ alkyl, and $C_{1-6}$ alkyl-$C_{5-20}$ aryl-$C_{1-6}$ alkyl each of which may be optionally substituted; wherein Het is a heteroatom selected from N which may be optionally substituted, O, and S; or one $R^6$ and one $R^{6'}$ attached to the same boron atom and/or one $R^9$ and one $R^{9'}$ attached to the same boron atom are joined together to form a group independently selected from $C_{1-6}$ alkylene, $C_{1-6}$ alkylene-Het-$C_{1-6}$ alkylene, $C_{3-20}$ cycloalkylene, and $C_{5-20}$ arylene, each of which may be optionally substituted; wherein Het is a heteroatom selected from N which may be optionally substituted, O, and S; or one $R^6$, one $R^{6'}$, one $R^9$ and one $R^{9'}$ are joined together to form a tetradentate $C_{8-32}$ cycloalkane, or a tetradentate group having the formula

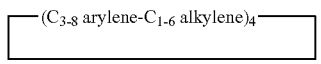

either of which may be optionally substituted, for example with a $C_{1-6}$ alkyl group (e.g., a tert-butyl group); or one $R^6$ and one $R^{6'}$ group on one compound of formula I link to one $R^6$ and one $R^{6'}$ groups on a second independently defined compound of formula I to form a dimer, wherein the linkage between the two independent compounds of formula I is selected from

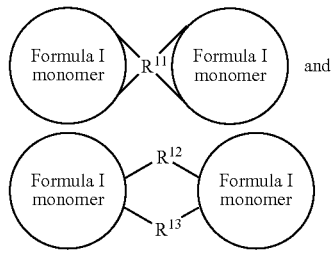

in which $R^{11}$ is selected from a $C_{6-20}$ tetradentate aromatic group, $C_{8-32}$ tetradentate cycloalkane, and tetradentate group having the formula

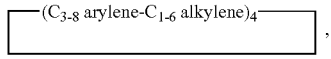, each of which may be optionally substituted, for example with a $C_{1-6}$ alkyl group (e.g., a tert-butyl group); and $R^{12}$ and $R^{13}$ are each independently selected from $C_{1-6}$ alkylene, $C_{3-20}$ cycloalkylene, $C_{3-20}$ arylene, $C_{1-6}$ heteroalkylene, $C_{3-20}$ heterocycloalkylene, and $C_{3-20}$ heteroarylene;

ii) a Lewis base; and iii) a solid matrix component;

wherein, in the presence of a fluorine-containing compound, the organometallic compound forms a complex with one or more fluorine atoms from the fluorine-containing compound to produce a detectable change.

Preferably, the organometallic compound is a compound according to formula I.

Preferably the organometallic compounds according to formula I and formula I' do not bind $CN^-$. Therefore, the fluoride detectors described herein preferably do not detect cyanide-containing compounds.

The Lewis base component may be a solid or a liquid Lewis base, and is preferably a solid Lewis base.

In one embodiment, the Lewis base component ii) and the solid matrix component iii) of the fluoride detector are a single component comprising a basic solid matrix component.

Preferably, the fluoride detector further comprises:

a solid-state oxidant that oxidises a complex between the organometallic compound i) and one or more fluorine atoms from the fluorine-containing compound, but does not oxidise the organometallic compound i) alone.

In some embodiments, the fluoride detector further comprises:

a catalyst that catalyses the release of fluorine atoms from a specific fluorine-containing compound or group of compounds.

Preferably, the fluoride detector further comprises:

the components of an orthogonal reaction that is catalysed, by the complex between the organometallic compound i) and one or more fluorine atoms from the fluorine-containing compound, but is not catalysed by the organometallic compound i) alone.

Cyanide Detectors

In one aspect, the cyanide detector according to the present proposals comprises an indicator component which provides a sensory output initiated by the detectable change in the organometallic compound on exposure to the cyanide-containing compound. For example, the detectable change in the organometallic compound may be an electrochemical change which may initiate a colour change in the indicator component. Preferably, where the cyanide detector does not include an indicator component, the detectable change in the organometallic compound may itself be a sensory output (e.g., a colour change).

Preferably, the indicator component provides an audible, or visible (i.e. optical) output initiated by the detectable change in the organometallic compound on exposure to cyanide-containing compound.

Preferably, the cyanide detector comprises a chemical amplifying system that amplifies the detectable change in the organometallic compound by using a chemical reaction. In one preferred embodiment, the chemical amplifying system comprises a chemical reaction (known as an orthogonal reaction) which is promoted or catalysed by the complex between the organometallic compound and at least one cyanide atom. This means that when even only a small number of cyanide atoms are bound by the boron centre of the organometallic compound, the resultant complex acts as a catalyst for the orthogonal reaction, which forms a part of the chemical amplifying system, and produces a large amount of the product of the orthogonal reaction. In one embodiment, the product of the orthogonal reaction acts as the indicator component (for example, the product may have a particularly distinctive colour that is easily visible when it is produced). Preferably, the product of the orthogonal reaction acts on the indicator component causing it to produce a sensory output.

The organometallic compound may be a compound having a metal atom coordinated by n-electrons from at least one cyclic ligand.

In one embodiment, the organometallic compound is a sandwich compound having a metal atom coordinated by n-electrons from exactly two cyclic ligands or a half-sandwich compound having a metal atom coordinated by n-electrons from exactly one cyclic ligand.

Preferably, the cyclic ligand(s) comprise a ring system containing 3-20 atoms, preferably 5-12 atoms, preferably 5-8 atoms, preferably 5 or 6 atoms, and most preferably 5 atoms.

Preferably, the cyclic ligand(s) are optionally substituted cyclopentadienyl ligands.

In preferred embodiments, one or both of the two substituents on the bis-substituted boryl substituent of the organometallic compound are optionally substituted aryl or heteroaryl groups, optionally substituted cycloalkyl or heterocycloalkyl groups or $C_{1-10}$ alkyl groups (preferably highly branched and/or sterically bulky $C_{1-10}$ alkyl groups such as tert-butyl, tert-octyl, neopentyl, adamantyl, norbornyl, trialkylsilyl (e.g. in which the alkyl group is $C_{1-10}$ alkyl), or perfluoroalkyl (e.g. in which the alkyl group is $C_{1-10}$ alkyl), $C_{5-20}$aryl, $C_{1-10}$ alkyl-$C_{5-20}$ aryl). In preferred embodiments, both of the substituents on the bis-substituted boryl substituent are the same. Preferably the substituents on the bis-substituted boryl substituent are optionally substituted cycloalkyl groups or optionally substituted aryl groups. Preferably, these optional substituents are one or more $C_{1-6}$ alkyl groups, for example three methyl substituents on a phenyl group to form a mesityl (2,4,6-trimethyl phenyl) group.

Preferably, the organometallic compound comprises a transition metal atom.

Preferably, the organometallic compound contains exactly one transition metal atom.

Preferably, the organometallic compound comprises a metal atom selected from Fe, Ru, Os, Co, Cr, Ni, and preferably Fe.

In preferred embodiments, the organometallic compound comprises a sandwich compound (i.e. one having a metal centre and two ring ligands) having a metal centre selected from Fe, Ru, Os, Co, Cr, and Ni, with one or two cyclopentadienyl or arene ligands or with two different arene ligands.

In one embodiment, the organometallic compound comprises a half-sandwich compound (i.e. one having a metal centre and only one ring ligand) having a metal centre selected from Fe, Ru, Os, Co, Cr, and Ni, with one cyclopentadienyl or arene ligands.

Preferably, the organometallic compound comprises a core selected from:

(sandwich compounds) Fe($C_5$ ring)$_2$, Fe($C_6$ ring)$_2$, Ru($C_5$ ring)$_2$, Ru($C_6$ ring)$_2$, Co($C_5$ ring)$_2$, Co($C_6$ ring)$_2$, Cr($C_5$ ring)$_2$, Cr($C_6$ ring)$_2$, Ni($C_5$ ring)$_2$, Ni($C_6$ ring)$_2$, Fe($C_5$ ring)($C_6$ ring), Ru($C_5$ ring)($C_6$ ring), Os($C_5$ ring)($C_6$ ring), Cr($C_5$ ring)($C_6$ ring), Ni($C_5$ ring)($C_6$ ring);

(half-sandwich compounds) Fe($C_5$ ring), Fe($C_6$ ring), Ru($C_5$ ring), Ru($C_6$ ring), Os($C_5$ ring), Os($C_6$ ring), Cr($C_5$ ring), Cr($C_6$ ring), Ni($C_5$ ring), Ni($C_6$ ring).

Preferably, the cyanide detector according to the present proposals comprises either an organometallic compound comprising a unit according to formula II'

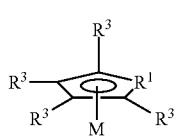

Formula II' or an organometallic compound according to formula II

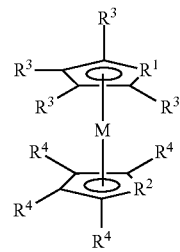

Formula II wherein:

M, $R^1$, $R^2$, $R^3$, $R^4$ are as defined above;

$R^5$, $R^{5'}$, $R^8$ and $R^{8'}$ are each independently selected from optionally substituted $C_{3-20}$ aryl or heteroaryl groups, optionally substituted $C_{3-20}$ cycloalkyl or heterocycloalkyl groups, and $C_{1-10}$ alkyl groups;

wherein each $R^5$, $R^{5'}$, $R^8$ and $R^{8'}$ group may independently be linked to one or more other $R^5$, $R^{5'}$, $R^8$ and $R^{8'}$ groups. In some embodiments the group forming this link may be derived from one of the following groups by removal of the appropriate number of hydrogen atoms: $C_{1-6}$ alkyl, $C_{1-6}$ alkyl-Het-$C_{1-6}$ alkyl, $C_{3-20}$ cycloalkyl, $C_{5-20}$ aryl, $C_{1-6}$ alkyl-$C_{3-20}$ cycloalkyl-$C_{1-6}$ alkyl, and $C_{1-6}$ alkyl-$C_{5-20}$ aryl-$C_{1-6}$ alkyl each of which may be optionally substituted; wherein Het is a heteroatom selected from N which may be optionally substituted, O, and S; or one $R^5$ and one $R^{5'}$ attached to the same boron atom and/or one $R^8$ and one $R^{8'}$ attached to the same boron atom are joined together to form a group independently selected from $C_{1-6}$ alkylene, $C_{1-6}$ alkylene-Het-$C_{1-6}$ alkylene, $C_{3-20}$ cycloalkylene, and $C_{5-20}$ arylene, each of which may be optionally substituted; wherein Het is a heteroatom selected from N which may be optionally substituted, O, and S; or one $R^5$, one $R^{5'}$, one $R^8$ and one $R^{8'}$ are joined together to form a tetradentate $C_{8-32}$ cycloalkane, or a tetradentate group having the formula $$-(C_{3-8}\text{ arylene-}C_{1-6}\text{ alkylene})_4-$$

either of which may be optionally substituted, for example with a $C_{1-6}$ alkyl group (e.g., a tert-butyl group); or one $R^5$ and one $R^{5'}$ group on one compound of formula II link to one $R^5$ and one $R^{5'}$ groups on a second independently defined compound of formula II to form a dimer, wherein the linkage between the two independent compounds of formula II is selected from

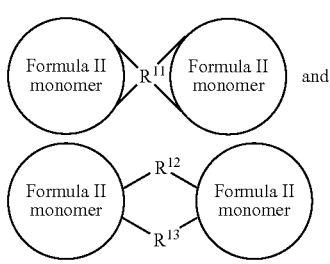

in which $R^{11}$ is selected from a $C_{5-20}$ tetradentate aromatic group, $C_{8-32}$ tetradentate cycloalkane, and tetradentate group having the formula

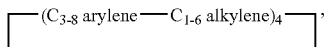

each of which may be optionally substituted, for example with a $C_{1-6}$ alkyl group (e.g., a tert-butyl group); and $R^{12}$ and $R^{13}$ are each independently selected from $C_{1-6}$ alkylene, $C_{3-20}$ cycloalkylene, $C_{3-20}$ arylene, $C_{1-6}$ heteroalkylene, $C_{3-20}$ heterocycloalkylene, and $C_{3-20}$ heteroarylene wherein, in the presence of a cyanide-containing compound, the organometallic compound forms a complex with one or more cyanide atoms from the cyanide-containing compound to produce a detectable change.

Preferably the cyanide detector further comprises a Lewis base; and a solid matrix component.

Preferably, the organometallic compound is a compound according to formula II.

The Lewis base component may be a solid or a liquid Lewis base, and is preferably a solid Lewis base.

In one embodiment, the Lewis base component ii) and the solid matrix component iii) of the detector are a single component comprising a basic solid matrix component.

Preferably, the cyanide detector further comprises:

a solid-state oxidant that oxidises a complex between the organometallic compound and one or more cyanide groups from the cyanide-containing compound, but does not oxidise the organometallic compound alone.

In some embodiments, the cyanide detector further comprises:

a catalyst that catalyses the release of cyanide atoms from a specific cyanide-containing compound or group of compounds.

Preferably, the cyanide detector further comprises:

the components of an orthogonal reaction that is catalysed, by the complex between the organometallic compound and one or more cyanide groups from the cyanide-containing compound, but is not catalysed by the organometallic compound alone.

In preferred embodiments, the organometallic compound used in the cyanide detector also provides a detectable change on exposure to fluoride-containing compounds (such as the same type of compounds with which the organometallic compound in the fluoride detector reacts) leading to a detectable output on exposure to fluoride-containing compounds as well as cyanide-containing compounds.

Methods

In one aspect of the present method, the test environment is a liquid or gaseous environment, preferably an aqueous or gaseous environment, and more preferably a gaseous environment.

In preferred embodiments of the present method, the organometallic compound is as defined above for use in fluoride or cyanide detectors of the present proposals. Preferably, the organometallic compound is as defined in formula I or I' or formula II or II'.

The present fluoride detection method may comprise the steps of:

a) exposing a fluoride detector as described herein to a sample which may or may not contain a fluorine-containing compound;

b) identifying the presence or absence of a detectable change in the detector;

c) correlating the presence or absence of a detectable change in the detector with the presence or absence of a fluorine-containing compound; and d) providing an output to indicate the presence or absence of a fluorine-containing compound.

Preferably, the correlation step c) of the method is a quantitative correlation and the output in step d) indicates the amount of fluorine-containing compound present.

In preferred embodiments the fluoride detector according to the present proposals is designed to detect a fluorine-containing compound selected from:

hydrogen fluoride gas;
hydrofluoric acid;
an acetyl fluoride compound;
sulphur tetrafluoride;
diethylamino sulphur trifluoride;
cyanogen fluoride;
fluoropyridinium salts;
methylphosphonofluoridic acid, 1-methylethylester (GB, Sarin);
methylphosphonofluoridic, 1,2,2-trimethylpropyl ester (GD, Soman);
methylphosphonofluoridic, cyclohexylester (GF, cyclohexylsarin);
alkylphosphonofluoridic, alkylester or arylester; and
dialkylfluorophosphates (DFPs) (such as diisopropyl fluorophosphates).

In some embodiments the method according to the present proposals tests for the presence in a test environment of a fluorine-containing compound selected from:

hydrogen fluoride gas;
hydrofluoric acid;
an acetyl fluoride compound;
sulphur tetrafluoride;
diethylamino sulphur trifluoride;
cyanogen fluoride;
fluoropyridinium salts;
methylphosphonofluoridic acid, 1-methylethylester (GB, Sarin);
methylphosphonofluoridic, 1,2,2-trimethylpropyl ester (GD, Soman);
methylphosphonofluoridic, cyclohexylester (GF, cyclohexylsarin);
alkylphosphonofluoridic, alkylester or arylester; and
dialkylfluorophosphates (DFPs) (such as diisopropyl fluorophosphates).

The present cyanide detection method may comprise the steps of:

a) exposing a cyanide detector as described herein to a sample which may or may not contain a cyanide-containing compound;

b) identifying the presence or absence of a detectable change in the detector;

c) correlating the presence or absence of a detectable change in the detector with the presence or absence of a cyanide-containing compound; and d) providing an output to indicate the presence or absence of a cyanide-containing compound.

Preferably, the correlation step c) of the method is a quantitative correlation and the output in step d) indicates the amount of cyanide-containing compound present.

In preferred embodiments the cyanide detector according to the present proposals is designed to detect a cyanide-containing compound selected from:

Hydrogen cyanide;
Tabun (CA) (Ethyl N,N-dimethylphosphoramidocyanidate);

cyanogen;
cyanogen fluoride;
cyanogen chloride (CK);
cyanogen bromide;
cyanogen iodide; and
cyanogen azide.

In preferred methods, the cyanide detectors can also be used to detect fluoride-containing compounds (such as the same type of fluoride-containing compounds that can be detected using the fluoride detector), i.e. step a) of the method may involve exposing the cyanide detector to a sample which may or may not containing a cyanide-containing or fluorine-containing compound; the correlation step c) may involve indicating the presence or absence of a cyanide-containing or fluorine-containing compound; and the output of step d) may indicate the presence or absence of a cyanide-containing or fluorine-containing compound.

Novel Compounds

A further aspect of the present proposals provides novel organometallic compounds according to formula I, I', II or II, preferably compounds according to formula II or II', more preferably compounds according to formula II.

The present detectors and methods are based on a combination of components which when exposed to a source of hydrogen fluoride, hydrofluoric acid, fluorine containing compound (e.g. a CWA/TIC), hydrogen cyanide or cyanide containing compound (e.g. a CWA/TIC) generates a detectable change. In some embodiments, the detectable change is selected from: a colour change, a change in fluorescence behaviour, a change in the electronic or infrared spectrum, a change in electrochemical behaviour, a precipitation event, and a phase change.

Preferably, the detectable change, e.g. a change in the detector, is quantitively related to the amount of target analyte (i.e. fluorine-containing compound or cyanide-containing compound) present. For example, the electrochemical behaviour of the compound according to formula I, I' or formula II, II' may change in a sufficiently predictable manner that it can be related directly to the respective amount of fluorine-containing compound or cyanide-containing compound present.

This quantitative behaviour may provide an indication of the concentration of the target analyte (i.e. fluorine-containing compound or cyanide-containing compound) present, or it may provide an indication of the cumulative amount of fluorine-containing compound or cyanide-containing compound to which the compound according to formula I, I' or formula II, II' respectively has been exposed, i.e. it may act as a dosimeter.

It is preferred that the reaction between the organometallic compound of formula I or I' and the one or more fluorine atoms from the fluorine-containing compound to form the complex is irreversible.

It is also preferred that the reaction between the organometallic compound of formula II or II' and the one or more cyanide groups from the cyanide-containing compound to form the complex is irreversible.

When this reaction is described as "irreversible", it is meant that the one or more fluorine atoms or cyanide groups form a bond to the organometallic compound, preferably a covalent bond, which may result in the oxidation of the metal centre of the organometallic compound. The bonding of the one or more fluorine atoms or cyanide groups to the organometallic compound may be reversible (i.e. the one or more fluorine atoms or cyanide groups may be released from the organometallic compound when the fluorine-containing or cyanide-containing compound is removed) but the subsequent oxidation of the metal centre does not reverse (i.e. the metal centre is not reduced) when the fluorine-containing or cyanide containing compound is removed. Hence the oxidation of the metal centre, rather than the fluorine atom or cyanide group binding event itself, is irreversible.

Organometallic Component

General Considerations

In preferred embodiments, the organometallic compound is substituted with a plurality of bis-substituted boryl substituents. A greater number of bis-substituted boryl substituents attached to the organometallic compound leads to a more rapid binding of fluorine atoms from a fluorine-containing compound or cyanide groups from a cyanide-containing compound possibly due to the higher concentration of bis-substituted boryl substituents that are able to bind fluorine atoms or cyanide groups and possibly due to the increased electrochemical lability of species with two or more bound fluorine atoms or cyanide groups.

Preferably, the organometallic compound is substituted with from 1 to 10, preferably, 1 to 6, more preferably exactly 1, 2, 3, or 4, bis-substituted boryl substituents.

Fluoride-Reactive Compounds

The first component is a compound according to formula I or formula I', for example this compound may be one of a range of boronic ester derivatives of ferrocene (dicyclopentadienyl iron). Typically, these compounds can be shown, e.g. by NMR spectroscopy, to selectively or preferentially bind fluorine atoms or anions over other anionic analytes.

Non-limiting preferences for the substituent groups in compounds according to formula I or I' are given below.

Preferably, the metal atom M is Fe.

In some embodiments, $R^1$ is —$C(R^3)$—.

In some embodiments, $R^2$ is —$C(R^4)$—.

In some embodiments, $R^1$ is —$C(R^3)$— and $R^2$ is —$C(R^4)$—.

Preferably, exactly one of the $R^3$ groups is —$B(R^5)(R^{5'})$— and the rest of the $R^3$ groups are H.

In some embodiments, exactly two of the $R^3$ groups is —$B(R^5)(R^{5'})$— and the rest of the $R^3$ groups are H.

In some embodiments, exactly one of the $R^4$ groups is —$B(R^8)(R^{8'})$— and the rest of the $R^4$ groups are H.

In some embodiments, exactly two of the $R^4$ groups is —$B(R^8)(R^{8'})$— and the rest of the $R^4$ groups are H.

In some embodiments, exactly one of the $R^3$ groups is —$B(R^5)(R^{5'})$— and exactly one of the $R^4$ groups is —$B(R^8)(R^{8'})$— and the rest of the $R^3$ and $R^4$ groups are H.

In some embodiments, exactly two of the $R^3$ groups is —$B(R^5)(R^{5'})$— and exactly two of the $R^4$ groups is —$B(R^8)(R^{8'})$— and the rest of the $R^3$ and $R^4$ groups are H.

In some embodiments, exactly two of the $R^3$ groups is —$B(R^5)(R^{5'})$—, exactly one of the $R^4$ groups is —$B(R^8)(R^{8'})$—, exactly one of the $R^4$ groups is $C_{1-6}$ alkyl (e.g. straight-chain alkyl, such as methyl, ethyl, propyl, butyl, pentyl, or hexyl, and preferably ethyl), and the rest of the $R^3$ and $R^4$ groups are H.

Preferably, all $R^5$ groups are $OR^6$, all $R^{5'}$ groups are $OR^{6'}$, all $R^8$ groups are $OR^9$, and all $R^{8'}$ are $OR^{9'}$.

In some embodiments, all $R^6$ and $R^{6'}$ groups present are joined together and all $R^9$ and $R^{9'}$ groups present are joined together each independently to form a group selected from $C_{1-6}$ alkylene, $C_{1-6}$ alkylene-Het-$C_{1-6}$ alkylene, $C_{3-20}$ cycloalkylene, and $C_{5-20}$ arylene, each of which may be optionally substituted; wherein Het is a heteroatom selected from N which may be optionally substituted, O, and S. In one aspect, Het is N which may be optionally substituted with a $C_{1-6}$ alkyl group (e.g., a straight chain alkyl group, such as methyl, ethyl, propyl, butyl, pentyl, or hexyl, and preferably methyl). In one aspect, the $C_{1-6}$ alkylene, $C_{1-6}$ alkylene-Het- $C_{1-6}$ alkylene, $C_{3-20}$ cycloalkylene, or $C_{5-20}$ arylene group is optionally substituted with a group selected from:

$C_{1-6}$ alkyl (e.g., a straight chain alkyl group, such as methyl, ethyl, propyl, butyl, pentyl, or hexyl, and preferably methyl, or a branched alkyl group such as n-propyl, i-propyl, t-butyl, i-butyl, sec-butyl, i-pentyl (amyl), n-pentyl, and n-hexyl, and preferably t-butyl);

$C_{1-6}$ alkoxyl (e.g., methoxy, ethoxy, propoxy, butoxy, t-butoxy, and preferably methoxy);

$C_{3-20}$ aryl (preferably $C_{5-14}$ aryl, such as phenyl, naphthyl, anthracenyl);

$C_{3-20}$ heterocyclyl (e.g., furyl, thienyl, pyrrolyl, pyridinyl, oxazolyl, isoazolyl, isoazinyl, thiazolyl, isothiazolyl, imidazolyl, pyrazolyl, piperidyl, piperazinyl, mopholinyl, thiomorpholinyl etc., and preferably piperidyl or morpholinyl);

$C_{1-6}$ alkyl-$C_{3-20}$ aryl; and $C_{1-6}$ alkyl-$C_{3-20}$ heterocyclyl (e.g., methylene-piperidinyl or methylene-morpholinyl).

In preferred embodiments, all $R^6$ and $R^{6'}$ groups present are joined together and all $R^9$ and $R^{9'}$ groups present are joined together each independently to form a group selected from (in which ∿∿∿ denotes the point of attachment of the group):

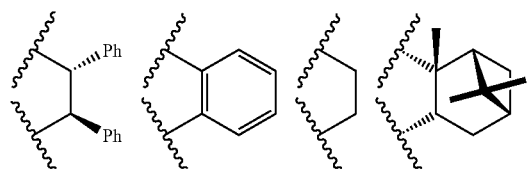

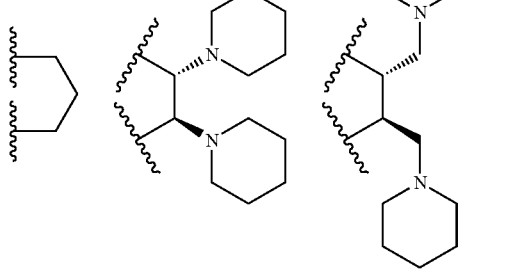

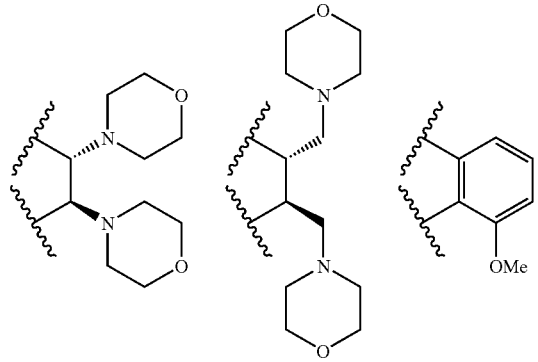

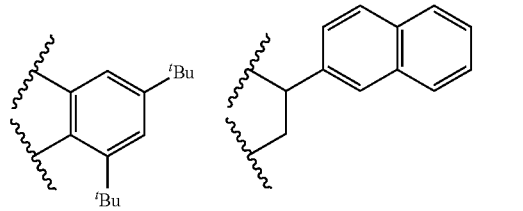

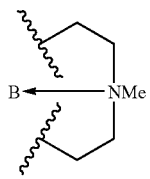

$R^6$, $R^{6'}$, $R^9$ and $R^{9'}$ may be joined together to form a tetradentate group selected from

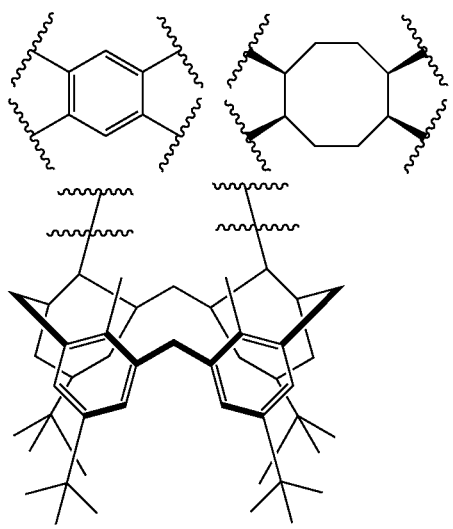

Preferably, $R^{11}$ is a tetradentate group selected from

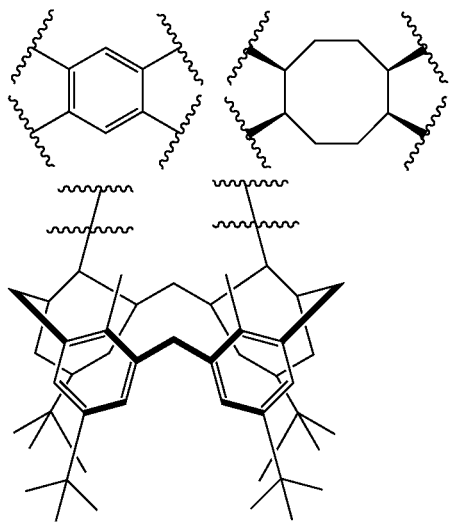

In preferred embodiments, the organometallic compound utilised in the fluoride-detectors described herein does not bind cyanide groups (e.g. from cyanide-containing compounds).

Preferably, the organometallic compound utilised in the fluoride-detectors described herein is selected from the compounds shown in any of tables 1, 1a, 2, 3, 4 or 5.

TABLE 1
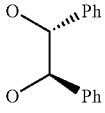
| Compound | 1$^s$ | 1$^c$ | 1$^e$ | 1$^{pin}$ | 1$^{pr}$ | 1$^{plp}$ | 1$^m$ | 1$^{bn}$ |
|---|---|---|---|---|---|---|---|---|
| (OR)$_2$ | 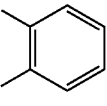 |  | 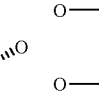 | 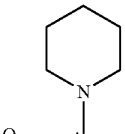 | 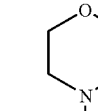 | 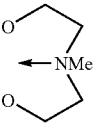 |  | 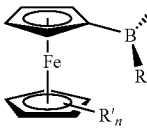 |
TABLE 1a
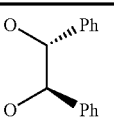
| Compound | 1$^{s*}$ |
|---|---|
| R$_2$ | 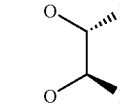 |
| R'$_n$ | Me$_5$ |
TABLE 2
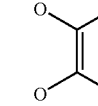
| Compound | 2$^s$ | 2$^c$ | 2$^e$ | 2$^{pin}$ | 2$^n$ |
|---|---|---|---|---|---|
| (OR)$_2$ | 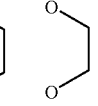 |  | 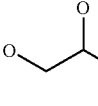 | | |

TABLE 2-continued

| Compound | $2^{bc}$ | $2^{mc}$ | $2^{ca}$ |
|---|---|---|---|
| (OR)₂ | 3,5-di-tert-butylcatecholate | 3-methoxycatecholate | 1/2 calixarene-based diolate |

TABLE 3 ferrocene-based tetraboronate ester with ethyl substituent

| Compound | $3^s$ | $3^e$ | $3^{pin}$ |
|---|---|---|---|
| (OR)₂ | hydrobenzoin | ethylene glycol | pinanediol |

TABLE 4 ferrocene-based tetraboronate ester

| Compound | $4^s$ | $4^e$ | $4^{pin}$ | $4^n$ |
|---|---|---|---|---|
| (OR)₂ | hydrobenzoin | ethylene glycol | pinanediol | 2-naphthyl glycolate |

TABLE 5

| Compound | 5$^{thb}$ | 5$^{co}$ | 5$^{ca}$ |
|---|---|---|---|
| (ORO)$_2$ | | | |

Cyanide Reactive Compounds

The organometallic component in the cyanide detectors described herein is a compound according to formula II or formula II', for example this compound may be one of a range of derivatives of ferrocene (dicyclopentadienyl iron, abbreviated to "Fc") functionalised boranes. Typically, these compounds can be shown, e.g. by NMR spectroscopy, to selectively or preferentially bind cyanide groups or anions over other analytes. In some cases, these compounds also bind fluorine atoms or fluoride anions, in addition to cyanide groups.

Non-limiting preferences for the substituent groups in compounds according to formula II or II' are given below.

Preferably, the metal atom M is Fe.

In some embodiments, $R^1$ is —C($R^3$)—.

In some embodiments, $R^2$ is —C($R^4$)—.

In some embodiments, $R^1$ is —C($R^3$)— and $R^2$ is —C($R^4$)—.

Preferably, exactly one of the $R^3$ groups is —B($R^5$)($R^{5'}$)— and the rest of the $R^3$ groups are H.

In some embodiments, exactly two of the $R^3$ groups is —B($R^5$)($R^{5'}$)— and the rest of the $R^3$ groups are H.

In some embodiments, exactly one of the $R^4$ groups is —B($R^8$)($R^{8'}$)— and the rest of the $R^4$ groups are H.

In some embodiments, exactly two of the $R^4$ groups is —B($R^8$)($R^{8'}$)— and the rest of the $R^4$ groups are H.

In some embodiments, exactly one of the $R^3$ groups is —B($R^5$)($R^{5'}$)— and exactly one of the $R^4$ groups is —B($R^8$)($R^{8'}$)— and the rest of the $R^3$ and $R^4$ groups are H.

In some embodiments, exactly two of the $R^3$ groups is —B($R^5$)($R^{5'}$)— and exactly two of the $R^4$ groups is —B($R^8$)($R^{8'}$)— and the rest of the $R^3$ and $R^4$ groups are H.

In some embodiments, exactly two of the $R^3$ groups is —B($R^5$)($R^{5'}$)—, exactly one of the $R^4$ groups is —B($R^8$)($R^{8'}$)—, exactly one of the $R^4$ groups is $C_{1-6}$ alkyl (e.g. straight-chain alkyl, such as methyl, ethyl, propyl, butyl, pentyl, or hexyl, and preferably ethyl), and the rest of the $R^3$ and $R^4$ groups are H.

Preferably, all $R^5$, $R^{5'}$, $R^8$ and $R^{8'}$ groups are optionally substituted $C_{3-20}$ aryl or heteroaryl groups, optionally substituted $C_{3-20}$ cycloalkyl or heterocycloalkyl groups, or $C_{1-10}$ alkyl groups.

Preferably all $R^5$, $R^{5'}$, $R^8$ and $R^{8'}$ groups are optionally substituted $C_{3-20}$ aryl groups, such as phenyl groups.

Preferably the optional substituents on the $R^5$, $R^{5'}$, $R^8$ and $R^{8'}$ groups are selected from:

$C_{1-10}$ alkyl (preferably straight chain alkyl), $C_{1-10}$ heteroalkyl (e.g. $C_{1-10}$ alkoxy, $C_{1-10}$ ether);

$C_{1-10}$ alkenyl, $C_{1-10}$ heteroalkenyl $C_{3-20}$ cycloalkyl, $C_{3-20}$ heterocycloalkyl;

$C_{3-20}$ aryl, $C_{3-20}$ heteroaryl;

Halo (e.g., F, Cl, Br, I);

Hydroxy;

Oxo (i.e., =O);

Carboxy (i.e., —COOH);

Ester (e.g., —C(=O)O—$C_{1-6}$ alkyl);

Amino (e.g., —NH$_2$, —NH$^2$, —NH—$C_{1-6}$ alkyl, —N($C_{1-6}$ alkyl)$_2$);

Amido (e.g., —C(=O)NH$_2$, —C(=O)NH—$C_{1-6}$ alkyl, —C(=O)N($C_{1-6}$ alkyl)$_2$);

Nitro (—NO$_2$); and $C_{1-10}$ aldehydes or ketones.

Preferably the optional susbstituents on the $R^5$, $R^{5'}$, $R^8$ and $R^{8'}$ groups are $C_{1-10}$ alkyl groups, more preferably methyl groups.

Where the $R^5$, $R^{5'}$, $R^8$ or $R^{8'}$ groups are phenyl groups, the optional substituents may be present at any combination of substitutable positions, for example 2,6-, 3,5-, 2,5-, 2,4,6-, 3,4,5-, 2,4,5-, 2,3,4,6-, 2,3,5,6-, or 2,3,4,5,6-positions. Preferably, the $R^5$, $R^{5'}$, $R^8$ and $R^{8'}$ groups are trisubstituted at the 2,4,6-positions of a phenyl ring (e.g. a mesityl group when the substituent is methyl).

In preferred embodiments, the organometallic compound utilised in the cyanide-detectors described herein also binds fluoride groups (e.g. from fluoride-containing compounds).

Preferably the organometallic compound II or II' is air and moisture stable. It is thought that when one or more of $R^5$, $R^{5'}$, $R^8$ and $R^{8'}$ is a sterically bulky group, and in particular a mesityl (2,4,6-trimethyl phenyl) group, the compound according to formula II or II' is particularly air and moisture stable. Hence the use of mesityl groups in at least one of the $R^5$, $R^{5'}$, $R^8$ and $R^{8'}$ positions is preferred. Particularly preferable compounds are those in which both $R^5$ and $R^{5'}$ and/or $R^8$ and $R^{8'}$ are mesityl groups.

Preferably, the organometallic compound utilised in the cyanide-detectors described herein is selected from:

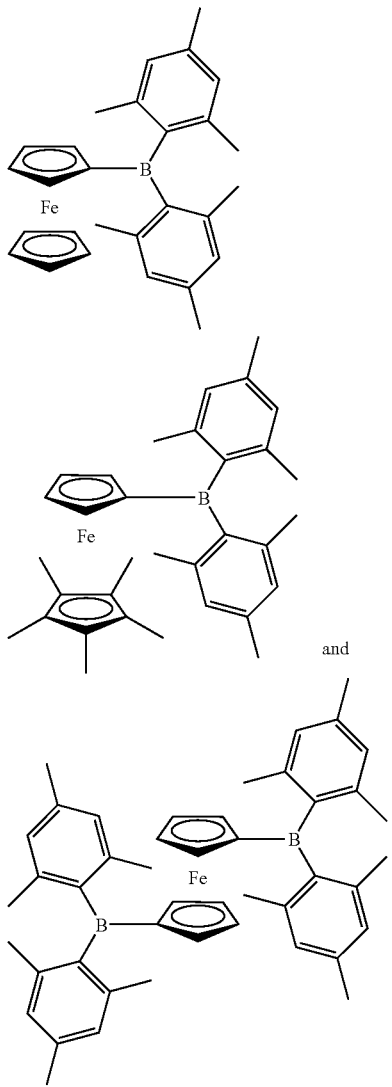

Fluorescent Groups

The organometallic compound according to formula I, I', II or II' may include a fluorescent substituent group, for example one or more of the substituent groups selected from $R^3$, $R^4$, $R^5$, $R^{5'}$, $R^6$, $R^{6'}$, $R^7$, $R^{7'}$, $R^8$, $R^{8'}$, $R^9$, $R^{9'}$, $R^{10}$, and $R^{10'}$, preferably $R^3$ and $R^4$, is a fluorophore, i.e. a group which under certain conditions may fluoresce, preferably in the visible light range. In these embodiments, the fluorescence behaviour of the fluorophore is altered on binding of one or more fluorine atoms or cyanide groups to the organometallic compound. The change in fluorescence behaviour of the fluorophore may represent either the detectable change in the organometallic compound, or the fluorophore represents the indicator component of a detector according to the present proposals and the change in fluorescence behaviour represents a sensory output of the detector.

Preferably, the detector comprises a fluorophore as a component separate from the organometallic compound.

In some embodiments the fluorophore is selected from polyaromatic systems, a dansyl group, a porphyrin, a phthalocyanin, and a lanthanide complex.

In preferred embodiments, the fluorescence behaviour of the fluorophore is quenched, and preferably totally extinguished, on binding of one or more fluorine atoms or cyanide groups to the compound according to formula I, I', II or II'.

Preferably, the fluorescence behaviour of the fluorophore is enhanced on binding of one or more fluorine atoms or cyanide groups to the compound according to formula I, I', II or II'. Preferably the fluorophore does not fluoresce when the compound according to formula I, I', II or II' is not bound to one or more fluorine atoms or cyanide groups, but does fluoresce when the compound according to formula I, I', II or II' is bound to one or more fluorine atoms or cyanide groups.

In all of the above aspects and embodiments, the term "optionally substituted" may include substitution with one or more groups selected from:

$C_{1-6}$ alkyl, $C_{1-6}$ heteroalkyl (e.g. $C_{1-6}$ alkoxy);
$C_{1-6}$ alkenyl, $C_{1-6}$ heteroalkenyl
$C_{3-20}$ cycloalkyl, $C_{3-20}$ heterocycloalkyl;
$C_{3-20}$ aryl, $C_{3-20}$ heteroaryl;
Halo (e.g., F, Cl, Br, I);
Hydroxy;
Oxo (i.e., =O);
Carboxy (i.e., —COOH);
Ester (e.g., —C(=O)O—$C_{1-6}$ alkyl);
Amino (e.g., —NH$_2$, —NH—$C_{1-6}$ alkyl, —N($C_{1-6}$ alkyl)$_2$);
Amido (e.g., —C(=O)NH$_2$, —C(=O)NH—$C_{1-6}$ alkyl, —C(=O)N($C_{1-6}$ alkyl)$_2$); and
Nitro (—NO$_2$).

The optional substituents on the $C_{3-20}$ aryl, $C_{3-20}$ heteroaryl, $C_{3-20}$ cycloalkyl, or $C_{3-20}$ heterocycloalkyl groups may be selected from:

$C_{1-10}$ alkyl, $C_{1-10}$ heteroalkyl (e.g. $C_{1-10}$ alkoxy, $C_{1-10}$ ether);
$C_{1-10}$ alkenyl, $C_{1-10}$ heteroalkenyl
$C_{3-20}$ cycloalkyl, $C_{3-20}$ heterocycloalkyl;
$C_{3-20}$ aryl, $C_{3-20}$ heteroaryl;
Halo (e.g., F, Cl, Br, I);
Hydroxy;
Oxo (i.e., =O);
Carboxy (i.e., —COOH);
Ester (e.g., —C(=O)O—$C_{1-6}$ alkyl);
Amino (e.g., —NH$_2$, —NH—$C_{1-6}$ alkyl, —N($C_{1-6}$ alkyl)$_2$);
Amido (e.g., —C(=O)NH$_2$, —C(=O)NH—$C_{1-6}$ alkyl, —C(=O)N($C_{1-6}$ alkyl)$_2$);
Nitro (—NO$_2$); and
$C_{1-10}$ aldehydes or ketones.

Lewis Base Component

The Lewis base component of the detector acts to coordinate the remainder of the fluorine-containing compound or cyanide-containing compound after one or more fluorine or cyanide atoms respectively have been bound to the compound according to formula I, I', II or II'. For example, if the fluorine-containing compound that is being detected is HF, the Lewis base component binds the protons that remain once the compound according to formula I or I' has bound the fluorine atom. Equally, if the cyanide-containing compound that is being detected is HCN, the Lewis base component binds the protons that remain once the compound according to formula II or II' has bound the cyanide group.

Preferably, the Lewis base is a solid compound. In preferred embodiments, the Lewis base is a low-volatility compound, i.e. it has a negligible vapour pressure at standard temperature and pressure (298K and 1 atm.). The Lewis base may be incorporated into the compound according to formula I, I', II or II'. For example, one of the substituents on the compound according to formula I, I', II or II' is a Lewis basic substitutent. Examples of Lewis basic substituent groups include: aliphatic or aromatic bases containing nitrogen, oxygen, sulphur, or phosphorus atoms as the donor; carbanion; and inorganic bases.

Preferably, the Lewis base component is selected from aliphatic or aromatic bases containing nitrogen, oxygen, sulphur, or phosphorus atoms as the donor; carbanion; and inorganic bases.

Solid Matrix Component

Detectors according to the present proposals include a solid matrix component with which the compound according to formula I, I', II or II' and the Lewis base component are combined. Typically, this solid matrix provides a solid support material for the active compound (the compound according to formula I, I', II or II'). Preferably, the inclusion of a solid matrix component provides additional bulk to the detector composition which means that less active compound (compound according to formula I, I', II or II') is required in each device.

In some embodiments, the solid matrix is a basic material and so acts as both the solid matrix and the Lewis base component.

Preferably, the solid matrix is a polar compound suitable for supporting and dispersing the components of the detector. The matrix component preferably provides a high surface area, hence increasing the surface area in contact with the analyte (hence increasing the reaction speed of the detector). The solid matrix may also have the effect of preventing individual components of the detector from being leached out of the detector (i.e. the solid matrix stabilises the mixture of components comprising the detector).

Preferably, the solid matrix is selected from a cellulose derivative (e.g. paper), silica, alumina, and zeolites, and is preferably paper.

Catalyst Component

The detectors according to the present proposals may include a catalyst component (e.g. a hydrolysis catalyst) that catalyses the release of fluorine atoms or cyanide groups from the fluorine-containing compound or cyanide-containing compound respectively, or from a group or class of fluorine-containing or cyanide containing compounds. For example, the catalyst component may be a catalyst for the decomposition of fluorine-containing compounds (such as TICs or CWAs) to HF or it may catalyse the decomposition of cyanide-containing compounds (such as Tabun) to HCN. The presence of the released HF or HCN can then be detected in the usual manner.

In preferred embodiments, the catalyst component is a solid component.

Preferably, the catalyst component also acts as the solid support component.

Preferably, the catalyst component also acts as the Lewis base component.

The catalyst component may be a metal based molecular systems or an enzyme.

Preferably, the catalyst component is selected from enzymes (e.g.

choline esterase, DFP-ase), d-block metal coordination compounds, and f-block metal coordination compounds.

Oxidant

When the organometallic component of a detector described herein binds to an analyte, such as a fluorine atom or cyanide group, it is then oxidised by an oxidant to produce a detectable change that triggers or comprises the output of the detector.

The oxidant oxidises the complex formed by the organometallic compound with a fluorine atom or cyanide group, but does not oxidise the organometallic compound alone (i.e. the oxidation only takes place when a fluorine atom or cyanide group binds to the organometallic compound).

In some cases, the oxidant is oxygen in the air so the detector does not contain any additional oxidant, it simply relies on the atmospheric oxygen to oxidise the complex formed by the organometallic compound with a fluorine atom or cyanide group. However, in some cases the oxidation can be slow when atmospheric oxygen is utilised because the rate of oxidation is thought to be controlled by the diffusion of oxygen to the organometallic compound. This drawback can be overcome in many cases by using a solid state oxidant which is preferably intimately mixed with the organometallic compound (hence gaseous diffusion of the oxidant to the organometallic compound is not the rate limiting step of the oxidation).

Solid State Oxidant Component

In preferred embodiments, the detectors according to the present proposals include a solid state oxidant component that oxidises the complex formed between the compound according to formula I, I', II or II' and the one or more fluorine atoms, but does not oxidise the compound according to formula I, I', II or II' alone (i.e. in the absence of any bound fluorine atoms or cyanide groups).

Preferably, the solid state oxidant is tuned electrochemically such that it will perform in this way. In other words, the oxidant has a suitable oxidation potential that it does not oxidise the organometallic compound (of formula I, I', II or II') when it is not bound to the desired analyte (fluorine atom(s) or cyanide group(s)) but when an analyte group (fluorine or cyanide) is bound to the organometallic compound, the oxidation potential of the oxidant is such that it oxidises the organometallic compound and is itself reduced. For example, the iron centre of a ferrocene-based organometallic compound is typically in the +II oxidation state and on binding of a fluorine atom or cyanide group, the organometallic-analyte complex becomes more susceptible to oxidation and the oxidant oxidises the iron centre from the +II oxidation state to +III (typically resulting in a colour change from orange to blue/green).

In preferred embodiments, the oxidant is a component which produces a detectable effect when it oxidises the organometallic complex with the desired analyte (fluorine atom or cyanide group) and is itself reduced. For example, in the oxidant preferably exhibits a colour change when it is reduced (i.e. when it oxidises the organometallic-analyte complex).

In some embodiments, the oxidant is a dye compound which changes colour when it is reduced (i.e. when it oxidises the organometallic-analyte complex). Most preferably, this dye compound is a tetrazolium compound which may be selected from derivatives of and including tetrazolium violet, derivatives of and including nitro blue tetrazolium, derivatives of and including MTT (Thiazolyl Blue Tetrazolium Bromide), derivatives of and including 5-Cyano-2,3-bis(4-methylphenyl)-2H-tetrazolium chloride (CTC) and derivatives of and including 2,3,5-Triphenyl-tetrazolium chloride, resazurin and transition metal chelate complexes including trivalent Fe, Ru, Os complexes of 2,2'-bipyridines, 1,10-phenanthrolines, 2,2',6',2"-terpyridines.

These tetrazolium dyes are particularly useful because they exhibit a significant colour change when their oxidation state is changed (e.g. when they act as an oxidant to oxidise the organometallic-analyte complex). For example, UV/visible spectroscopy of the detector typically shows a large change in extinction coefficient on reduction of tetrazolium dye compounds.

In preferred embodiments, the oxidant is MTT, which changes from pale yellow to deep purple blue in colour when it acts as oxidant to oxidise the organometallic-analyte complex.

In some embodiments, the solid state oxidant increases the kinetics of response of the detector by increasing the intimacy of mixing with the sensor component. This obviates the need for diffusion of the oxidant (which otherwise could be just dioxygen in the air) to the sensor/fluoride complex (which has an associated delay), meaning that due to the proximity of the relevant components, oxidation occurs more rapidly.

The tetrazolium dyes are particularly preferred because they result in a detector which has a very fast response time to the presence of a desired fluoride or cyanide analyte. The response time for a detector incorporating a tetrazolium dye may be of the order of less than 1 about second, preferably less than about 500 ms, preferably less than about 250 ms, preferably less than about 100 ms or preferably less than about 50 ms.

Furthermore, the solid state oxidant may be meta-chloro perbenzoic acid (mCPBA) or a quinone (e.g., a quinone selected from any para-quinone featuring an appropriate redox potential) or it may preferably be a tetrazolium dye, such as MTT or tetrazolium violet.

Orthogonal Reaction

Typically the orthogonal reaction may be a reaction involving a colour change based on a known chemical dye (e.g. a redox active dye). Many such reactions have large extinction coefficient differences between the reactants and the products, for example bleaching type reactions which are thermodynamically favourable but are slow in the absence of an electron transfer catalyst. In this case, the adduct between the organometallic compound and the one or more fluorine atoms or cyanide groups (or the oxidised form of this adduct) may act as the electron transfer catalyst which increases the speed of the orthogonal reaction so resulting in a large change in the extinction coefficient of a component of the orthogonal reaction which either alters the output of the detector, or itself comprises the output of the detector (e.g. as a colour change).

Differentiation Between Fluorine-Containing and Cyanide-Containing Analytes.

In another aspect, the present application includes a detector which can identify whether it is detecting a fluoride-containing compound or a cyanide-containing compound.

The organometallic compounds according to formula I and/or I' preferably bind fluorine atoms and not cyanide groups. Therefore, a detector which uses these compounds as the active component will detect fluorine-containing compounds in the presence of cyanide-containing compounds.

However, the identification of cyanide containing compounds is more difficult because the organometallic compounds according to formula II or II' typically bind cyanide groups and also may bind fluorine atoms. This makes selective detection and identification of cyanide-containing compounds more difficult.

The binding characteristics of the organometallic compounds of formula I, I', II or II' are thought to depend on their Lewis acidity. A strong Lewis acid will show a similar binding affinity for both fluorine atoms and cyanide groups. However, the use of a weaker Lewis acid results in binding of only fluorine atoms in the presence of cyanide groups, i.e. the compounds become selective for fluorine atoms due to the high strength of the Boron-Fluorine bond.

Using these different responses to fluorine atoms and cyanide groups, the present application provides a detector comprising:

i) an organometallic compound of formula I or I' which binds to one or more fluorine atoms from fluorine-containing compounds and does not bind to cyanide groups from cyanide-containing compounds; and ii) an organometallic compound of formula II or II' which can bind both one or more fluorine atoms from fluorine-containing compounds AND one or more cyanide groups from cyanide-containing compounds.

Such a detector can be used to identify which analyte (fluorine-containing compound or cyanide-containing compound) is present in a sample. Table 6 indicates the various responses of the components i) and ii) of such a detector.

TABLE 6

| | Compound | |
|---|---|---|
| | i) | ii) |
| Fluorine-containing compound | Binds | Binds |
| Cyanide-containing compound | Does not bind | Binds |

From table 6, it can be seen that in the presence of a fluorine-containing compound, both component i) and component ii) will bind fluorine atoms resulting in a detectable change in both components. However, in the presence of a cyanide-containing compound, component ii) will bind cyanide groups resulting in a detectable change but component i) will not. Therefore, by monitoring components i) and ii) separately, it is possible to determine which analyte (fluorine-containing compound or cyanide-containing compound) is present in a given sample, preferably by a colorimetric determination method.

In order to obtain a detector having this ability to identify which of the fluorine/cyanide analytes is present in a sample, it may, in certain cases, be preferable to use a tetrazolium dye as the oxidant because such dyes typically oxidise the complex between component ii) and cyanide groups and do not oxidise the complex between component i) and cyanide groups. Hence the colorimetric change in component i) is observed only in the presence of fluoride-containing compounds.

It should be noted that the present proposals include detectors and methods comprising each of the independent aspects and/or embodiments described herein, and also, any combination of two or more of the aspects, preferences or features of particular embodiments described herein (i.e. any one of the aspects, preferences, or features of particular embodiments described herein is freely combinable with any one or more of the other aspects, preferences, or features of particular embodiments).

EXAMPLES

Manipulations were carried out under an inert atmosphere (argon or dinitrogen), using dry oxygen-free solvents due to the air- and moisture sensitivity of the starting materials dibromoborylferrocene, 1,1'-bis(dibromoboryl)ferrocene, 1-ethyl-1',3,3'-tris(dibromoboryl)-ferrocene, 1,1',3,3'-tetrakis(dibromoboryl)ferrocene and n-butyllithium.

Example 1

Preparation of $1^s$, $1^c$ and $1^{pin}$

A common method was employed in both cases (route 1, Scheme 1). The appropriate diol (e.g. 2.3 g, 10.74 mmol of stilbenediol for 1$^s$, 10.74 mmol catechol (1,2,-dihydroxybenzene) for 1$^c$; and 10.74 mmol pinanediol for 1$^{pin}$) was dried in vacuo, dissolved in toluene (ca. 50 ml), and the resulting solution cooled to −78$^2$C. n-Butyllithium (2 equivalents of a 1.6 M solution in hexanes) was added dropwise by syringe. The resulting slurry was warmed to room temperature and stirred for a further 2 h. A solution of dibromoborylferrocene (1 equiv.) in toluene was transferred via cannula to the dilithiate mixture at room temperature, and stirred for 24 h. Cannula filtration of the cloudy reaction mixture yielded a clear orange filtrate, and an off-white residue. Removal of the toluene solvent in vacuo afforded an oily orange residue, which was subjected to further continuous pumping. Hexane or petroleum ether was used to wash the solid, combining the washings each time by cannula filtration until the washings were colourless. Finally, recrystallisation from the same solvent at −30° C. yielded 1$^s$ (or 1$^c$) in a spectroscopically and analytically pure form. 1$^s$ was isolated as an air-stable orange crystalline solid in 64% yield. Single crystals were obtained by slow evaporation of solvent from a solution in petroleum ether (40-60° C.). 1$^c$ isolated as an air-sensitive orange solid in 26% yield. Single crystals of 1$^c$ were obtained by recrystallisation from a hexane solution at −30° C. 1$^{pin}$ was obtained by a similar method and isolated as an orange crystalline solid in 37% yield. Single crystals were obtained by slow cooling of a concentrated acetonitrile solution from 40° C. to room temperature.

Spectroscopic and Crystallographic Data for 1$^s$:
$^1$H NMR ([D$_6$]benzene, 20° C.), δ 4.17 [s, 5H, C$_5$H$_5$], 4.29 [m, 2H, C$_5$H$_4$], 4.76 [m, 1H, C$_5$H$_4$], 4.80 [m, 1H, C$_5$H$_4$], 5.25 [S, 2H, CH of chelate], 7.10-7.28 [m, 10H, C$_6$H$_5$].
$^1$H NMR ([D]chloroform, 20° C.), δ 4.25 [s, 5H, CH of C$_5$H$_5$], 4.49 [s, 2H, CH of C$_5$H$_4$], 4.59 [m, 2H, CH of C$_5$H$_4$], 5.29 [s, 2H, CH of chelate], 7.37-7.42 [m, 10H, C$_6$H$_5$].
$^{13}$C NMR ([D$_6$]benzene, 20° C.), δ 68.8 [CH of C$_5$H$_5$], 72.7 [CH of C$_5$H$_4$], 74.3, 74.4 [CH of C$_5$H$_4$], 86.7 [CH of chelate], 126.1 [aromatic CH], 128.8 [aromatic CH], 141.1 [aromatic quaternary].
$^{11}$B NMR ([D$_6$]benzene, 20° C.), δ 34.1.
IR (KBr disk, cm$^{-1}$), v 3085 w, 2918 w, 1501 md, 1481 st, 1451 md, 1379 md, 1372 w, 1321 st, 1298 w, 1269 md, 1205 w, 1173 md, 1128 st, 1105 md, 1036 md, 998 md, 826 md, 764 md, 701 md, 685 w.
UV/Vis (chloroform): λ$_{max}$=448 nm, ε=179 cm$^-$ mol$^{-1}$ dm$^3$.
MS(EI): M$^+$=408 (100%), exact mass (calc.) m/z 408.0984, (obs.) 408.0985.
Crystal data (for S,S-1$^s$): C$_{24}$H$_{21}$BFeO$_2$, hexagonal, P3$_2$, a=9.5746(3), b=9.5746(3), C=18.2224(7) Å, V=1446.70(8) Å$^3$, Z=3, D$_{calc}$=1.405 g cm$^{-3}$, μ(MoKα)=0.799 mm$^{-1}$. A suitable crystal was covered in pre-dried mineral oil and mounted at 150(2) K. 3585 unique reflections were collected (3.3<θ<27.5°). Final R-factor: R$_1$=0.026.

Spectroscopic and Crystallographic Data for 1$^c$:
$^1$H NMR ([D$_6$]benzene, 20° C.), δ 3.95 [s, 5H, C$_5$H$_5$], 4.28 [m, 2H, C$_5$H$_4$], 4.78 [m, 2H, C$_5$H$_4$], 6.87-7.89 [m, 2H, C$_6$H$_4$], 7.16-7.19 [m, 2H, C$_6$H$_4$].
$^1$H NMR ([D]chloroform, 20° C.), δ 4.15 [s, 5H, CH of C$_5$H$_5$], 4.56 [m, 2H, CH of C$_5$H$_4$], 4.68 [m, 2H, CH of C$_5$H$_4$], 7.08-7.12 [m, 2H, C$_6$H$_4$], 7.25-7.27 [m, 2H, C$_6$H$_4$].
$^{13}$C NMR ([D$_6$]benzene, 20° C.), δ 68.8 [CH of C$_5$H$_5$], 73.2 [CH of C$_5$H$_4$], 73.9 [CH of C$_5$H$_4$], 112.4 [aromatic CH], 122.6 [aromatic CH].
$^{11}$B NMR ([D$_6$]benzene, 20° C.), δ 34.3.
IR (KBr disk, cm$^{-1}$), v 3304 w, 1506 md, 1469 st, 1382 md, 1312 st, 1235 st, 1112 md, 1025 w, 1002 w, 894 w, 810 w, 751 st.
UV/Vis (chloroform): λ$_{max}$ (ε) 434 nm.
MS(EI): M$^+$=304 (100%), exact mass (calc.) m/z 304.0358, (obs.) 304.0362.
Crystal data for 1$^c$: C$_{16}$H$_{13}$BFeO$_2$, triclinic, P-1, a=5.9929 (2), b=7.8005(2), c=13.7991(5) Å, β=96.6752(17)°, V=640.70(4) Å$^3$, z=2, D$_{calc}$=1.575 g cm$^{-3}$, μ(MoKα)=1.172 mm$^{-1}$. A suitable crystal was covered in pre-dried mineral oil and mounted at 150(2) K. 2854 unique reflections were collected (3.0<θ<27.5°). Final R-factor: R$_1$=0.034.

Spectroscopic and Crystallographic Data for 1$^{pin}$:
$^1$H NMR ([D]chloroform, 20° C.), 0.42 [s, 3H, H-8], 0.93 [s, 3H, H-9], 1.21 [s, 3H, H-10], 1.33 [d J=10 Hz, 1H, H-6a], 1.55 [m, 1H, H-5], 1.89-2.08 [overlapping m, 4H, H-1, H-4a, H-4b, H-6b], 4.03 [s, 5H, C$_5$H$_5$], 4.10 [m, 2H, C$_5$H$_4$], 4.11 [d, 1H, H-3], 4.58 [d, 2H, C$_5$H$_4$].
$^{13}$C NMR ([D]chloroform, 20° C.), 22.5, 25.5, 25.7, 27.9, 34.7, 36.8, 38.5, 50.4, 73.1, 76.7 [pinane backbone], 67.5 [C$_5$H$_5$], 70.9 [C$_5$H$_4$], 73.0 [C$_5$H$_4$]
$^{11}$B NMR (96 MHz, CDCl$_3$) δ 30.1.
IR (KBr disk, cm$^{-1}$), v2930 md, 1501 md, 1482 s, 1382 s, 1324 s, 1261 md, 1189 w, 1130 s, 1034 md, 909 w, 816 s, 702 w, 688 md, 598 w.
UV/Vis (chloroform): λ$_{max}$=472 nm, ε=134 mol$^{-1}$ cm$^{-1}$ dm$^3$.
MS (EI): M$^+$=364.1 (100%), exact mass (calc.) m/z 362.1292, (obs.) 364.1290.
Crystal data for 1$^{pin}$: C$_{20}$H$_{25}$BFeO$_2$, tetragonal, P__4$_2$, a=16.8050(16) Å, b=16.8050(16) Å, c=6.3272(4) Å, V=1786.9(3) Å$^3$, Z=4, D$_{calc}$=1.353 Mg/m$^3$, μ(MoKα)=0.852 mm$^{-1}$. A suitable crystal was covered in pre-dried mineral oil and mounted at 150(2) K. 3179 unique reflections were collected (3.6<θ<26.3°). Final R-factor: R$_1$=0.084.

Example 2

Preparation of 1$^e$ and 1$^{pr}$

1$^e$ and 1$^{pr}$ were synthesised via route 2 (Scheme 1). In this case, triethylamine (2 equiv.) was added to the diol precursor prior to the addition of dibromoborylferrocene (1 equiv.). 1$^e$ was isolated as orange crystals in 42% yield; single crystals were grown by slow evaporation of solvent from an acetonitrile solution in air. 1$^{pr}$ was isolated as a yellow-orange crystalline solid in 43% yield. Single crystals were obtained by cooling a concentrated hexanes solution to −30° C.

Spectroscopic and Crystallographic Data for 1$^e$:
$^1$H NMR ([D]chloroform, 21° C.), δ 4.08 [s, 5H, C$_5$H$_5$], 4.26 [s, 4H, CH$_2$ of chelate], 4.34 [m, 4H, C$_5$H$_4$].
$^{13}$C NMR ([D]chloroform, 21° C.): δ 65.7 [CH$_2$ of chelate], 68.5 [CH of C$_5$H$_5$], 72.2, 73.7 [CH of C$_5$H$_4$], C$_5$H$_4$ quaternary not observed.
$^{11}$B NMR ([D]chloroform, 21° C.): δ 32.7.
IR (KBr disk, cm$^{-1}$) 2973 w, 2911 w, 2360 w, 1497 md, 1473 md, 1312 st, 1384 md, 1184 w, 1129 st, 990 md, 504 md.
UV/Vis (chloroform): λ$_{max}$=444 nm, ε=135 cm$^{-1}$ mol$^{-1}$ dm$^3$.
MS(EI): M*=256 (100%), exact mass (calc.) m/z 256.0353, (obs.) 256.0352.
Crystal data for 1$^e$: C$_{12}$H$_{13}$BFeO$_2$, orthorhombic, P2$_1$2$_1$2$_1$, a=5.8179(1), b=9.9233(2), c=18.4741(5) Å, V=1066.56(4) Å$^3$, Z=4, D$_{calc}$=1.594 g cm$^{-3}$, μ(MoKα)=1.391 mm$^{-1}$. A suitable crystal was covered in pre-dried mineral oil and mounted at 150(2) K. 2138 unique reflections were collected (3.7<θ<26.4°). Final R-factor: R$_1$=0.033.

Spectroscopic and Crystallographic Data for $1^{pr}$:

$^1$H NMR ([D]chloroform, 20° C.), δ 2.05 [m, 2H, $CH_2CH_2CH_2$ of chelate], 4.12 [m, 4H, $CH_2CH_2CH_2$ of chelate], 4.13 [s, 5H, CH of $C_5H_5$], 4.33 [m, 2H, CH of $C_5H_4$], 4.34 [m, 2H, CH of $C_5H_4$].

$^{13}$C NMR ([D]chloroform, 20° C.), δ 27.4 [$CH_2CH_2CH_2$ of chelate], 62.0 [$CH_2CH_2CH_2$ of chelate], 68.4 [CH of $C_5H_5$], 71.6 [CH of $C_5H_4$], 73.0 [CH of $C_5H_4$], quaternary of $C_5H_4$ not observed.

$^{11}$B NMR ([D]chloroform, 20° C.), δ 28.6.

IR (KBr disk, cm$^{-1}$), ν3154 w, 2962 w, 2253 st, 1793 w, 1638 w, 1560 w, 1466 md, 1379 md, 1296 md, 1261 st, 1166 md, 1095 st, 1016 st, 913 st, 716 st.

UV/Vis (chloroform): $\lambda_{max}$ (ε) 446 nm, ε=133 cm$^{-1}$ mol$^{-1}$ dm$^3$. MS(EI): M$^+$=270 (100%), exact mass (calc.) m/z 270.0509, (obs.) 270.0506.

Crystal data for $1^{pr}$: $C_{13}H_{15}BFeO_2$, orthorhombic, Pbn2$_1$, a=5.8359(3), b=13.8400(7), c=14.7344(8) Å, V=1190.08(11) Å$^3$, Z=4, $D_{calc}$=1.506 g cm$^{-3}$, μ(MoKα)=1.250 mm$^{-1}$. A suitable crystal was covered in pre-dried mineral oil and mounted at 150(2) K. 2299 unique reflections were collected (3.8<θ<26.4°). Final R-factor: $R_1$=0.041.

Example 3

Preparation of $1^{pip}$ and $1^m$ $1^{pip}$ and $1^m$ were synthesised via route 4 (Scheme 1). $1^{pip}$ was obtained as a crystalline orange solid in 53% yield; crystals suitable for X-ray diffraction were obtained by slow evaporation of solvent from a chloroform solution. $1^m$ was obtained as an orange crystalline solid in 57% yield; single crystals were obtained by slow evaporation of solvent from a hexane solution.

Spectroscopic and Crystallographic Data for $1^{pip}$:

$^1$H NMR ([D]chloroform, 20° C.), δ 1.30 (m, 4H, γ $CH_2$ of pip), 1.45 (m, 8H, β $CH_2$ of pip), 2.30 (m, 8H, α $CH_2$ of pip), 2.35-2.65 (overlapping m, 6H, CHO, $CH_2$N), 4.05 (s, 5H, $C_5H_5$), 4.20-4.30 (m, 2H, $C_5H_4$), 4.35 (m, 2H, $C_5H_4$).

$^{13}$C NMR ([D]chloroform, 20° C.), δ 24.3 (γ $CH_2$ of pip), 26.1 (β $CH_2$ of pip), 55.5 (α $CH_2$ of pip), 64.0 ($CH_2$N), 68.6 ($C_5H_5$), 72.1 (CHO), 73.7 (quaternary of $C_5H_4$), 77.4 (CH of $C_5H_4$) and 79.3 (CH of $C_5H_4$).

$^{11}$B NMR ([D]chloroform, 20° C.), δ 32.4.

IR (KBr disk, cm$^{-1}$), ν2933 st, 2803 md, 1483 st, 1381 md, 1321 st, 1215 md, 1182 md, 1159 md, 1127 st, 981 st, 863 md, 819 md, 791 w, 769 w, 687 md and 500 st UV/Vis (chloroform): $\lambda_{max}$=440 nm, ε=111 cm$^{-1}$ mol$^{-1}$ dm$^3$.

MS(EI): M$^+$=451 (100%), exact mass (calc.) m/z 451.2219, (obs.) 451.2229.

Crystal data for $1^{pip}$: $C_{24}H_{35}BFeN_2O_2$, triclinic, P-1, a=11.303(2), b=17.359(4), c=18.418(4) Å, α=76.60(3), β=79.68(3), γ=89.86(3)°, V=3445.7(12) Å$^3$, Z=6, $D_{calc}$=1.298 g cm$^{-3}$, μ(MoKα)=0.677 mm$^{-1}$. A suitable crystal was covered in pre-dried mineral oil and mounted at 150(2) K. 13325 unique reflections were collected (2.92<θ<26.0°). Final R-factor: $R_1$=0.041.

Spectroscopic and Crystallographic Data for $1^m$:

$^1$H NMR ([D]chloroform, 20° C.), δ 2.35-2.50 (m, 8H, $CH_2$N of morph), 2.50-2.65 (m, 8H, $CH_2$O of morph), 3.60 (overlapping m, 6H, CHO, $CH_2$N), 4.05 (s, 5H, $C_5H_5$), 4.35 (overlapping m, 4H, $C_5H_4$).

$^{13}$C NMR ([D]chloroform, 20° C.), δ 53.5 ($CH_2$N of morph), 62.3 ($CH_2$N), 65.9 ($CH_2$O of morph), 67.5 ($C_5H_5$), 71.2 (CHO), 72.6 (quaternary of $C_5H_4$), 72.9 (CH of $C_5H_4$), 77.8 (CH of $C_5H_4$).

$^{11}$NMR ([D]chloroform, 20° C.), δ 32.7.

IR (KBr disk, cm$^{-1}$), ν2965 st, 2852 st, 2813 st, 1486 st, 1456 st, 1383 st, 1321 st, 1268 md, 1114 st, 1065 md, 986 st, 908 w, 867 md, 822 md, 766 w, 685 md, 514 md and 478 md.

UV/Vis (chloroform): $\lambda_{max}$=442 nm, ε=97 cm$^{-1}$ mol$^{-1}$ dm$^3$.

MS(EI): M$^+$=454.2 (weak), exact mass (calc.) m/z 454.1721, (obs.) 454.1721.

Crystal data for $1^m$: $C_{22}H_{31}BFeN_2O_4$, monoclinic, P2$_1$/c, a=16.628(3), b=13.611(3), c=9.940(2) Å, β=97.46(3)°, V=2230.6(8) Å$^3$, Z=4, $D_{calc}$=1.352 g cm$^{-3}$, μ(MoKα)=0.706 mm$^{-1}$. A suitable crystal was covered in pre-dried mineral oil and mounted at 150(2) K. 4371 unique reflections were collected (2.95<θ<26.0°). Final R-factor: $R_1$=0.035.

Example 4

Preparation of $1^{bn}$ $1^{bn}$ was synthesised via route 3 (Scheme 1). In this case $(Me_3SiOCH_2CH_2)_2NMe$ (1 equiv.) in toluene (50 cm$^3$) was added to a solution of dibromoborylferrocene at room temperature and the reaction mixture stirred for 24 h. $1^{bn}$ was isolated as an orange crystalline solid in 68% yield following recrystallization from toluene at −30° C. Single crystals were obtained by hexane diffusion into a concentrated toluene solution.

Spectroscopic and Crystallographic Data for $1^{bn}$:

$^1$H NMR ([D$_6$]benzene, 300 MHz, 20° C.), δ 1.59 [s, 3H, $CH_3$], 1.92 [br, m, 4H, $CH_2$], 3.64 [m, 2H, $CH_2$], 3.73 [m, 2H, $CH_2$], 4.34 [m, 2H, $C_5H_4$], 4.39 [m, 2H, $C_5H_4$], 4.47 [s, 5H, $C_5H_5$].

$^{13}$C NMR ([D$_6$]benzene, 76 MHz, 20° C.), δ 46.4 [$CH_3$], 59.9 [$CH_2$], 61.7 [$CH_2$], 68.9 [CH of $C_5H_5$], 69.7 [CH of $C_5H_4$], 72.6 [CH of $C_5H_4$].

$^{11}$B NMR ([D$_6$]benzene, 96 MHz, 20° C.), δ 13.4 (br).

IR (KBr disk, cm$^{-1}$), 2870 md, 1453 md, 1636 w, 1453 md, 1368 w, 1239 md, 1225 st, 1106 st, 1078 st, 999 st, 912 md, 852 md, 817 st, 724 md.

UV/Vis (chloroform): $\lambda_{max}$ (ε) 444 nm, ε=123.5 mol$^{-1}$ cm$^{-1}$ dm$^3$.

MS(EI): M$^+$=313 (80%), exact mass (calc.) 313.0931, (obs) 313.0932.

Crystal data for $1^{bn}$: $C_{15}H_{20}BFeNO_2$, orthorhombic, Pnma, a=12.522(3), b=10.602(2), C=10.421(2) Å, V=1383.5(5) Å$^3$, Z=4, $D_{calc}$=1.503 g cm$^{-3}$, μ(MoKα)=1.089 mm$^{-1}$. A suitable crystal was covered in pre-dried mineral oil and mounted at 150(2) K. 1667 unique reflections were collected (3.2<θ<27.5°). Final R-factor: $R_1$=0.034.

Example 5

Preparation of $2^s$, $2^c$, $2^{bc}$, $2^{mc}$ and $2^n$

Bifunctional systems $2^s$, $2^c$, $2^{bc}$, $2^{mc}$ and $2^n$ were synthesised from 1,1'-bis(dibromoboryl)ferrocene via route 1 in a manner analogous to that described above for mono-functional Lewis acids. However, in this case the diol dilithiate and 1,1'-bis(dibromoboryl)ferrocene were reacted in a 2:1 stoichiometry. In the case of $2^n$, THF was added to the solvent system to aid diol solubility. $2^s$ (homochiral samples containing wholly R,R,R,R or S,S,S,S isomers) was isolated in 45% yield as air-stable orange crystalline solids. Cooling a solution of $2^s$ in a 1:6 mixture of benzene and petroleum ether (40/60) to −30° C. yielded single crystals of the bis(benzene) solvate [$2^s$.2($C_6H_6$)] suitable for X-ray diffraction. Single crystals were also grown in the absence of benzene, by slow evaporation of solvent from a concentrated 40/60 petroleum ether solution (to yield the unsolvated compound).

Compound $2^c$ was isolated in 26% yield as an air sensitive orange crystalline solid after recrystallization from hexane.

$2^{bc}$ was isolated as a moderately air sensitive orange solid in 29% yield after recrystallization from hexane.

$2^{mc}$ was isolated in 19% yield as a slightly air sensitive reddish-orange solid after recrystallization from hexane.

$2^n$ was isolated as a yellow-orange air-stable crystalline solid in 26% yield after recrystallization from warm hexane (sparingly soluble).

$2^n$ can also be prepared from 1,1'-ferrocenediboronic acid via route 4: the boronic acid (1 g, 3.66 mmol) and (S)-1-napthyl-ethane-1,2-diol (1.38 g, 7.31 mmol) were dissolved in acetone in a sealed high pressure tube. The mixture was stirred for 96 h at 75° C., solvent removed in vacuo and the product purified by column chromatography (silica column, elution with chloroform). This method yielded samples of $2^n$ with identical spectroscopic properties to those synthesised via route 1. The yield of 18% appears to be limited by the low purity of commercially available 1,1'-ferrocenediboronic acid.

Spectroscopic and Crystallographic Data for $2^s$:

$^1$H NMR ([D$_6$]benzene, 20° C.), δ 4.39 [m, 2H, C$_5$H$_4$], 4.44 [m, 2H, C$_5$H$_4$], 4.88 [m, 2H, C$_5$H$_4$], 4.99 [m, 2H, C$_5$H$_4$], 5.30 [s, 4H, CH of chelate], 7.04-7.26 [m, 20H, C$_6$H$_5$].

$^1$H NMR ([D]chloroform, 20° C.), δ 4.55 [m, 2H, C$_5$H$_4$], 4.61 [m, 2H, C$_5$H$_4$], 4.71 [m, 4H, C$_5$H$_4$], 5.28 [s, 4H, CH of chelate], 7.37 [m, 20H, C$_6$H$_5$].

$^{13}$C NMR ([D]chloroform, 20° C.), δ 72.9, 73.5, 75.1, 75.5 [CH of C$_5$H$_4$], 86.9 [CH of chelate], 126.2, 128.4, 128.8 [aromatic CH], 140.1 [aromatic quaternary].

$^{11}$B NMR ([D]chloroform, 20° C.), δ 34.0.

IR (KBr disk, cm$^{-1}$), ν=3030 w, 2912 w, 1482 st, 1455 md, 1382 st, 1328 st, 1301 md, 1215 w, 1177 md, 1027 w, 980 md, 762 md, 700 st, 682 st.

UV/Vis (chloroform): $\lambda_{max}$ 450 nm, ε=209 cm$^{-1}$ mol$^{-1}$ dm$^3$.

MS(EI): M$^+$=630 (100%), exact mass (calc.) m/z 630.1836, (obs.) 630.1834.

Elemental analysis: calcd (%) for C$_{38}$H$_{32}$B$_2$FeO$_4$: C, 72.43, H, 5.08; found: C, 72.61, H, 5.13%. Crystal data for $2^s$.2(C$_6$H$_6$):
C$_{38}$H$_{32}$B$_2$FeO$_4$.2C$_6$H$_6$, tetragonal, P4$_1$, a=11.1199(3), b=11.1199(3), c=33.3350(12) Å, V=4121.9(2) Å$^3$, Z=4, D$_{calc}$=1.267 g cm$^{-3}$, μ(MoKα)=0.411 mm$^{-1}$. A suitable crystal was covered in pre-dried mineral oil and mounted at 150(2) K. 5589 unique reflections were collected (3.1<θ<26.0°). Final R-factor: R$_1$=0.046.

Crystal data for $2^s$: C$_{38}$H$_{32}$B$_2$FeO$_4$, orthorhombic, P2$_1$2$_1$2$_1$, a=10.656(2), b=15.002(3), C=19.920(4) Å, V=3184.4(11) Å$^3$, Z=4, D$_{calc}$=1.314 g cm$^{-3}$, μ(MoKα)= 0.514 mm$^{-1}$. A suitable crystal was covered in pre-dried mineral oil and mounted at 150(2) K. 7212 unique reflections were collected (3.1<θ<27.5°). Final R-factor: R$_1$=0.041.

Spectroscopic Data for $2^c$:

$^1$H NMR ([D$_6$]benzene, 20° C.), δ 4.13 [m, 4H, C$_5$H$_4$], 4.67 [m, 4H, C$_5$H$_4$], 6.77-6.96 [m, 8H, C$_6$H$_4$].

$^1$H NMR ([D]chloroform, 20° C.), δ 4.53 [m, 4H, C$_5$H$_4$], 4.68 [m, 4H, C$_5$H$_4$], 7.04-7.11 [m, 8H, C$_6$H$_4$].

$^{13}$C NMR ([D$_6$]benzene, 20° C.), δ 73.5, 74.6 [CH of C$_5$H$_4$], 112.3, 122.4 [aromatic CH], 148.8 [aromatic quaternary].

$^{11}$B NMR ([D$_6$]benzene, 20° C.), δ 34.0.

IR (KBr disk, cm$^{-1}$), ν3313 md, 1501 md, 1470 st, 1383 md, 1316 st, 1239 st, 1106 md, 896 w, 737 md, 681 w.

UV/Vis (chloroform): $\lambda_{max}$ (ε) 441 nm.

MS(EI): M$^+$=422 (100%), exact mass (calc.) m/z 422.0579, (obs.) 422.0575.

Spectroscopic Data for $2^{bc}$:

$^1$H NMR ([D$_6$]benzene, 20° C.), δ 1.31 [s, 18H, $^t$Bu], 1.57 [s, 18H, $^t$Bu], 4.23 [m, 4H, C$_5$H$_4$], 4.68 [m, 4H, C$_5$H$_4$], 7.22-7.28 [m, 4H, C$_6$H$_2$].

$^1$H NMR ([D]chloroform, 20° C.), δ 1.37 [s, 18H, $^t$Bu], 1.49 [s, 18H, $^t$Bu], 4.47 [m, 4H, C$_5$H$_4$], 4.66 [m, 4H, C$_5$H$_4$], 7.06-7.17 [m, 4H, C$_6$H$_2$].

$^{13}$C NMR ([D$_6$]benzene, 20° C.), δ 29.8, 31.7, 34.4, 34.8 [aliphatic tert-butyl], 73.5, 74.6 [CH of C$_5$H$_4$], 107.9, 116.2 [aromatic CH], 134.6, 144.6, 145.5, 149.1 [aromatic quaternary].

$^{11}$B NMR ([D$_6$]benzene, 20° C.), δ 34.0.

IR (KBr disk, cm$^{-1}$), ν=2954 st, 2868 md, 1628 w, 1602 w, 1484 st, 1413 st, 1382 st, 1314 st, 1263 st, 1241 st, 1198 md, 1118 st, 1026 st, 977 st, 893 md, 858 md, 815 md, 693 md.

UV/Vis (chloroform): $\lambda_{max}$=444 nm.

MS(EI): M$^+$=646 (48%), exact mass (calc.) m/z 646.3088, (obs.) 646.3094.

Spectroscopic Data for $2^{mc}$:

$^1$H NMR ([D$_6$]benzene, 20° C.), δ 3.47 [s, 6H, OCH$_3$], 4.10 [m, 4H, C$_5$H$_4$], 4.64 [m, 4H, C$_5$H$_4$], 6.37-6.39 [m, 2H, C$_6$H$_3$], 6.76-6.78 [m, 4H, C$_6$H$_3$].

$^1$NMR ([D]chloroform, 20° C.), δ 3.97 [s, 6H, OCH$_3$], 4.51 [m, 4H, C$_5$H$_4$], 4.73 [m, 4H, C$_5$H$_4$], 6.65-6.69 [m, 2H, C$_6$H$_3$], 6.77-6.80 [m, 2H, C$_6$H$_3$], 6.96-6.99 [m, 2H, C$_6$H$_3$].

$^{13}$C NMR ([D$_6$]benzene, 20° C.), δ 55.8 [OCH$_3$], 73.5, 74.6 [CH of C$_5$H$_4$], 105.4, 107.6, 122.5 [aromatic CH], 146.1, 150.4 [aromatic quaternary].

$^{11}$B NMR ([D$_6$]benzene, 20° C.), δ 34.0.

IR (KBr disk, cm$^{-1}$), ν3093 md, 2996 md, 2960 md, 2832 w, 1634 st, 1506 st, 1449 st, 1316 st, 1075 st, 1029 md, 896 md, 819 w, 763 md, 722 md, 686 md, 522 w, 487 w.

UV/Vis (chloroform): $\lambda_{max}$ (ε) 449 nm.

MS(EI): M$^+$=482 (34%), exact mass (calc.) m/z 482.0795, (obs.) 482.0802.

Spectroscopic Data for $2^n$:

$^1$H NMR ([D$_6$]benzene, 20° C.), δ 3.96 [m, 1H, CH$_2$ of chelate], 4.27 [m, 1H, CH$_2$ of chelate], 4.40 [m, 4H, C$_5$H$_4$], 4.87 [m, 4H, C$_5$H$_4$], 5.38 [m, 1H, CH of chelate], 7.23-7.26 [m, 6H, C$_{10}$H$_7$], 7.58-7.74 [m, 8H, C$_{10}$H$_7$].

$^1$H NMR ([D]chloroform, 20° C.), δ 4.22 [m, 2H, CH$_2$ of chelate], 4.51 [m, 4H, C$_5$H$_4$], 4.59 [m, 4H, C$_5$H$_4$], 4.76 [m, 2H, CH$_2$ of chelate]5.70 [m, 2H, CH of chelate], 7.46-7.49 [m, 6H, C$_{10}$H$_7$], 7.81-7.88 [m, 8H, C$_{10}$H$_7$].

$^{13}$C NMR ([D$_6$]benzene, 20° C.), δ 72.9 [CH of C$_5$H$_4$], 73.2 [CH$_2$ of chelate], 75.0 [CH of C$_5$H$_4$], 75.3 [CH of C$_5$H$_4$], 78.9 [CH of chelate], 123.6, 125.0, 126.0, 126.3, 128.7 [aromatic CH], 133.4, 133.5, 138.9 [aromatic quaternary].

$^{11}$B NMR ([D$_6$]benzene, 20° C.), δ 33.2.

IR (KBr disk, cm$^{-1}$), ν2956 w, 2895 w, 1579 w, 1488 st, 1473 st, 1378 md, 1322 md, 1292 w, 1132 st, 1046 w, 996 w, 825 w.

UV/Vis (chloroform): $\lambda_{max}$ (ε) 447 nm.

MS(EI): M$^+$=578 (18%), exact mass (calc.) m/z 578.1518, (obs.) 578.1521.

Example 6

Preparation of $2^e$, $2^{pin}$ and $2^{ca}$ $2^e$, $2^{pin}$ and $2^{ca}$ were synthesised via route 2 (scheme 1). Triethylamine (2 equiv.) was added to the diol precursor prior to the addition of 1,1'-bis(dibromoboryl)ferrocene. $2^{pin}$ was recrystallised from hexanes as an orange crystalline solid in 46% yield. Single crystals suitable for X-ray diffraction were isolated from a hexane solution cooled to −30° C.

$2^e$ was isolated in 47% yield as an orange crystalline solid after recrystallization from hexane solution. Crystals suitable for X-ray diffraction were isolated from a hexane solution cooled to −30° C.

$2^{ca}$ was isolated as an orange crystalline material in 40% isolated yield. Single crystals (of the hexane hemi-solvate) suitable for X-ray diffraction were grown by slow evaporation of solvent from a hexanes solution in air.

Spectroscopic and Crystallographic Data for $2^e$:
$^1$H NMR ([D]chloroform, 21° C.): δ 4.31 [s, 8H, CH$_2$ of chelate], 4.39 [m, 4H, C$_5$H$_4$], 4.40 [m, 4H, C$_5$H$_4$].
$^{13}$C NMR ([D]chloroform, 21° C.): δ 65.8 [CH$_2$ of chelate], 72.7, 74.6 [CH of C$_5$H$_4$, C$_5$H$_4$ quaternary not observed.
$^{11}$B NMR ([D]chloroform, 21° C.): δ 32.6.
IR (KBr disk, cm$^{-1}$), 2973 md, 2909 md, 1653 w, 1559 w, 1507 st, 1496 st, 1473 st, 1420 w, 1381 md, 1312 st, 1261 w, 1227 md, 1188 w, 1128 st, 1031 st, 982 st, 935 md, 822 md, 582 w, 492 md.
UV/Vis (chloroform): $\lambda_{max}$=448 nm, ϵ=213 cm$^{-1}$ mol$^{-1}$ dm$^3$.
MS(EI): M$^+$=326 (100%), exact mass (calc.) m/z 326.0579, (obs.) 326.0580.
Crystal data for $2^e$: C$_{14}$H$_{16}$B$_2$FeO$_4$, monoclinic, C2/m, a=7.0116(4), b=10.0523(7), c=9.8912(7) Å, β=104.211(3)°, V=675.82(8) Å$^3$, Z=2, D$_{calc}$=1.601 g cm$^{-3}$, μ(MoKα)=1.126 mm$^{-1}$. A suitable crystal was covered in pre-dried mineral oil and mounted at 150(2) K. 740 unique reflections were collected (3.6<θ<26.3°). Final R-factor: R$_1$=0.045.

Spectroscopic and Crystallographic Data for $2^{pin}$:
$^1$H NMR ([D]chloroform, 20° C.): δ 0.83 [s, 6H, H-8], 1.25 [s, 6H, H-9], 1.28 [d J=10 Hz, 2H, H-6a], 1.42 [s, 6H H-10], 1.89 [overlapping m, 4H, H-2, H-4a, H-5, H-7], 2.07 [t J=5 Hz, 2H, H-1], 2.21 [m, 2H, H-6b], 2.35 [2H, m, H-4b], 4.32 [m, 4H, CH of C$_5$H$_4$], 4.34 [m, 2H, H-3], 4.35 [m, 2H, CH of C$_5$H$_4$], 4.37 [m, 2H, CH of C$_5$H$_4$].
$^{13}$C NMR ([D]chloroform, 20° C.): δ 24.2, 26.7, 27.2, 29.1, 35.9, 38.3, 39.7, 51.4, 77.9, 85.8 [pinane backbone], 72.5, 72.6, 74.2, 74.3 [CH of C$_5$H$_4$].
$^{11}$B NMR ([D]chloroform, 20° C.), δ 32.2.
IR (KBr disk, cm$^{-1}$), ν=3155 w, 2924 st, 2253 st, 1794 w, 1647 w, 1560 w, 1480 st, 1383 st, 1323 st, 1312 st, 1277 md, 1261 md, 1237 md, 1209 w, 1189 w, 1128 st, 1096 md, 1021 md, 916 st, 712 st.
UV/Vis (chloroform): $\lambda_{max}$=462 nm, ϵ=101 cm$^{-1}$ mol$^{-1}$ dm$^3$.
MS(EI): M$^+$=542 (100%), exact mass (calc.) m/z 542.2457, (obs.) 542.2456.
Crystal data for $2^{pin}$: C$_{30}$H$_{40}$B$_2$FeO$_4$, monoclinic, P2$_1$, a=10.0381(3), b=7.4076(3), c=18.2949(7) Å, β=92.140(2)°, V=1359.43(9) Å$^3$, Z=2, D$_{calc}$=1.324 g cm$^{-3}$, μ(MoKα)= 0.589 mm$^{-1}$. A suitable crystal was covered in pre-dried mineral oil and mounted at 150(2) K. 5346' unique reflections were collected (3.0<θ<27.5°). Final R-factor: R$_1$=0.056.

Spectroscopic and Crystallographic Data for $2^{ca}$:
$^1$H NMR ([D]chloroform, 21° C.): δ 1.17 [s, 36H, $^t$Bu], 3.34 [d, $^2$J$_{HH}$=13 Hz, 2H, CH$_2$ of calixarene], 3.39 [d, $^2$J$_{HH}$=14 Hz, 2H, CH$_2$ of calixarene], 4.03 [d, $^2$J$_{HH}$=14 Hz, 2H, CH$_2$ of calixarene], 4.43 [m, 4H, CH of C$_5$H$_4$], 4.68 [m, 4H, CH of C$_5$H$_4$], 4.83 [d, $^2$J$_{HH}$=13 Hz, 2H, CH$_2$ of calixarene], 6.88 [m, 4H, aromatic CH], 7.19 [m, 4H, aromatic CH].
$^{13}$C NMR ([D]chloroform, 21° C.): δ 30.4 [CH$_3$ of $^t$Bu], 30.5 [CH$_2$ of calixarene], 33.0 [quaternary of $^t$Bu], 33.1 [CH$_2$ of calixarene], 71.7, 73.6 [CH of C$_5$H$_4$], 123.3, 124.3 [aromatic CH], 127.3, 130.1, 143.8, 146.9 [aromatic quaternary].
$^{11}$B NMR ([D]chloroform, 21° C.): δ 27.8 (v br). IR (KBr disk, cm$^{-3}$): 2965 st, 1483 md, 1468 md, 1378 w, 1327 md, 1262 st, 1212 w, 1096 st, 1021 st, 871 w, 801 st, 695 w.
UV/Vis (chloroform): $\lambda_{max}$=460 nm, ϵ=375 cm$^{-1}$ mol$^{-1}$ dm$^3$.
MS(EI): M$^+$=850 (60%), exact mass (calc.) m/z 850.4022, (obs.) 850.4026.

Example 7

Preparation of $3^s$ and $3^{pin}$

Trifunctional systems $3^s$ and $3^{pin}$ were synthesised from 1-ethyl-1',3,3'-tris(dibromoboryl)ferrocene via route 1 (Scheme 1). In this case, n-butyllithium (6 equiv.) was added to the diol precursor (3 equiv.) prior to the addition of 1-ethyl-1',3,3'-tris(dibromoboryl)ferrocene (1 equiv.). $3^s$ was isolated in 46% yield as an air-stable, orange, crystalline solid.

Single crystals were obtained from an acetonitrile/water layering at room temperature.

Compound $3^{pin}$ was isolated in 38% yield as an air-stable orange solid.

Spectroscopic and Crystallographic Data for $3^s$:
$^1$H NMR ([D]chloroform, 20° C.): δ 1.08 [t J=Hz, 3H, CH$_3$ of Et], 2.38 [m, 2H, CH$_2$ of Et], 4.47, 4.50, 4.55, 4.63, 4.85, 5.01 [s, each 1H, CH of chelate], 5.13 [m, 2H, C$_5$H$_3$], 5.14 [m, 2H, C$_5$H$_3$], 5.22 [s, 1H, C$_5$H$_3$], 5.25[s, 1H, C$_5$H$_3$], 7.25-7.67 [m, 30H, aromatic CH].
$^{13}$C NMR ([D]chloroform, 20° C.): δ 14.0, 21.1 [Et], 72.6, 73.6, 74.1, 77.7, 78.5, 81.0 [CH of C$_5$H$_3$], 85.6 (three closely spaced resonances at 85.57, 85.59, 85.62) [CH of chelate], 125.0, 125.2, 125.3, 127.0, 127.1, 127.2, 127.5, 127.6, 127.7, 138.7, 138.8, 139.3 [C$_6$H$_5$].
$^1$B NMR (96 MHz, CDCl$_3$): δ 34.1.
IR (KBr disk, cm$^{-1}$) ν 2923 s, 1463 s, 1376 s, 1274 s, 1209 md, 1078 w, 1059 md, 986 md, 844 w, 759 md, 697 s, 650 w, 611 w.
UV/Vis (chloroform): $\lambda_{max}$=454 nm, ϵ=253 mol$^{-1}$ cm$^{-1}$ dm$^3$.
MS (EI): M$^+$=880 (100%), exact mass (calc.) m/z 880.2996, (obs.) 880.2997.
Crystal data for $3^s$: C$_{54}$H$_{47}$B$_3$FeO$_6$, orthorhombic, P 2$_1$2$_1$2$_1$, a=9.26740(10) Å, b=15.9758(2) Å, c=30.0231(4) Å, v=4445.04(9) Å$^3$, Z=4, D$_{calc}$=1.315 Mg/m$^3$, μ(MoKα)= 0.392 mm$^{-1}$. A suitable crystal was covered in pre-dried mineral oil and mounted at 150(2) K. 8873 unique reflections were collected (3.6≤θ<26.3°). Final R-factor: R$_1$=0.071.

Spectroscopic Data for $3^{pin}$:
$^1$H NMR ([D]chloroform, 20° C.): δ 0.82 [s, 9H, C-10], 1.09 [t J=5 Hz, 3H, CH$_3$ of Et], 1.24 [s, 9H, C-9], 1.20 [m, 3H], 1.41 [overlapping singlets, 9H, C-8], 1.87 [m, 6H], 2.04 [m, 3H], 2.31 [m, 3H], 2.33 [m, 5H], 4.15-4.52 (overlapping m, 9H, C$_5$H$_3$ and H-3].
$^{13}$C NMR ([D]chloroform, 20° C.): δ 12.9, 21.9 [Et], 24.1, 26.7 (three overlapping signals), 27.2, 29.0, 35.7 (three overlapping signals), 38.2, 39.7, 51.4 (three overlapping signals), 77.8 (three overlapping signals), 85.6 (three overlapping signals) [pinane backbones], 73.4, 77.4, 77.7, 78.2, 81.9, 82.5 [CH of C$_5$H$_3$].
$^{11}$B NMR (96 MHz, CDCl$_3$) δ 32.8.
IR (KBr disk, cm$^{-1}$): ν 2923 s, 1716 w, 1462 s, 1375 s, 1304 md, 1233 md, 1122 md, 1078 md, 1061 w, 1025 w, 989 w, 937 w, 722 md.
UV/Vis (chloroform): $\lambda_{max}$=454 nm, ϵ=218 mol$^{-1}$ cm$^{-1}$ dm$^3$.
MS (EI): M$^+$=754 (100%), exact mass (calc.) m/z 754.4044, (obs.) 754. 4045.

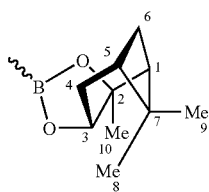

Preparation of 3$^e$:

3$^e$ was synthesised from 1-ethyl-1',3,3'-tris(dibromoboryl)ferrocene via route 2 (Scheme 1). In this case, triethylamine (6 equiv.) was added to the diol precursor (3 equiv.) prior to the addition of 1-ethyl-1',3,3'-tris(dibromoboryl)ferrocene (1 equiv.). 3$^e$ was isolated in 41% yield as air-stable, orange-yellow solid.

Spectroscopic Data for 3$^e$:

$^1$H NMR ([D]chloroform, 20° C.): δ 0.91 [t J=7 Hz, 3H, CH$_3$ of Et], 2.26 [m, 2H, CH$_2$ of Et], 4.22 [m, 2H, C$_5$H$_3$] 4.24 [s, 1H, C$_5$H$_3$], 4.26 [s, 12H, CH$_2$CH$_2$ of chelate], 4.45 [m, 1H, C$_5$H$_3$], 4.51 [m, 2H, C$_5$H$_3$].

$^{13}$C NMR ([D]chloroform, 20° C.): δ 14.6, 21.7 [Et], 65.7 [CH$_2$ of chelate], 72.7, 74.4, 78.4, 78.6, 81.7, 96.3 [CH of C$_5$H$_3$].

$^{11}$B NMR (96 MHz, CDCl$_3$): δ 32.6.

IR (KBr disk, cm$^{-1}$): ν 2924 s, 1460 s, 1376 s, 1298 md, 1198 md, 1084 w, 1064 md, 991 md, 42 md, 850 w, 722 md, 686 w.

UV/Vis (chloroform): λ$_{max}$=454 nm, ε=199 mol$^{-1}$ cm$^{-1}$ dm$^3$.

MS (EI): M$^+$=424 (100%), exact mass (calc.) m/z 424.1118, (obs.) 424.1119.

Example 8

Preparation of 4$^s$, 4$^{pin}$ and 4$^n$

Tetrafunctional systems 4$^d$, 4$^{pin}$ and 4$^n$ were synthesised from 1,1',3,3'-tetrakis-dibromoborylferrocene via route 1 (Scheme 1). In this case, n-butyllithium (8 equiv.) was added to the diol precursor (4 equiv.) prior to the addition of 1,1',3,3'-tetrakis-dibromoborylferrocene (1 equiv.).

4$^s$ was isolated in 38% yield as an air-stable orange crystalline solid. Single crystals were obtained from a toluene/hexane layering at −30° C.

4$^{pin}$ was isolated in 47% as an air-stable orange crystalline solid. Single crystals were grown by very slow cooling of an acetonitrile solution from 40° C. to room temperature.

4$^n$ was isolated in 50% yield as an air-stable orange solid after recrystallization from hexane.

Spectroscopic and Crystallographic Data for 4$^s$:

$^1$H NMR ([D$_6$]benzene, 20° C.): δ 5.33 [m, 4H, C$_5$H$_3$], 5.49 [s, 8H, CH of chelate], 5.86 [s, 2H, C$_5$H$_3$], 7.32-7.81 [m, 40H, aromatic CH].

$^{13}$C NMR ([D$_6$]benzene, 20° C.): δ 80.3, 80.7, 82.7 [C$_5$H$_3$], 87.2 [CH of chelate], 126.4, 126.8, 128.5, 140.0 [aromatic CH].

$^{11}$B NMR (96 MHz, C$_6$D$_6$): δ 33.2.

IR (KBr disk, cm$^{-1}$) ν 3033 w, 1605 w, 1496 s, 1276 s, 1213 md, 1192 md, 1146 w, 1061 s, 988 s, 802 w, 760 md, 698 s, 538 md.

UV/Vis (chloroform): λ$_{max}$=472 nm, ε=667 mol$^{-1}$ cm$^{-1}$ dm$^3$.

MS (EI): M$^+$=1074 (100%), exact mass (calc.) m/z 1074.3535, (obs.) 1074.3546.

Crystal data for 4$^s$: C$_{66}$H$_{54}$B$_4$FeO$_8$, orthorhombic, C, 2221, a=12.3580(2) Å, b=15.4190(2) Å, c=29.7570(5) Å, V=5670.14(15) Å$^3$, Z=4, D$_{calc}$=1.258 Mg/m$^3$, μ(MoKα)= 0.322 mm$^{-1}$. A suitable crystal was covered in pre-dried mineral oil and mounted at 150(2) K. 5619 unique reflections were collected (3.6<θ<26.3°). Final R-factor: R$_1$=0.051.

Spectroscopic and Crystallographic Data for 4$^{pin}$:

$^1$H NMR ([D]chloroform, 20° C.): δ 0.80 [s, 12H, H-10], 1.24 [s, 12H, H-9], 1.42 [s, 12H, H-8], 1.88 [overlapping m, 12H], 2.02 [t J=5 Hz, 4H], 2.16 [m, 4H], 2.29 [m, 4H], 4.30 [t J=7 Hz, 4H, H-3], 4.50 [m, 4H, C$_5$H$_3$], 4.56 [m, 2H, C$_5$H$_3$].

$^{13}$C NMR ([D]chloroform, 20° C.): δ 23.8, 26.9, 29.1, 35.8, 37.9, 39.7, 51.6, 51.7, 81.8, 85.6 [pinane backbone], 78.0 [C$_5$H$_5$], 78.2 [C$_5$H$_3$], 79.0 [C$_5$H$_3$].

$^{11}$B NMR (96 MHz, CDCl$_3$) δ 32.3.

IR (KBr disk, cm$^{-1}$): ν 3434 w, 2913 s, 2868 md, 2358 w, 1491 s, 1397 md, 1305 s, 1224 md, 1148 w, 1062 s, 988 w, 922 md, 692 s, 539 md.

UV/Vis (chloroform): λ$_{max}$=472 nm, ε=203 mol$^{-1}$ cm$^{-1}$ dm$^3$.

MS (EI): M$^+$=898 (100%), exact mass (calc.) m/z 898.4787, (obs.) 898.4796.

Crystal data for 4$^{pin}$: C$_{50}$H$_{70}$B$_4$FeO$_8$, orthorhombic, P2$_1$2$_1$2$_1$, a=11.969(2) Å, b=11.964(2) Å, c=32.749(7) Å, V=4689.6(15) Å$^3$, Z=4, D$_{calc}$=1.272 Mg/m$^3$, μ(MoK═)= 0.375 mm$^{-1}$. A suitable crystal was covered in pre-dried mineral oil and mounted at 150(2) K. 5184 unique reflections were collected (3.8<θ<23.5°). Final R-factor: R$_1$=0.106.

Spectroscopic Data for 4$^n$:

$^1$H NMR ([D]chloroform, 20° C.): δ 4.13 [overlapping m, 4H, CH$_2$ of chelate], 4.42 [m, 2H, CH of chelate], 4.65 [m, 2H, CH of chelate], 4.74 [d, 2H, C$_5$H$_3$], 4.80 [d, 2H, C$_5$H$_3$], 4.95 [s, 2H, C$_5$H$_3$], 5.62 [t J=8 Hz, 2H, CH$_2$ of chelate], 5.69 [t J=8 Hz, 2H, CH$_2$ of chelate], 7.39 [m, 12H, aromatic CH], 7.74 [m, 16H, aromatic CH].

$^{13}$C NMR ([D]chloroform, 20° C.): δ 70.9 [C$_5$H$_3$], 71.0 [C$_5$H$_3$], 76.5 [CH$_2$ of chelate], 76.6 [CH$_2$ of chelate], 76.8 [CH of chelate], 77.1 [CH of chelate], 80.4 [C$_5$H$_3$], 121.0, 121.4, 122.7, 123.0, 124.2, 125.8, 126.1, 126.7, 126.8, 131.1, 131.2, 131.3, 136.0, 136.5 [aromatic napthyl CH].

$^{11}$B NMR (96 MHz, CDCl$_3$): δ 32.4.

IR (KBr disk, cm$^{-1}$): ν 2923 s, 1625 w, 1462 s, 1376 s, 1063 md, 855 w, 814 w, 722 md.

UV/Vis (chloroform): λ$_{max}$=461 nm, ε=347 mol$^{-1}$ cm$^{-1}$ dm$^3$.

MS (EI): M$^+$=970 (100%), exact mass (calc.) m/z 970.2909, (obs.) 970.2908.

Example 9

Preparation of 4$^e$:

4$^e$ was synthesised from 1,1',3,3'-tetrakis-dibromoborylferrocene via route 2 (Scheme 1). In this case, triethylamine (8 equiv.) was added to the diol precursor (4 equiv.) prior to the addition of 1,1',3,3'-tetrakis-dibromoborylferrocene (1 equiv.). 4$^e$ was isolated in 31% yield as an air-stable, orange solid. Single crystals were grown by very slow evaporation of solvent from a benzene solution.

Spectroscopic and Crystallographic Data for 4$^e$:

$^1$H NMR ([D]chloroform, 20° C.): δ 4.35 [s, 16H, CH of chelate], 4.53 [s, 4H, C$_5$H$_3$], 4.65 [s, 2H, C$_5$H$_3$].

$^{13}$C NMR ([D]chloroform, 20° C.): δ 64.8 [chelate], 77.7, 80.8 [C$_5$H$_3$], quaternaries of C$_5$H$_4$ not observed.

$^{11}$B NMR (96 MHz, CDCl$_3$): δ 32.3.

IR (KBr disk, cm$^{-1}$): ν 3404 md, 1495 s, 1398 md, 1340 md, 1300 s, 1262 md, 1199 s, 1068 s, 992 md, 943 md, 860 w, 802 md, 691 md, 583 w, 500w.

UV/Vis (chloroform): $\lambda_{max}$=442 nm, $\epsilon$=79 mol$^{-1}$ cm$^{-1}$ dm$^3$.

MS (EI): M$^+$=466 (100%), exact mass (calc.) m/z 466.1031, (obs.) 466.1029.

Crystal data for 4$^s$: C$_{18}$H$_{22}$B$_4$FeO$_8$, monoclinic, P2$_1$/n, a=5.8495(3) Å, b=9.8627(5) Å, c=17.0345(11) ↑1, β=96.899 (2)°, V=975.64(9) Å$^3$, Z=2, D$_{calc}$=1.584 Mg/m$^3$, μ(MoKα)= 0.819 mm$^{-1}$. A suitable crystal was covered in pre-dried mineral oil and mounted at 150(2) K. 1987 unique reflections were collected (3.6<θ<26.3°. Final R-factor: R$_1$=0.055.

Example 10

Preparation of 5$^{ca}$

5$^{ca}$ was synthesised via route 2. Triethylamine (4 equiv.) was added to the calix[4]arene precursor in toluene prior to the addition of dibromoborylferrocene (2 equiv.).

Recrystallisation from hexanes at −30° C. yielded 5$^{ca}$ as an orange crystalline solid in 61% isolated yield (ca. 25% as single crystals suitable for X-ray diffraction).

Spectroscopic and Crystallographic Data for 5$^{ca}$:

$^1$H NMR ([D$_6$]benzene, 21° C.): δ 1.12 [s, 36H, $^t$Bu], 3.37 [d, $^2J_{HH}$=12 Hz, 2H, CH$_2$ of calixarene], 3.51 [d, $^2J_{HH}$=12 Hz, 2H, CH$_2$ of calixarene], 3.94 [s, 10H, C$_5$H$_5$], 4.15 [m, 4H, C$_5$H$_4$], 4.63 [m, 4H, C$_5$H$_4$], 4.72 [d, $^2H_{HH}$=12 Hz, 2H, CH$_2$ of calixarene], 5.26 [d, $^2J_{HH}$=12 Hz, 2H, CH$_2$ of calixarene], 6.94 [m, 4H, aromatic CH], 7.22 [m, 4H, aromatic CH]. $^1$H NMR ([D]chloroform, 21° C.): δ 1.26 [s, 36H, $^t$Bu], 3.40 [d, $^2J_{HH}$=12 Hz, 2H, CH$_2$ of calixarene], 3.55 [d, $^2J_{HH}$=12 Hz, 2H, CH$_2$ of calixarene], 3.98 [s, 5H, C$_5$H$_5$], 4.08 [m, 4H, C$_5$H$_4$], 4.28 [m, 4H, C$_5$H$_4$], 4.54 [d, $^2J_{HH}$=14 Hz, 2H, CH$_2$ of calixarene], 4.85 [d, $^2J_{HH}$=13 Hz, 2H, CH$_2$ of calixarene], 6.97 [m, 4H, aromatic CH], 7.26 [m, 4H, aromatic CH].

$^{13}$C NMR ([D]chloroform, 21° C.): δ 30.1, 36.3 [CH$_2$ of calixarene], 31.6 [CH$_3$ of $^t$Bu], 34.2 [quaternary of $^t$Bu], 68.4 [CH of C$_5$H$_5$], 71.7, 74.7 [CH of C$_5$H$_4$], 124.4, 126.0 [aromatic CH], 128.2, 131.3, 144.7, 148.2 [aromatic quaternary].

$^{11}$B NMR ([D]chloroform, 21° C.): δ 28.2.

IR (KBr disk, cm$^{-1}$), 2955 st, 2886 w, 1483 md, 1463 st, 1378 md, 1363 md, 1322 st, 1212 w, 1137 w, 1105 w, 1091 w, 1025 w, 872 w, 816 w.

UV/Vis (chloroform): $\lambda_{max}$=458 nm, $\epsilon$=449 cm$^{-1}$ mol$^{-1}$ dm$^3$.

MS(EI): M$^+$=1036 (100%), exact mass (calc.) m/z 1036.4154, (obs.) 1036.4161.

Example 11

Preparation of 5$^{thb}$

5$^{thb}$ was synthesised via route 3 (scheme 1). A solution of 1,2,4,5-(Me$_3$SiO)$_4$C$_6$H$_2$ (1 equiv) in toluene was added to a solution of dibromoborylferrocene in toluene and the reaction mixture heated at 80° C. for 1 week. 5$^{thb}$ was obtained as a yellow-orange solid in ca. 19% yield after recrystallization from toluene at −30° C.

Spectroscopic and Crystallographic Data for 5$^{tthb}$:

$^1$H NMR ([D$_6$]benzene, 20° C.): δ 6 3.93 [s, 10H, C$_5$H$_5$], 4.23 [m, 4H, C$_5$H$_4$], 4.71 [m, 4H, C$_5$H$_4$], 6.94 [s, 2H, aromatic CH].

$^{13}$C NMR ([D]benzene, 20° C.): δ 68.8 [CH of C$_5$H$_5$], 73.2, 73.8 [CH of C$_5$H$_4$], 98.0 [aromatic CH].

$^{11}$B NMR ([D$_6$]benzene, 20° C.): δ 34.2.

IR (KBr disk, cm$^{-1}$): 2965 st, 1493 md, 1458 st, 1383 md, 1337 w, 1312 md, 1262 md, 1142 st, 1101 md, 1026 w, 901 w, 845 w, 810 w, 685 w.

UV/Vis (chloroform): $\lambda_{max}$=439 nm.

MS(EI): M$^+$=530 (80%), exact mass (calc.) m/z 530.0246, (obs.) 530.0255.

Example 12

Preparation of 5$^{co}$

5$^{co}$ was prepared from dibromoborylferrocene via route 4 (Scheme 1). In this case 1S,2R,5S,6R-cyclooctane-1,2,5,6-tetrol (1 equiv.) was added to ferrocenediboronic acid (2 equiv.). 5$^{co}$ was isolated in 62% yield as a yellow solid. Single crystals were obtained by slow diffusion of hexanes into an acetonitrile solution at room temperature.

Spectroscopic and Crystallographic Data for 5$^{co}$:

$^1$H NMR ([D]chloroform, 20° C.): δ 1.83 [s, 4H, CH$_2$ of cyclooctane], 2.10 [s, 4H, CH$_2$ of cyclooctane], 4.08 [s, 10H, C$_5$H$_5$], 4.34 [overlapping m, 8H, C$_5$H$_4$], 4.59 [d, 4H, CH of cyclooctane].

$^{13}$C NMR ([D]chloroform, 20° C.): δ 25.0 [CH$_2$ of cyclooctane], 68.5 [C$_5$H$_5$], 72.2 [C$_5$H$_4$], 73.7 [C$_5$H$_4$], 78.5 [CH of cyclooctane].

$^{13}$C NMR (96 MHz, CDCl$_3$): δ 32.4.

IR (KBr disk, cm$^{-1}$): ν 3439 w, 3095 w, 2677 w, 2359 w, 1499 md, 1480 s, 1381 md, 1324 md, 1301 md, 1231 md, 1189 w, 1126 s, 1104 md, 1032 w, 984 md, 862 w, 817 md, 686 w, 502 w, 479 w.

UV/Vis (chloroform): $\lambda_{max}$=444 nm, $\epsilon$=431 mol$^{-1}$ cm$^{-1}$ dm$^3$.

MS (EI): M$^+$=564 (100%), exact mass (calc.) m/z 564.1024, (obs.) 564.1028.

Crystal data for 5$^{co}$: C$_{28}$H$_{30}$B$_2$Fe$_2$O$_4$, orthorhombic, Pnma, a=29.8942(10) Å, b=10.7482(3) Å, c=7.4301(3) Å. V=2387.36(14) Å$^3$, Z=4, D$_{calc}$=1.569 Mg/m$^3$, μ(MoKα)= 1.251 mm$^{-1}$. A suitable crystal was covered in pre-dried mineral oil and mounted at 120(2) K. 2868 unique reflections were collected (2.3<θ<27.5°). Final R-factor: R$_1$=0.077.

Example 13

Preparation of FcBMes$_2$ (6a)

To a solution of dibromoborylferrocene (FcBBr$_2$) (2.00 g, 5.62 mmol) in diethyl ether (50 mL) was added dropwise mesityllithium (2.6 equiv.) also in diethyl ether (ca. 50 mL) and the reaction mixture stirred for 18 h. At this point $^{11}$B NMR indicated complete conversion to a single product ($\delta_B$ 75.8). After removal of volatiles in vacuo, extraction into hexanes (ca. 50 mL) and cooling to −30° C., 6a was obtained as a red powder (yield: 1.52 g, 62%). Single crystals suitable for X-ray diffraction were obtained by slow evaporation of pentanes from concentrated solution.

Spectroscopic and Crystallographic Data for 6a:

$^1$H NMR (300 MHz, [D$_6$]benzene, 20° C.): δ 1.91 (s, 6H, para-CH$_3$ of Mes), 2.21 (s, 12H, ortho-CH$_3$ of Mes), 3.65 (s, 5H, Cp), 4.09 (s, 2H, CH of C$_5$H$_4$), 4.26 (s, 2H, CH of C$_5$H$_4$), 6.54 (s, 4H, aromatic CH of Mes). $^{13}$C NMR (126 MHz, [D$_6$]benzene, 20° C.): 21.0 (para-CH$_3$ of Mes), 24.7 (ortho-CH$_3$ of Mes), 69.6 (Cp), 73.8, 79.6 (C$_5$H$_4$), 128.7 (aromatic CH of Mes), 137.9 (para-quaternary of Mes), 139.2 (ortho-quaternary of Mes), boron-bound quaternary carbons not observed.

$^{11}$B NMR (96 MHz, [D$_6$]benzene, 20° C.): 76.

MS(EI): M$^+$=434.2 (100%), exact mass (calc. for $^{10}$B isotopomer) 433.2899, (obs.) 433.1896.

UV/Vis (CH$_3$CN): $\lambda_{max}$=510 nm, $\epsilon$=1310 mol$^{-1}$ cm$^{-1}$ dm$^3$. E$_{1/2}$ vs. FcH/FcH$^+$ (peak-to-peak separation)=+181 (80) mV in CH$_3$CN.

Crystallographic data: $C_{28}H_{31}BFe$, $M_r=434.2$, monoclinic, $P2_1/n$, $a=10.298(1)$, $b=15.728(1)$, $c=14.027(1)$ Å, $\beta=104.96(1)$, $V=2194.8(2)$ Å$^3$, $Z=4$, $\rho_c=1.314$ Mg m$^{-3}$, $T=120(2)$ K, $\lambda=0.71073$ Å. 22801 reflections collected, 3855 independent [R(int)=0.1177], which were used in all calculations. $R_1=0.0658$, $wR_2=0.1190$ for observed unique reflections [$F^2>2\sigma(F^2)$] and $R_1=0.1189$, $wR_2=0.1463$ for all unique reflections. Max. and min. residual electron densities 0.41 and $-0.42$ e Å$^{-3}$.

Example 14

Preparation of Fc*BMes$_2$ (6b)

To a solution of mesityllithium (0.313 g, 2.48 mmol) in diethyl ether (ca. 35 mL) was added Fc*BBr$_2$ (0.42 equiv.) also in diethyl ether (ca. 30 mL) and the reaction mixture stirred for 18 h, at which point the reaction was judged to be complete by $^{11}$B NMR spectroscopy (quantitative conversion to a single resonance at $\delta_B$ 77.1). After removal of volatiles in vacuo, extraction into hexanes (ca. 20 mL) and cooling to $-30°$ C., 6b was obtained as a purple powder (yield: 0.226 g, 44%). Nb. Fc* is ferrocene but with methyl groups in place of the five hydrogen atoms on one of the cyclopentadienyl rings (the one which does not have the boron atom attached to it).

Spectroscopic and Crystallographic Data for 6b:

$^1$H NMR (300 MHz, [D$_1$]chloroform, 20° C.): $\delta$ 1.66 (s, 15H, CH$_3$ of Cp*), 2.19 (s, 6H, para-CH$_3$ of Mes), 2.30 (s, 12H, ortho-CH$_3$ of Mes), 4.05 (s, 2H, CH of C$_5$H$_4$), 4.15 (s, 2H, CH of C$_5$H$_4$), 6.70 (s, 4H, CH of Mes).

$^{13}$C NMR (126 MHz, [D$_6$]benzene, 20° C.): 11.6 (CH$_3$ of Cp*), 21.3 (para-CH$_3$ of Mes), 25.0 (ortho-CH$_3$ of Mes), 79.9 (quaternary of Cp*), 81.0, 82.1 (C$_5$H$_4$), 128.2 (aromatic CH of Mes), 136.9 (para-quaternary of Mes), 139.1 (ortho-quaternary of Mes), boron-bound quaternary carbons not observed.

$^{11}$B (96 MHz, [D$_6$]benzene, 20° C.): 77.1.

MS(EI): M$^+$=504.2 (100%), exact mass (calc. for $^{10}$B isotopomer) 503.2682, (obs.) 503.2677.

UV/Vis (CH$_3$CN): $\lambda_{max}$=542 nm, $\epsilon$=1420 mol$^{-1}$ cm$^{-1}$ dm$^3$. $E_{1/2}$ vs. FcH/FcH$^+$ (peak-to-peak separation)=$-176$ (75) mV in CH$_3$CN.

Data Characterizing the Response of 1$^s$ and 2$^s$ Towards Fluoride Exposure

Example 15

NMR Analysis of Fluoride Binding

A sample of 1$^s$ (20 mg, 0.049 mmol) was dissolved in dry CDCl$_3$ under anaerobic conditions, and the $^{11}$B and $^1$H NMR spectra measured (to confirm the purity of the starting material). ["Bu$_4$N]F (0.5 equivalents, 6.4 mg, 0.025 mmol) was then quickly added to the solution of the Lewis acid as a solid, and the $^{11}$B and $^1$H NMR spectra measured again (this time indicating a mixture of starting material at $\delta_B$ 34.1, and product at $\delta_B$ 9.1). A further addition of ["Bu$_4$N]F (0.5 equivalents) aided complete conversion to the fluoride adduct, evident in the $^{11}$B NMR spectrum by an upfield shift of ca. 25 ppm relative to the free Lewis acid.

A sample of 2$^s$ (20 mg, 0.032 mmol) was weighed into a Young's NMR tube under anaerobic conditions, dissolved in dry, degassed CDCl$_3$, and compound purity confirmed by $^{11}$B and $^1$H NMR spectroscopy prior to fluoride addition. Tetra-n-butylammonium fluoride hydrate (1 equivalent, 8.3 mg, 0.032 mmol) was added to the Young's NMR tube under an argon atmosphere, the mixture sonicated for 15 min, and the $^{11}$B and $^1$H NMR spectra measured again. At this stage, $^{11}$B NMR of the yellow/orange mixture indicated the presence of both three coordinate and four-coordinate (fluoride-binding) boron centres. Another equivalent of ["Bu$_4$N]F (8.3 mg, 0.032 mmol) was added quickly as a solid to the NMR tube under an argon atmosphere and after further mixing for 15 min spectral acquisition was repeated. The $^{11}$B NMR spectrum now revealed a single broad resonance ($\delta_B$ 9.3) for the bis-fluoride adduct, with no trace of starting material present. Resonances in the $^1$H NMR spectrum at this point appeared slightly broadened (and shifted) in comparison to the initial spectrum. In both cases of 1$^s$ and 2$^s$, treatment of the respective Lewis acid with the alternative fluoride source of potassium fluoride in the presence of 18-crown-6, yields identical spectroscopic results to those observed with ["Bu$_4$N]F, the fluoride adduct appearing as a single broad resonance shifted upfield by approximately 25 ppm from 'free' 2$^s$.

Spectroscopic Data for 1$^s$+["Bu$_4$N]F (1 equiv.):

$^1$H NMR ([D]chloroform, 300 MHz, 20° C.), $\delta$ 0.86 [m, 12H, CH$_3$ of "Bu$_4$N$^+$], 1.24 [br m, 8H, CH$_2$ of "Bu$_4$N$^+$], 1.28 [br m, 8H, CH$_2$ of "Bu$_4$N$^+$], 2.91 [br m, 8H, NCH$_2$ of "Bu$_4$N$^+$], 4.09 [m, 2H, CH of C$_5$H$_4$], 4.19 [S, 5H, CH of C$_5$H$_5$], 4.30 [m, 2H, CH of C$_5$H$_4$], 4.71 [br s, 2H, CH of chelate], 7.18-7.33 [br m, 10H, C$_6$H$_5$].

$^{11}$B NMR ([D]chloroform, 96 MHz, 20° C.), $\delta$ 9.1.

$^{19}$F NMR ([D]chloroform, 283 MHz, 20° C.), $\delta$ $-136.1$.

Spectroscopic Data for 2$^s$+["Bu$_4$N]F (2 equiv.):

$^1$H NMR ([D]chloroform, 300 MHz, 20° C.), $\delta$ 0.91 [br m, 12H, CH$_3$ of "Bu$_4$N$^+$], 1.32 [br m, 8H, CH$_2$ of "Bu$_4$N$^+$], 1.42 [br m, 8H, CH$_2$ of "B$_4$N$^+$], 3.07 [br m, 8H, NCH$_2$ of "Bu$_4$N$^+$], 4.20 [br m, 2H, CH of C$_5$H$_4$], 4.42 [br m, 2H, CH of C$_5$H$_4$], 4.54 [br m, 2H, CH of C$_5$H$_4$], 4.65 [br m, 2H, CH of C$_5$H$_4$], 4.89 [br s, 2H, CH of chelate], 7.15-7.36 [br m, 10H, C$_6$H$_5$].

$^{11}$B NMR ([D]chloroform, 96 MHz, 20° C.), $\delta$ 9.4.

$^{19}$F NMR ([D]chloroform, 283 MHz, 20° C.), $\delta$ $-133.7$.

Spectroscopic Data for 2$^s$+RF/18-crown-6 (2 equiv.):

$^1$H NMR ([D]chloroform, 300 MHz, 20° C.), $\delta$ 3.48 [br s, 18-crown-6], 4.24 [br m, 2H, CH of C$_5$H$_4$], 4.48 [br m, 2H, CH of C$_5$H$_4$], 4.61 [br m, 2H, CH of C$_5$H$_4$], 4.73 [br m, 2H, CH of C$_5$H$_4$], 5.04 [br s, 2H, CH of chelate], 7.28-7.41 [br m, 10H, C$_6$H$_5$].

$^{11}$B NMR ([D]chloroform, 96 MHz, 20° C.), $\delta$ 9.3.

$^{19}$F NMR ([D]chloroform, 283 MHz, 20° C.), $\delta$ $-130.8$.

Example 16

$^1$H NMR Titration of Fluoride Binding to 1$^s$

Anaerobic $^1$H NMR titrations were carried out for compound 1$^s$ by monitoring the chemical shift of the methine protons of the cyclic boronate backbone. On treatment with successive aliquots of fluoride as solid ["Bu$_4$N]F, the methine singlet is found to shift to lower $\delta$. 1$^s$ (78 mg, 0.19 mmol) was weighed into a Youngs NMR tube, dried in vacuo and dissolved in dry, degassed CDCl$_3$. $^{11}$B and $^1$H NMR were initially measured in absence of fluoride; subsequently $^1$H NMR spectra were measured after the successive addition of 0.1, 0.2, 0.3, and 0.4 equivalents of ["Bu$_4$N]F, under anaerobic conditions with mixing between fluoride additions and spectral acquisition. Further $^1$H NMR were measured after the addition of 0.6, 0.8, 1.0, 1.2, 1.4, 1.6, 1.8, and 2.0 equivalents of ["Bu$_4$N]F (0.2 equivalent intervals), with adequate mixing prior to measurement of the $^1$H NMR spectra. Similar experiments were performed on compound 2$^s$, in which successive aliquots of fluoride representing 0.2 equivalents, were added, up to a maximum of 3.0 equivalents.

Example 17

Electrochemical Analysis of Fluoride Binding to $1^s$ and $2^s$

Electrochemical analyses were carried out using the following conditions: electrolyte, 0.1 M [$^n$Bu$_4$N][PF$_6$] in dichloromethane or acetonitrile; reference electrode standard, 0.1 M [$^n$Bu$_4$N][PF$_6$], 0.01 M AgNO$_3$ in acetonitrile. Following degassing of the electrolyte solution with argon, background cyclic voltammetry (CV) scans were measured and a small sample (ca. 2-5 mg) of the ferrocene boronic ester was added to the solution. Further degassing served to purge the solution of any additional dissolved oxygen and agitate the solid Lewis acid to dissolve the compound, prior to spectral acquisition. Further CV scans were measured on the addition of aliquots of solid [$^n$Bu$_4$N]F, and on addition of ferrocene as a reference.

Example 18

UV/Vis Analyses of Fluoride Binding

A sample of $1^s$ or $2^s$ was dissolved in degassed chloroform under anaerobic conditions to give a solution of ca. 5 mM concentration. The solution was then transferred to a UV cell under anaerobic conditions and the spectrum measured. An excess of [$^n$Bu$_4$N]F was then added to the solution which was stirred for 20 min. under aerobic conditions and the UV spectrum measured again.

$1^s$: λ=450 nm, $1^s$+[$^n$Bu$_4$N]F: λ=431 nm.
$2^s$: λ=341, 449 nm, $2^s$+[$^n$Bu$_4$N]F: λ=428, 629 nm.

Example 19

Analysis of Fluoride Binding to $2''$ by Fluorescence Spectroscopy

Following acquisition of a background emission spectrum of acetonitrile in a 0.5 cm$^3$ fluorescence cell, a solution of the parent diol, namely 1-(2-napthyl)-1,2-ethanediol (10 mg, 0.053 mmol) in acetonitrile (100 cm$^3$, 5.3×10$^{-4}$ M) was prepared, and the emission spectrum measured ($\lambda_{ex}$=210 nm, $\lambda_{en}$=330 nm). A 0.02 M solution of compound $2''$ (6 mg, 0.01 mmol) in acetonitrile (0.5 cm$^3$), was then transferred a second fluorescence cell, and the averaged emission spectrum of 10 scans recorded ($\lambda_{ex}$=210 nm, $\lambda_{em}$=370 nm). An excess of solid [$^n$Bu$_4$N]F (>2 equivalents) was then added to the solution, and the emission spectrum recorded at 15 minute intervals over a three hour period ($\lambda_{ex}$=210 nm, $\lambda_{em}$=370 nm).

Analysis of Data Establishing the Response of $1^s$ and $2^s$ Towards Fluoride Exposure Example 20

Multinuclear NMR and Mass Spectrometry Data

Initial anion binding experiments using $1^s$ and $2^s$ were carried out under an inert atmosphere due to the potential sensitivity to aerobic oxygen of any fluoride adduct reaction products. The process of fluoride coordination to the various Lewis acid systems was initially monitored by $^{11}$B and $^{19}$F NMR. The Lewis acid/base interaction of the fluoride anion with $1^s$ and $2^s$ is readily demonstrated by these NMR measurements. In each case, the signal characteristic of the free receptor ($\delta_B$ 34.1, 34.0 respectively) is quantitatively replaced by a resonance at $\delta_B$ ca. 8, characteristic of four-coordinate boronates [RB(OR)$_2$X]−, on addition of 1 equiv. of [$^n$Bu$_4$N]F.xH$_2$O (for mono-functional boronic ester $1^s$; 2 equiv. for $2^s$). Thus for example, coordination of fluoride to $1^s$ in acetonitrile is demonstrated by the appearance of a doublet ($^1J_{BF}$=47.1 Hz) at $\delta_B$ 7.8 and a broad 1:1:1:1 quartet at $\delta_F$ −133.5. The $^{19}$F NMR signal of the species resulting from fluoride treatment ($\delta_F$ −133.7) is shifted significantly from that of [$^n$Bu$_4$N]F itself ($\delta_F$ −122.7). That the boronic ester backbone remains intact under such conditions is readily confirmed by mass spectrometry; negative ion electrospray mass spectrometry measurements on acetonitrile solutions display prominent features characteristic of the adduct [FcBO$_2$C$_2$H$_2$Ph$_2$.F]$^-$ ([$1^s$.F]$^-$) at m/z 427.1 (see FIG. 1).

As witnessed by the corresponding $^{11}$B and $^{19}$F NMR spectra, this fluoride binding behaviour is also observed for other Lewis acids of the types decribed above. Here too, treatment of a chloroform solution of the respective ferrocene boronic ester with [$^n$Bu$_4$N]F under anaerobic conditions results in a similar upfield shift in the $^{11}$B NMR signal (approximately 25 ppm); the $^{19}$F chemical shifts found for the fluoride adducts range from $\delta_F$ 128-135.

Changes in the $^1$H NMR spectrum upon fluoride treatment are apparent as slight broadening of Cp and boronic ester resonances from the parent compound, together with a small up-field shift of the respective resonances (discussed below in respect of NMR titration measurements). No analogous changes in the $^1$H and $^{11}$B NMR spectra were observed upon the addition of large excesses (>20 equivalents) of Cl$^-$, Br$^-$, I$^-$, BF$_4^-$, PF$_6^-$, H$_2$PO$_4^-$, HSO$_4^-$ or NO$_3^-$, indicating that the binding process is selective for fluoride.

The similar magnitudes of shifts in $^{11}$B resonances observed for $1^s$ and $2^s$ in the presence of fluoride imply a common mode of Lewis acid/base interaction in each case, i.e. coordination of a single mondentate fluoride ion at each boronic ester function. Further insight as to the actual mode of coordination has been provided by anaerobic $^1$H NMR titration experiments involving $1^s$ and $2^s$. These experiments not only confirm that $2^s$ binds two equivalents of fluoride at essentially independent boronic ester sites, but also allows the relatively weak binding of the fluoride anion to be quantified.

Figure 2:
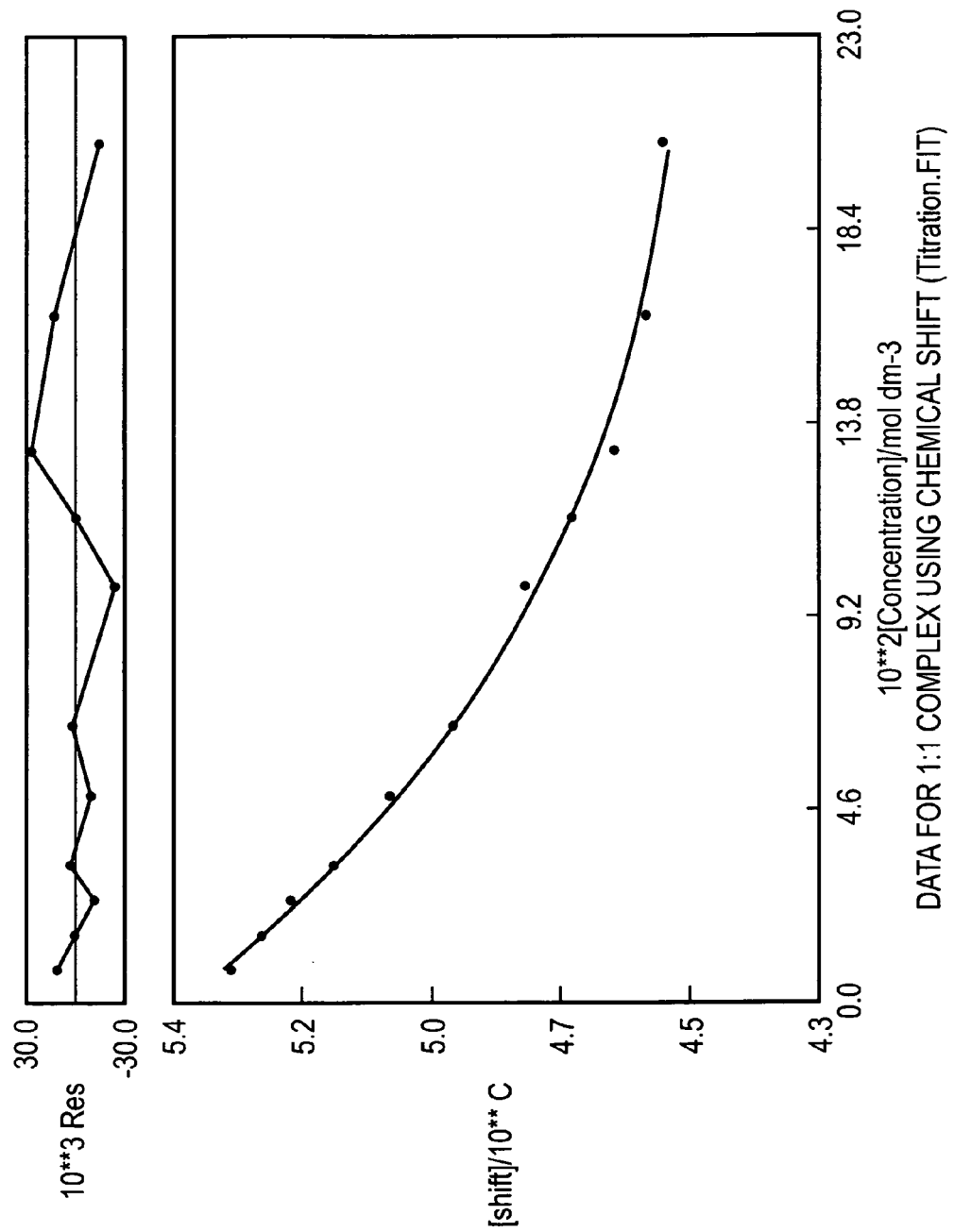
FIG. 2 shows a $^1$H NMR titration curve for compound 1$^s$ on addition of fluoride (obtained using WinEQNMR).

Data for $1^s$ (chemical shift δ vs. concentration of fluoride—see FIG. 2) were obtained using the method outlined above and fitted using WinEQNMR [WinEQNMR software: M. J. Hynes, J. Chem. Soc., Dalton Trans. (1993) 311], giving a relatively weak binding constant (K=35.8±9.8 M$^{-1}$). Although the binding constant calculated for $1^s$ is clearly indicative of a relatively weak Lewis acid/base interaction, we attribute the observed fluoride ion selectivity to this weakness of anion binding. Fluoride has previously been shown to bind to boronic acids with binding constants greater than two orders of magnitude larger than chloride or bromide [Halide binding: C. Dusemund, K. R. A. S. Sandanayake, S. Shinkai, J. Chem. Soc., Chem. Commun. (1995) 333]. Consequently if fluoride binding is itself weak, other anions might be expected to be effectively non-interacting with the Lewis acid centre. Consistent with this, no significant changes are observed in $^1$H and $^{11}$B NMR spectra of $1^s$ even in the presence of large excesses of alternative anions (e.g. >20 equivalents of Cl$^-$, Br$^-$, I$^-$, [BF$_4$]$^-$, [PF$_6$]$^-$, [H$_2$PO$_4$]$^-$, [HSO$_4$]$^-$ or [NO$^3$]$^-$ as the [$^n$Bu$_4$N]$^+$ salts). Similar $^1$H titration experiments performed for $2^s$ reveal a 2:1 fluoride:$2^s$ binding stoichiometry, consistent with binding of a single fluoride at each boronic ester function, rather than fluoride chelation.

Example 21

Colorimetric and UV/Vis Experiments

Fluoride binding experiments under aerobic conditions were also carried out with compound $2^s$. However, attempts to carry out $^1$H NMR titration experiments were inhibited by significant broadening of the relevant resonances, leading to unreliable data. Moreover, under aerobic conditions, treatment of a chloroform or dichloromethane solution of $2^s$ with an excess (≥2 equivalents) of fluoride, either as the tetra-n-butylammonium salt or as the potassium salt with 18-crown-6 is found to lead to a colour change from orange to green.

Figure 3:
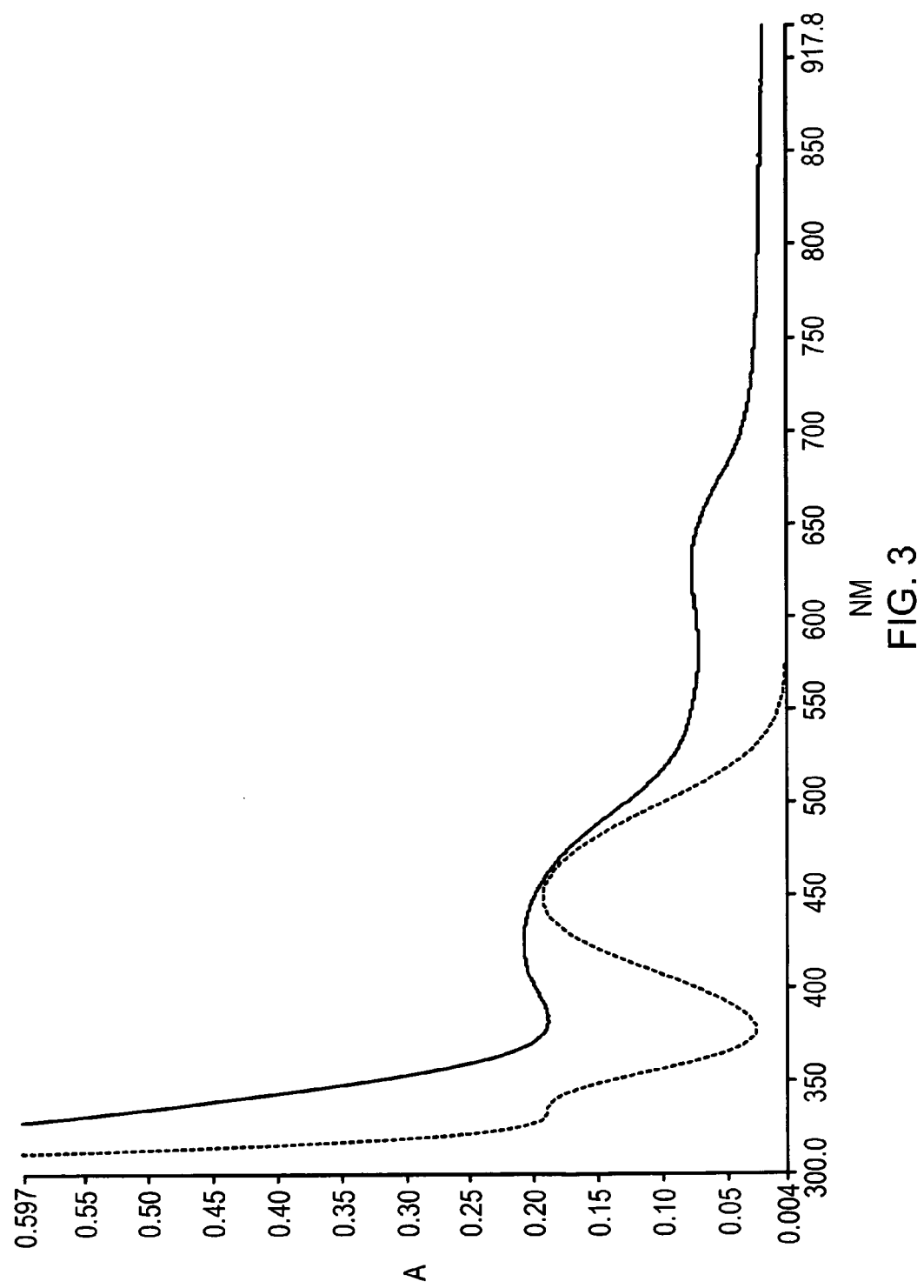
FIG. 3 shows UV/Vis spectra of compound 2$^s$ (upper trace—solid line), and compound 2$^s$ plus ≥2 equivalents of [$^n$Bu$_4$N]F (lower trace—dashed line) in chloroform solution.

By contrast, no colour change is found to take place if the same experiment is performed under anaerobic conditions, or if an alternative anion is used instead of fluoride ($Cl^-$, $Br^-$, $I^-$, $BF_4^-$, $PF_6^-$, $H_2PO_4^-$, $HSO_4^-$ or $NO_3^-$, as the $[^nBu_4N]^+$ salt). UV/Vis spectroscopy provides a convenient means of monitoring the orange to green colour change. For the bis-borylferrocene $2^s$, the UV/Vis spectrum in $CHCl_3$ solution in the absence of fluoride is characterized by bands at 341 and 449 nm. These bands are quantitatively replaced by new features at 428 nm and 629 nm upon the addition of two equivalents of solid $[^nBu_4N]F$ (see FIG. 3). Ferrocene itself displays no significant absorptions above 530 nm, whereas the oxidised form, the ferrocenium cation, displays absorptions attributable to a $^2E_{2g} \rightarrow ^2E_{1u}$, LMCT process at 617 nm [Ferrocenium UV/Vis spectrum: A. B. P. Lever, in *Inorganic Electronic Spectroscopy*, Elsevier, Amsterdam, 2nd edn., 1984, pp. 659-671.]. The band at 629 nm is therefore indicative of a ferrocenium type species, formed by oxidation of the Lewis acid $2^s$ by atmospheric oxygen on complexation of two equivalents of fluoride. By contrast, the binding of fluoride to $1^s$ under aerobic conditions reveals a different (null) colorimetric response to that seen for the bis(boronic) ester $2^s$. Treatment of a chloroform solution of $1^s$ in air with excess $[^nBu_4N]F$ is not accompanied by a colour change from orange to green, instead the reaction mixture remains orange-yellow in colour. As a result, the UV/Vis analysis of compound $1^s$ displays no bands characteristic of ferrocenium-type species (~617 nm) on fluoride treatment.

Example 22

Electrochemical Studies

Figure 4:
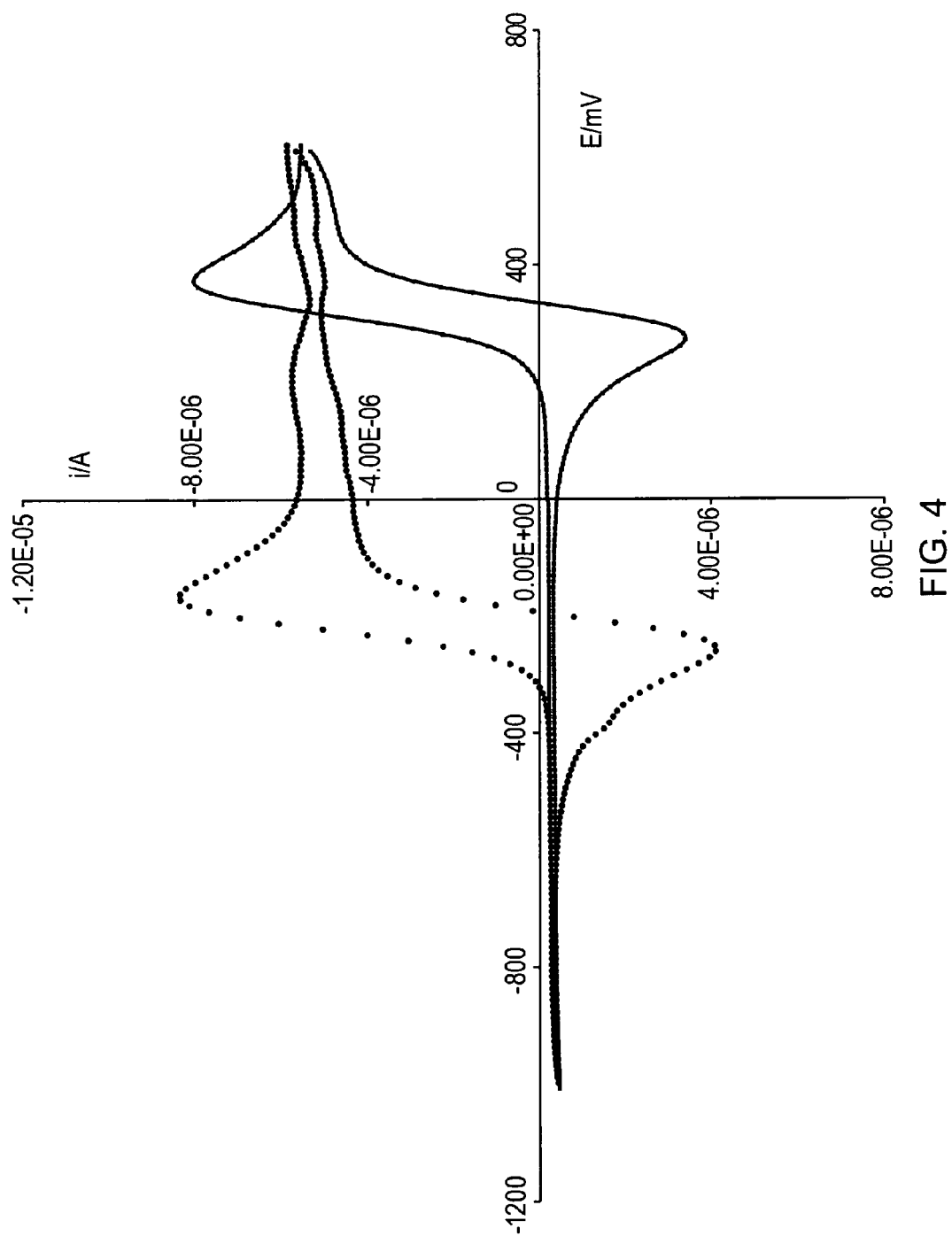
FIG. 4 shows a cyclic voltammogram of compound 1$^s$ (solid trace) and compound 1$^s$ plus ≥1 equivalent of [$^n$Bu$_4$N]F (dashed trace) in MeCN.
Figure 5:
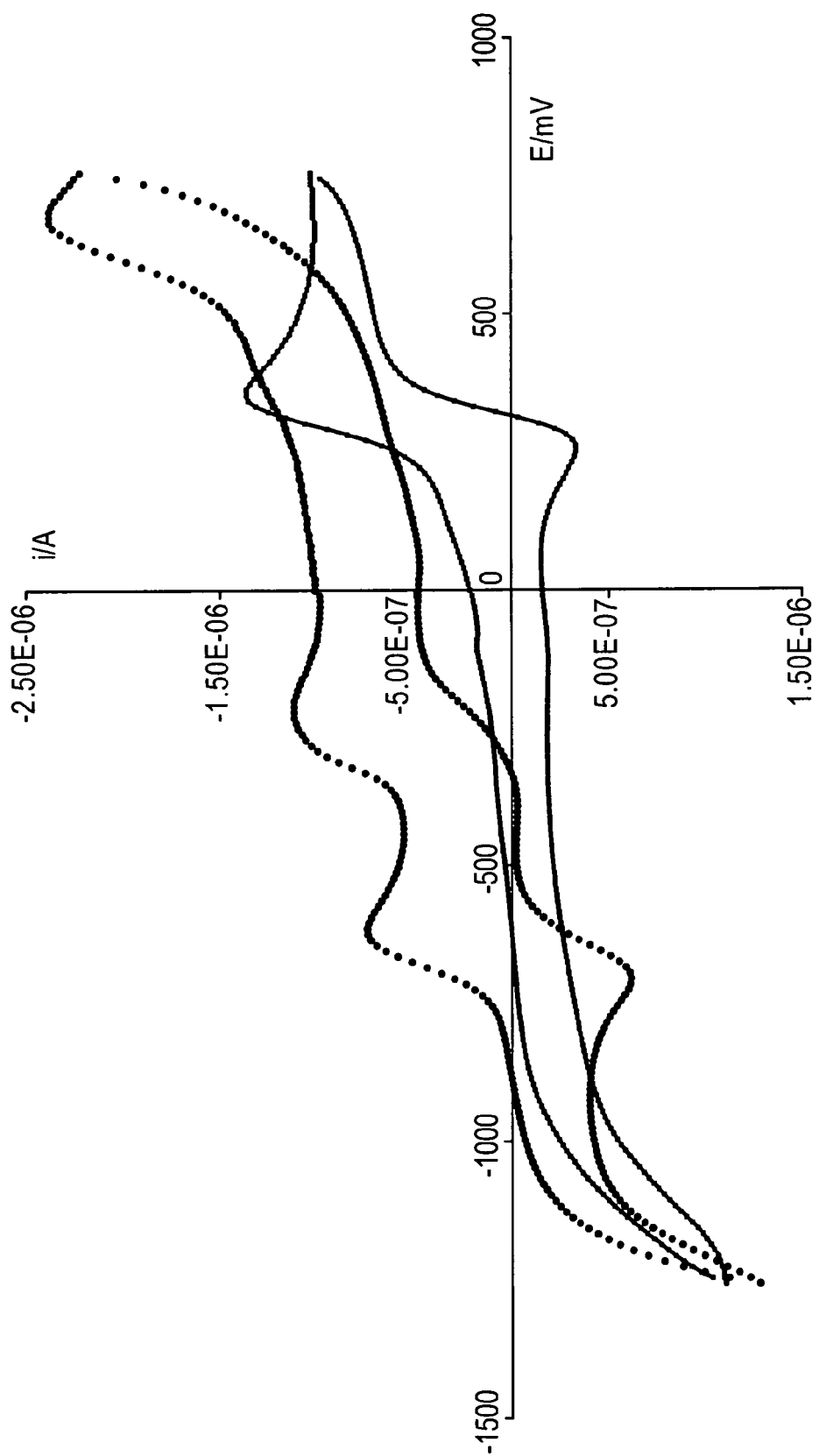
FIG. 5 shows a cyclic voltammogram of compound 2$^s$ (solid trace) and compound 2$^s$ plus ≥2 equivalents of [$^n$Bu$_4$N]F (dashed trace) in MeCN.

Cyclic voltammetry (CV) measurements were performed on compounds $1^s$ and $2^s$ in order to monitor the process of fluoride binding by these systems. Analyses were performed in dry, degassed dichloromethane or acetonitrile by adding a small aliquot of $[^nBu_4N]F$ to the electrochemical cell following CV measurement on the free compound. The cyclic voltammograms for $1^s$ and $2^s$ (solid traces), and for $1^s$ and $2^s$ in the presence of excess $[^nBu_4N]F$ (dashed traces) are illustrated in FIGS. 4 and 5 below; the CV data extracted from these measurements is summarised in Table 7.

TABLE 7

Electrochemical data for compounds $1^s$ and $2^s$, before/after addition of fluoride {as $[^nBu_4N]F$}.

| Compound | Solvent | Initial oxidation potential (mV) | $F^-$ adduct oxidation potential (mV) | $F^-$ adduct potential relative to FcH (mV) | Shift in oxidation potential (mV) |
|---|---|---|---|---|---|
| $1^s$ | DCM | +318 | −217 | −403 | −535 |
| $1^s$ | MeCN | +202 | −292 | −378 | −494 |
| $2^s$ | DCM | +448 | −554 | −746 | −1002 |
| $2^s$ | MeCN | +302 | −660 | −750 | −962 |

The effect of fluoride on the oxidation potential of Lewis acid $1^s$ is illustrated clearly by a shift to a more negative potential (solid to dashed CV trace). This cathodic shift is consistent with the binding of fluoride, since on coordination the ferrocene moiety becomes relatively electron rich and the electron withdrawing effect of the boronic ester group is replaced by the net electron-donating properties of the anionic borate. Of particular interest is the magnitude of the cathodic shift between the free compound $1^s$ and the monofluoride adduct, compared to the equivalent experiment involving the bis-boronic ester $2^s$. On the addition of fluoride to the electrochemical cell, the oxidation potential of $1^s$ undergoes a shift of approximately −0.5 V, a value which is about half of that seen for the bifunctional analogue $2^s$ on fluoride treatment (ca. −1 V). In each case the conversion of an electron withdrawing boronic ester group to a negatively charged (and strongly electron donating) boronate function leads to an increase in electron density at the Fe(II) centre, and hence to a marked cathodic shift in the oxidation potential. That the magnitude of the shift in the case of $2^s$ (which binds two fluorides to give $[2^s.2F]^{2-}$) is essentially twice that for $1^s$ (which binds only a single fluoride to give $[1^s.F]^-$) simply relects the number of pendant boronic ester functions being converted to boronates (i.e. 2 vs. 1).

The second reversible feature found in the CV spectrum of $2^s$ in the presence of fluoride (at −318 mV in acetonitrile) is explained by the presence of the mono fluoride adduct of $2^s$ (i.e. $[2^s.F]^-$) by analogy with the shift measured for the monofluoride adduct of $1^s$ ($[1^s.F]^-$; 292 mV in acetonitrile).

Example 23

Fluorescence Studies

Figure 6:
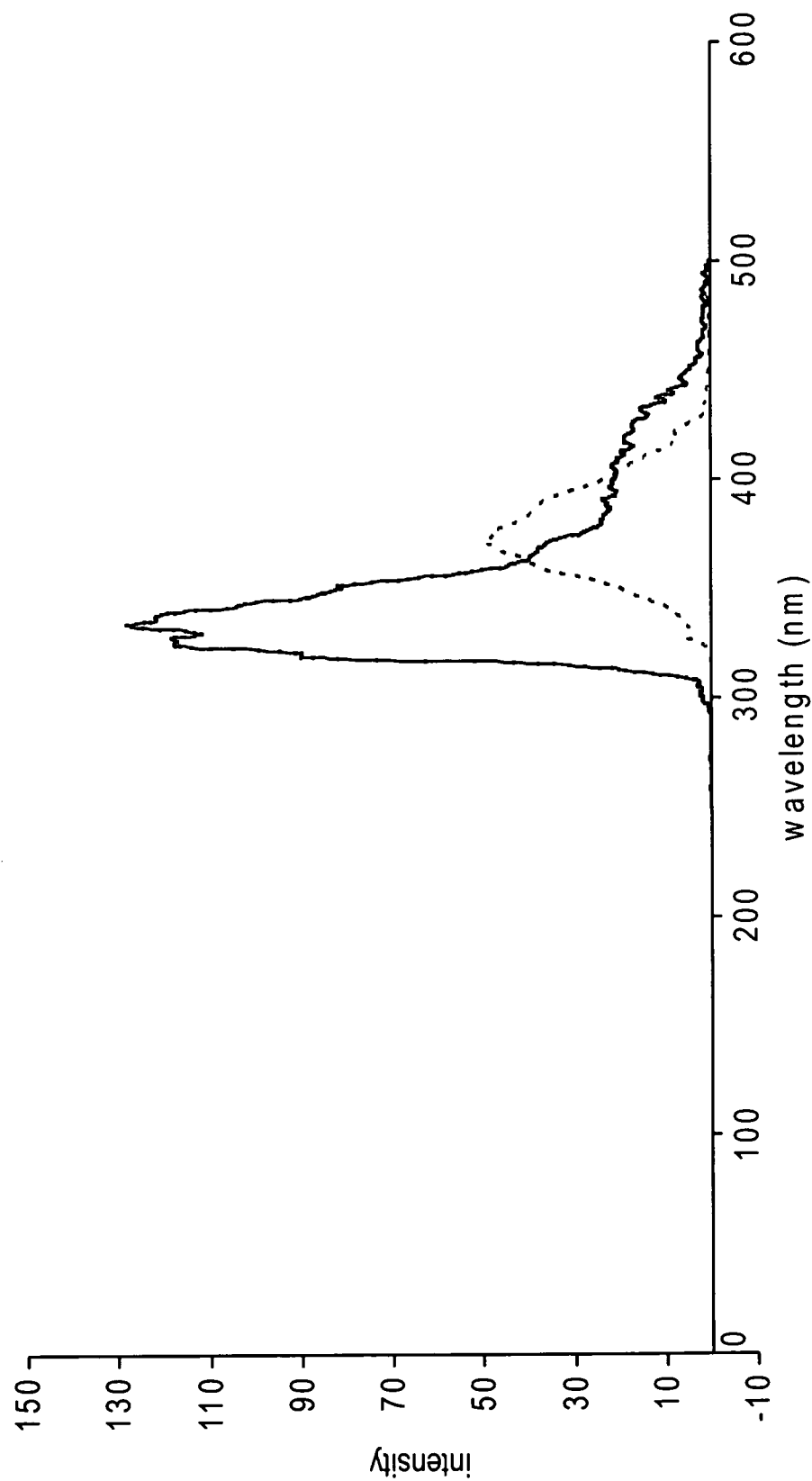
FIG. 6 shows fluorescence emission spectra of 1-(2-napthyl)-1,2-ethanediol (5×10$^{-4}$ M, solid trace), and compound 2$^n$ (0.02 M, dashed trace) in acetonitrile solution.

Fluorescence quenching upon anion complexation is a widely utilized phenomenon not only for the qualitative detection of anions in solution, but also for quantifying the anion-receptor interaction, for example, by fluorescence titration experiments. The napthalene moiety in particular is known to be an effective fluorescent chromophore as a result of $\pi \rightarrow \pi^*$ transitions, which allow clear and distinct spectra to be obtained. Thus, the fluorescence emission spectra of 1-(2-napthyl)-1,2-ethanediol (the parent-diol from which $2''$ is derived), and the napthylene-containing receptor $2''$ were measured, as were the spectra of $2''$ over time following exposure to fluoride ($[^nBu_4N]F$). The emission spectra of 1-(2-napthyl)-1,2-ethanediol (solid trace) and $2''$ (dashed trace) are shown in FIG. 6, demonstrating clearly the modifying effect of the ferrocene boronic ester framework on the fluorescence intensity of the napthalene moiety.

The change in fluorescence behaviour between the parent diol and 2″ is characterised by a shift in the emission wavelength from $\lambda_{em}$=330 nm to $\lambda_{em}$=370 nm (for 2″). More noticeable, however, is the significant reduction in fluorescence intensity of the napthalene moiety upon incorporation within the ferrocene boronic ester framework. This quenching effect occurs despite the increased concentration of 2″ compared to the parent-diol (0.02 vs. 5×10$^{-4}$ M), and the fact that there are two napthyl groups incorporated in each molecule of 2″. Despite this, the napthyl groups of 2″ still provide sufficient fluorescence intensity to allow for the monitoring of fluoride-binding events by fluorescence spectroscopy.

Figure 7:
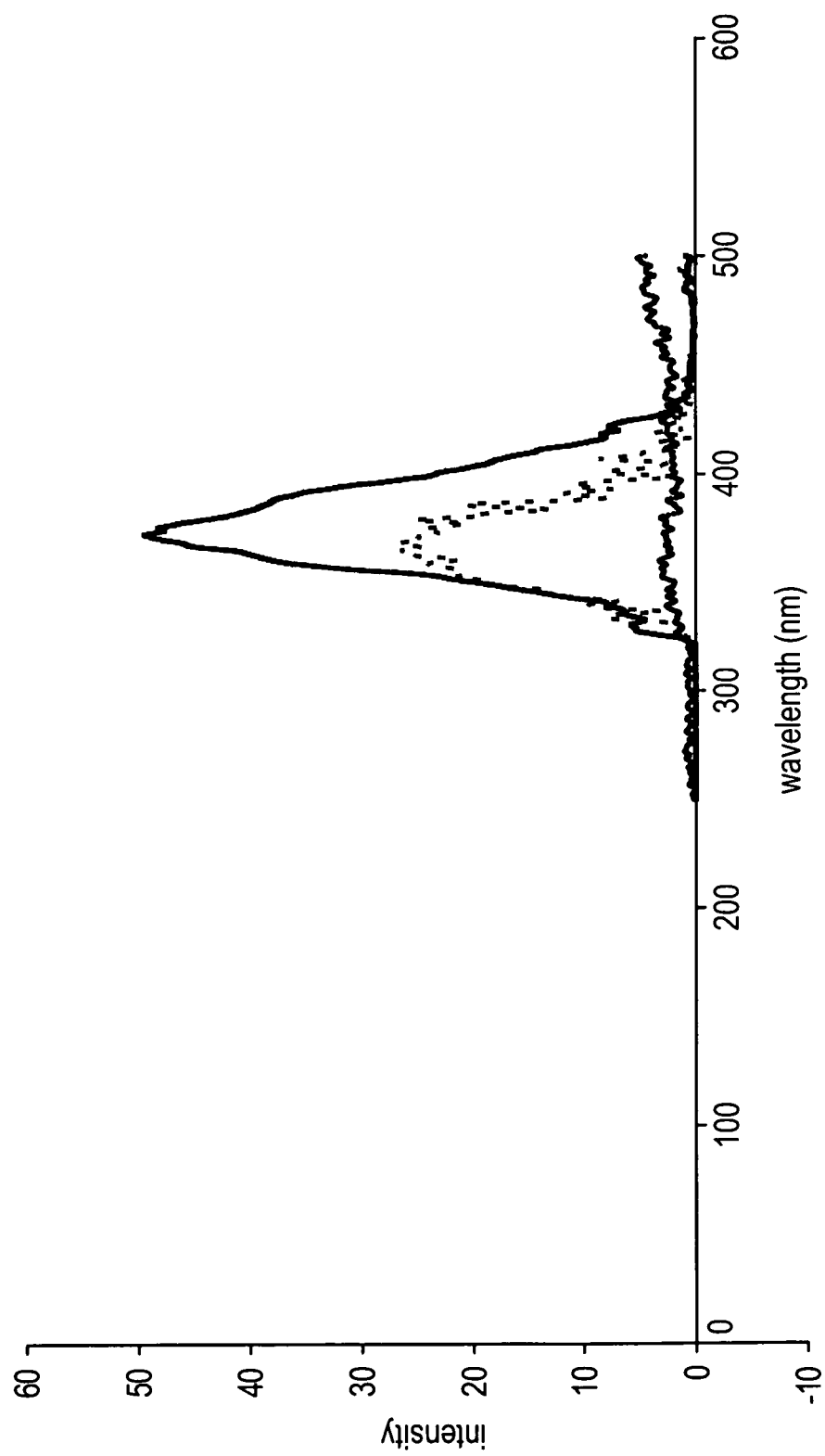
FIG. 7 shows the change in the fluorescence spectrum of compound 2$^n$ (0.02 M in MeCN) as a function of time after addition of excess fluoride: without F$^-$ (top, solid line), with addition of excess F$^-$, after 15 min. (middle, dashed line), and 5 h (bottom, dashed line).
Figure 8A:
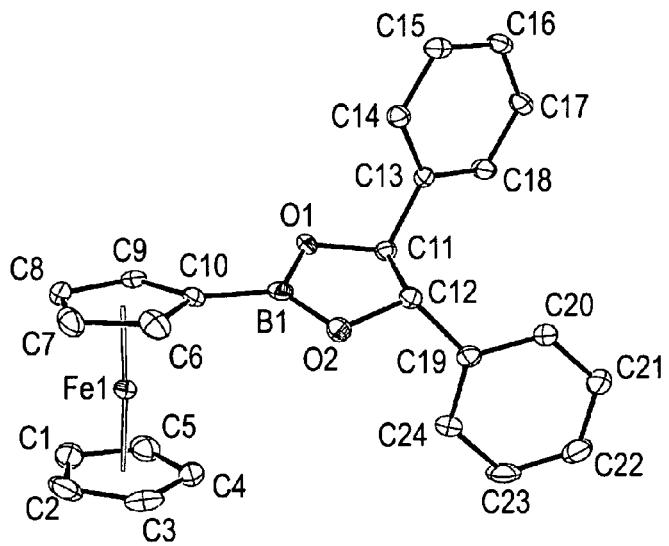
FIG. 8a-h show the crystal structures of various organometallic compounds useful in the described detectors. In each case hydrogen atoms have been omitted for clarity and ORTEP ellipsoids set at the 50% probability level.
Figure 8B:
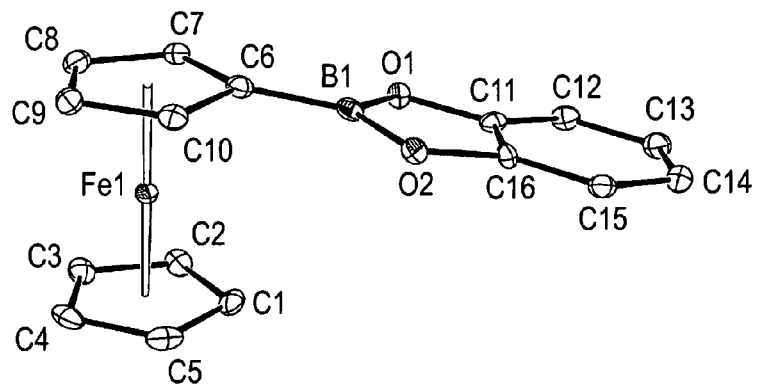
Figure 8C:
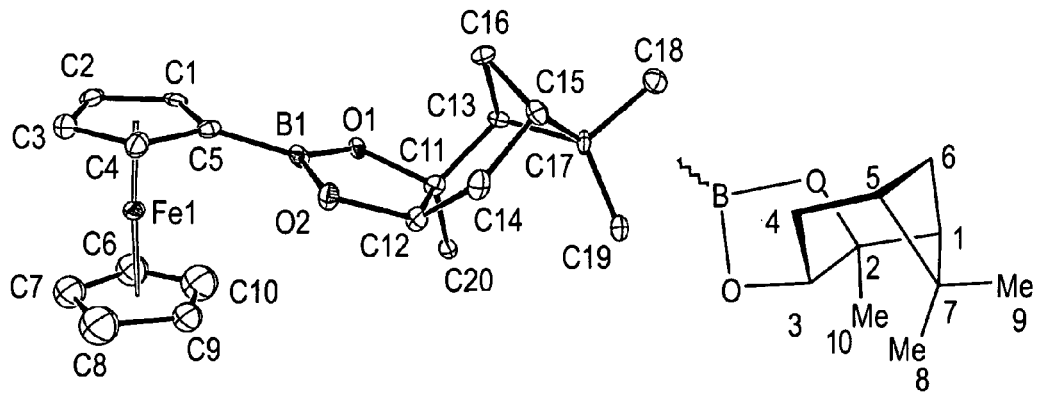
Figure 8D:
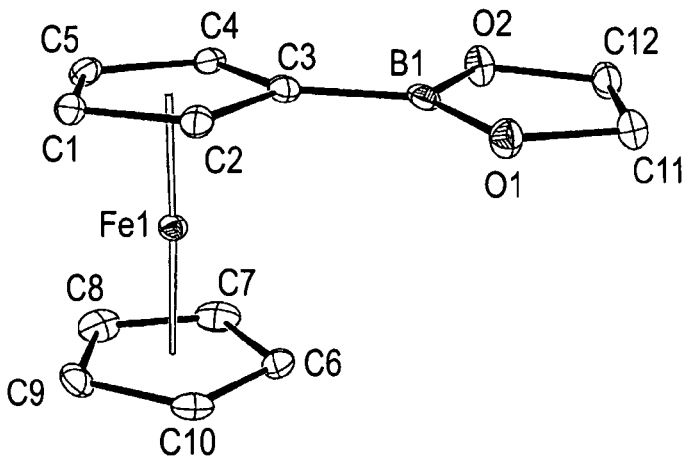
Figure 8E:
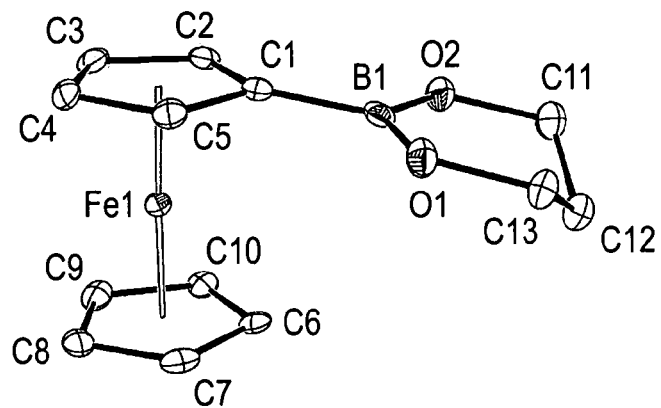
Figure 8F:
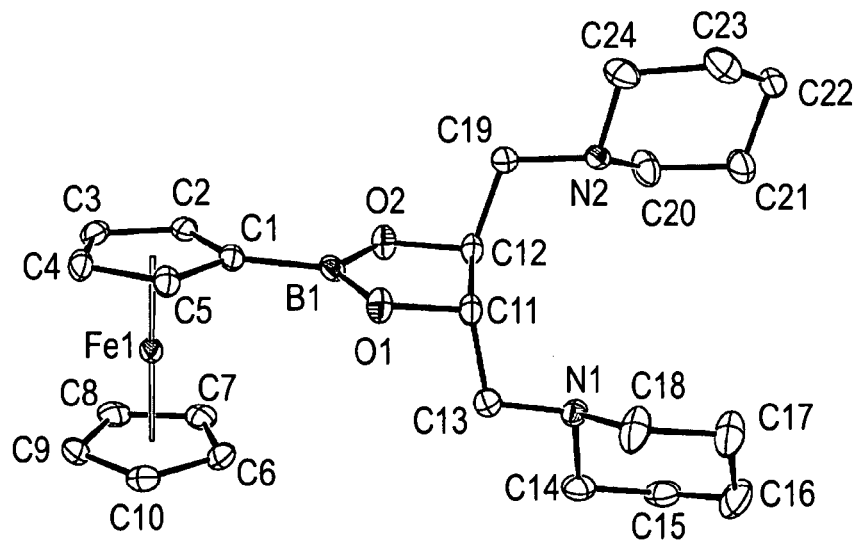
Figure 8G:
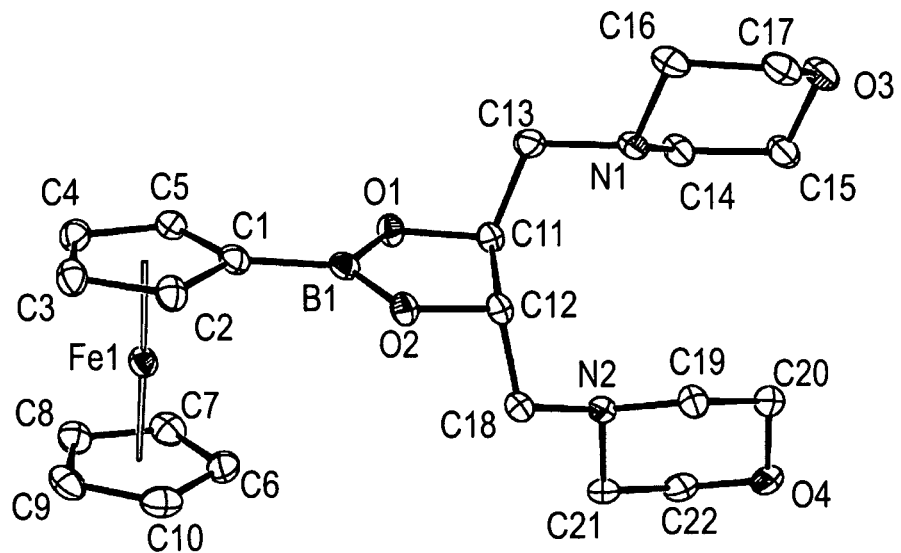
Figure 8H:
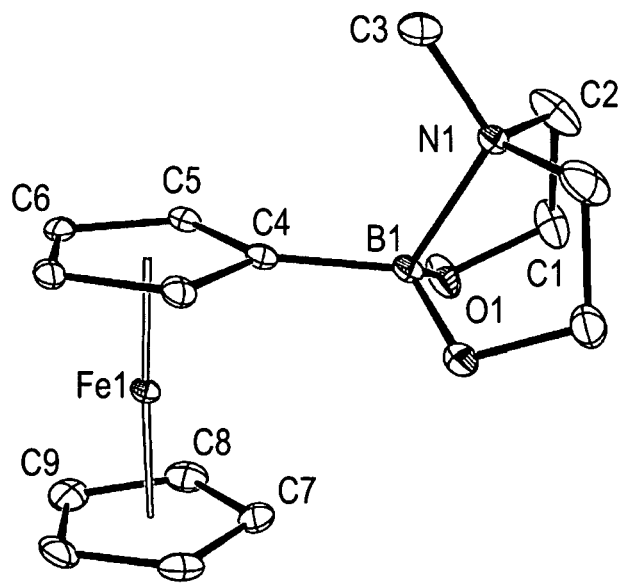
Figure 9A:
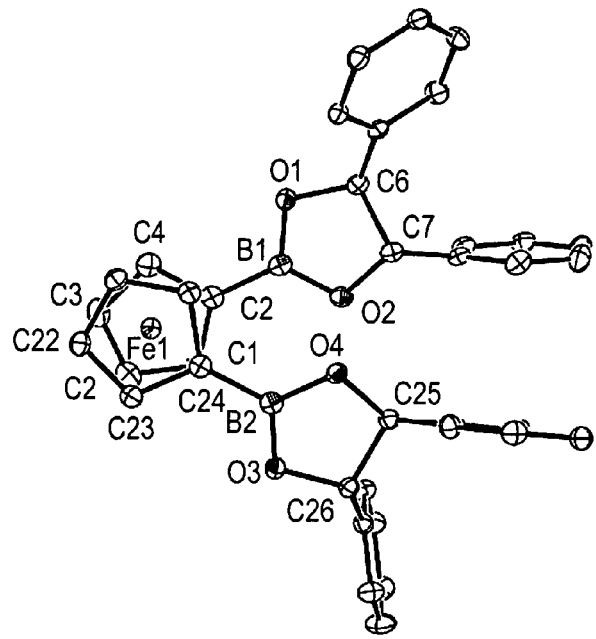
Figure 9B:
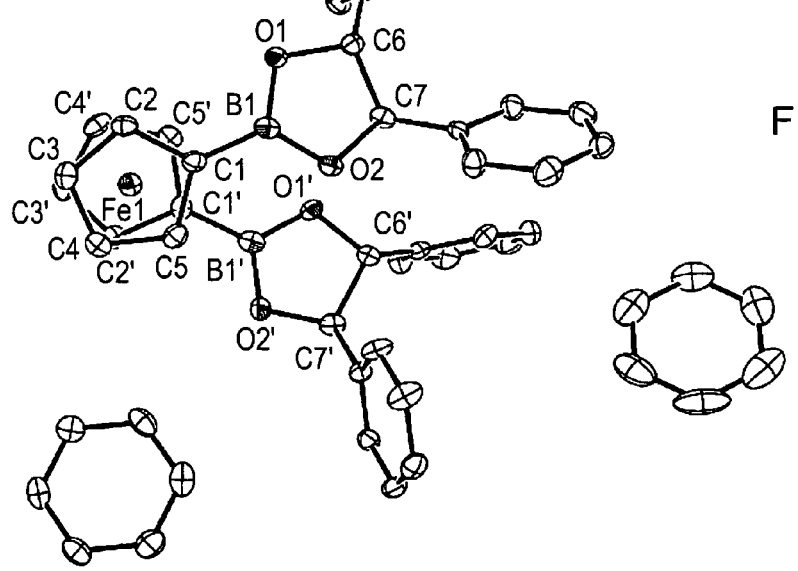
Figure 9C:
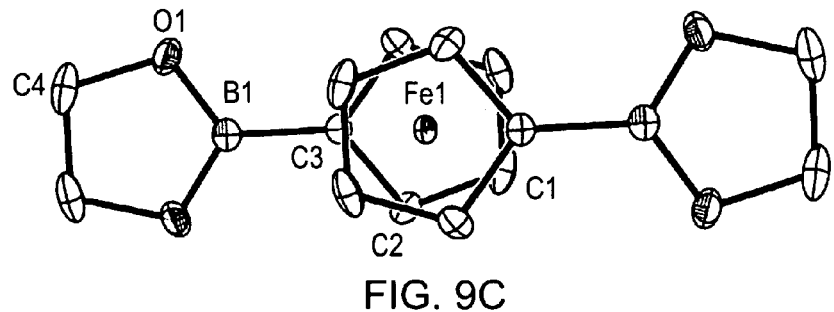
Figure 10:
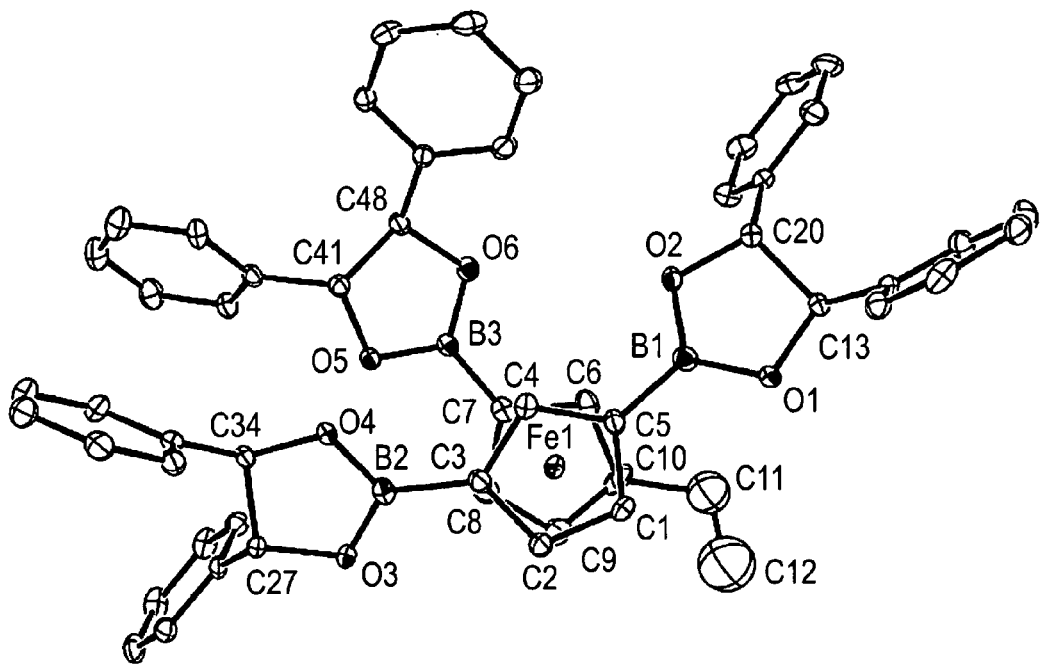
FIG. 10 shows the crystal structure of the organometallic compound 3$^s$ which is useful in the described detectors. The hydrogen atoms have been omitted for clarity and ORTEP ellipsoids set at the 50% probability level.
Figure 11A:
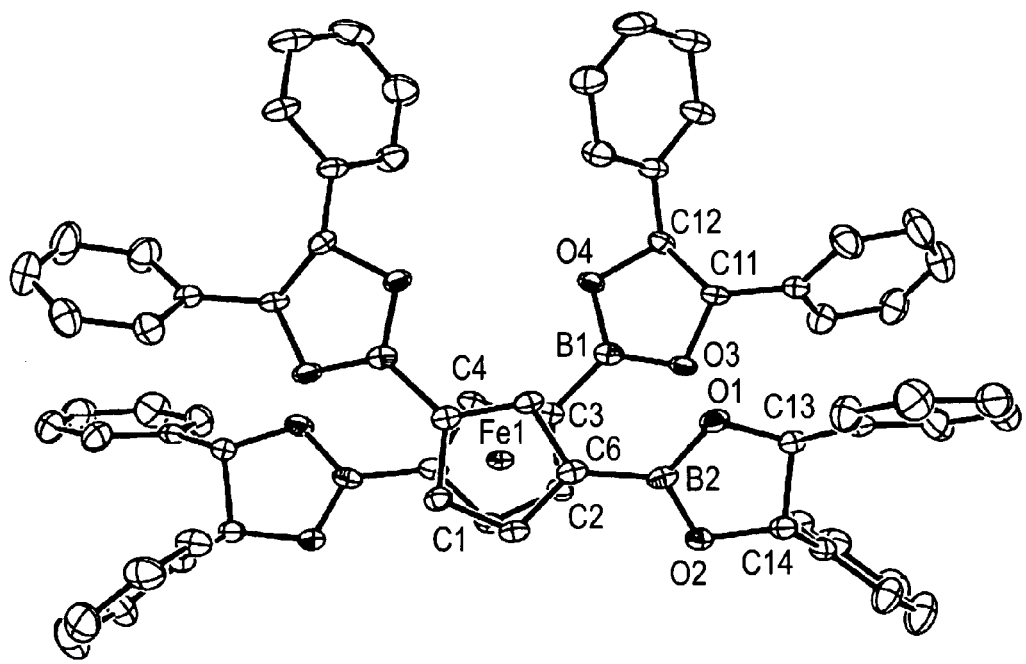
FIG. 11a-c show the crystal structures of various organometallic compounds useful in the described detectors. In each case hydrogen atoms have been omitted for clarity and ORTEP ellipsoids set at the 50% probability level.
Figure 11B:
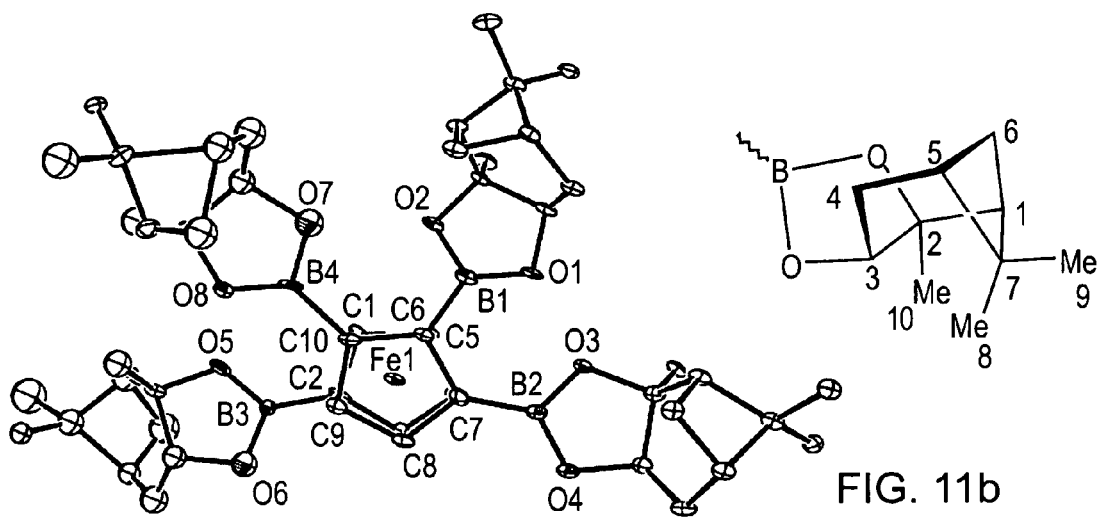
Figure 11C:
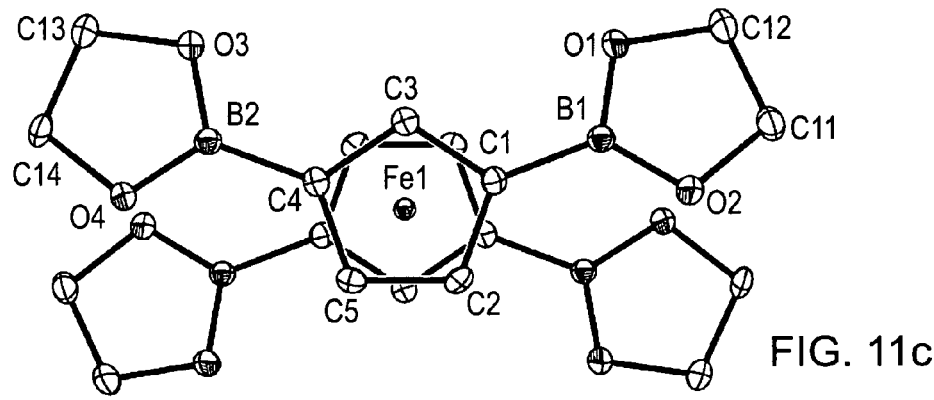
Figure 12A:
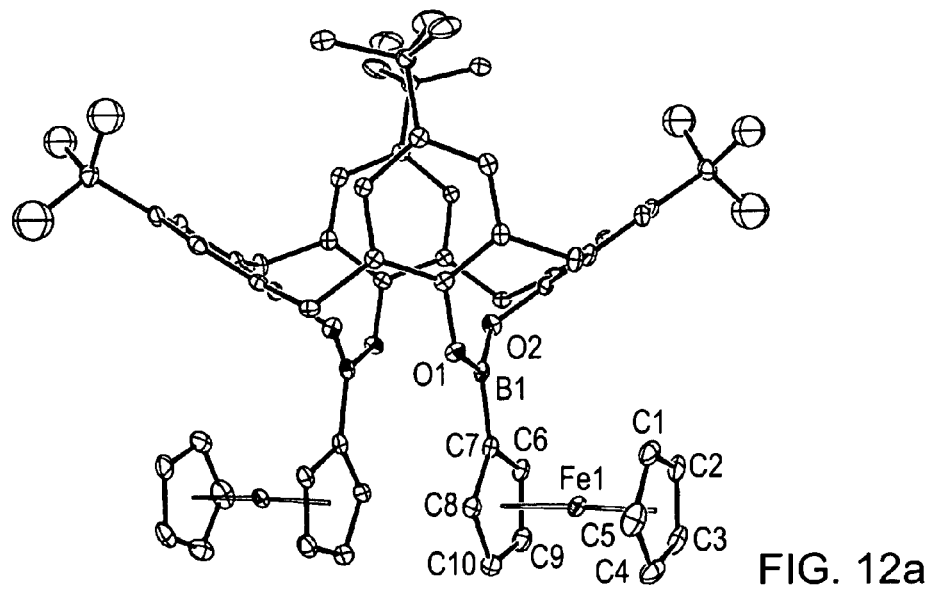
FIG. 12a-b show the crystal structures of organometallic compounds useful in the described detectors. In each case hydrogen atoms have been omitted for clarity and ORTEP ellipsoids set at the 50% probability level.
Figure 12B:
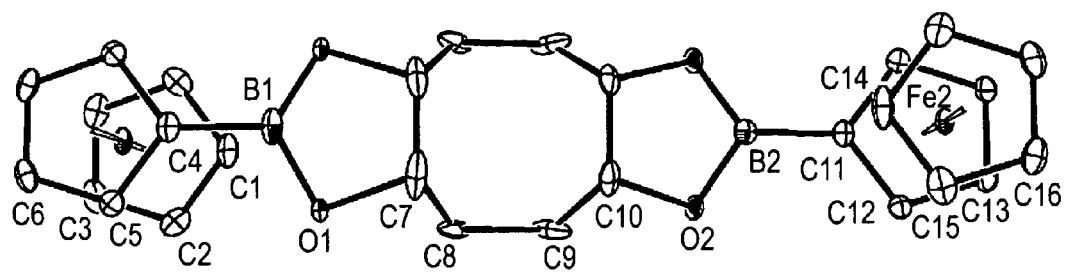

The effect on the fluorescence spectrum of 2″ of the addition of excess fluoride (as [″Bu$_4$N]F) as a function of time (12 hour period) is illustrated in FIG. 7. The addition of fluoride to the 2″ causes significant quenching of the fluorescence intensity, as is evident in FIG. 7. This result is in agreement with the data obtained from the NMR and UV/Vis spectroscopic analysis of fluoride binding to such receptors, since it is well established that the binding of anions to Lewis acidic boron can result in the quenching of fluorescence of directly attached fluorophores. Furthermore, it appears likely that the effect of aerobic oxidation of the bis-fluoride adduct (as seen from UV/Vis spectroscopy and the naked eye) also plays a part in the quenching of fluorescence intensity. A gradual decay of fluorescence over time is also expected due to Fe(II)/Fe(III) oxidation in the bis(fluoride) adduct [2″.2F]$^{2-}$; the resulting paramagnetic ferrocenium centre is then responsible for very efficient fluorescence quenching. It appears likely therefore that the substantial quenching of fluorescence upon fluoride treatment of 2″ is caused by two contributing factors.

Example 24

Mode of Action of 2$^s$ as a Colorimetric Fluoride Sensor and 1s as an Electrochemical Fluoride Sensor The presence of a single boronic ester moiety that can bind a single fluoride ion, as in the case of 1$^s$, does bring about a colorimetric response to the coordination of fluoride. The CV results demonstrate that the binding of fluoride to such monofunctional ferrocene boronic esters shifts the Fe(II)/Fe(III) oxidation potential by ca. 0.5 V in non-aqueous media, but that the magnitude of this shift is not sufficient for atmospheric oxygen to oxidise the anionic adducts (e.g. [1$^s$.F]$^-$).

With respect to the bifunctional species (e.g. 2$^s$) it can be shown that the mode of action of the bifunctional receptors in fluoride ion sensing involves: (i) the selective binding of fluoride (2 equiv.); (ii) a cathodic shift in the oxidation potential of the iron centre in the presence of fluoride (of ca. 1 V in non-aqueous media); and (iii) an orange to green colour change arising from the generation of a ferrocenium-based final product by aerobic oxidation of the bis-fluoride adduct (not observed under anaerobic conditions). These inferences appear consistent with the chemistry outlined in Scheme 2.

Example 25

Data Characterizing the Response of 6a Towards cyanide Ion (CN$^-$) Exposure (Formation of [nBu$_4$N]+[6a.CN]$^-$)

Figure 15:
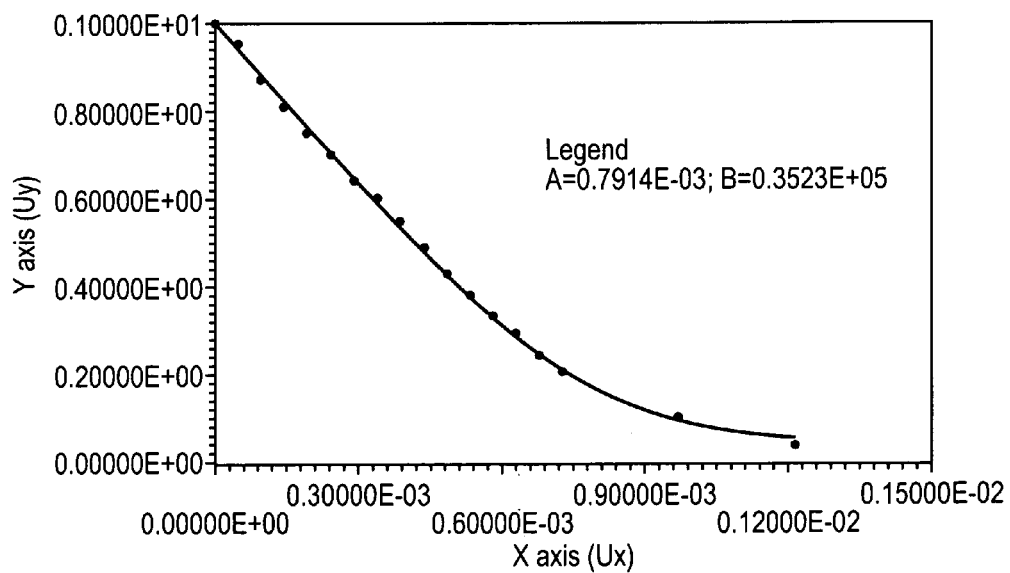
FIG. 15 shows the plot used for determining the binding constant of compound 6a in the presence of CN$^-$ anions.
Figure 16:
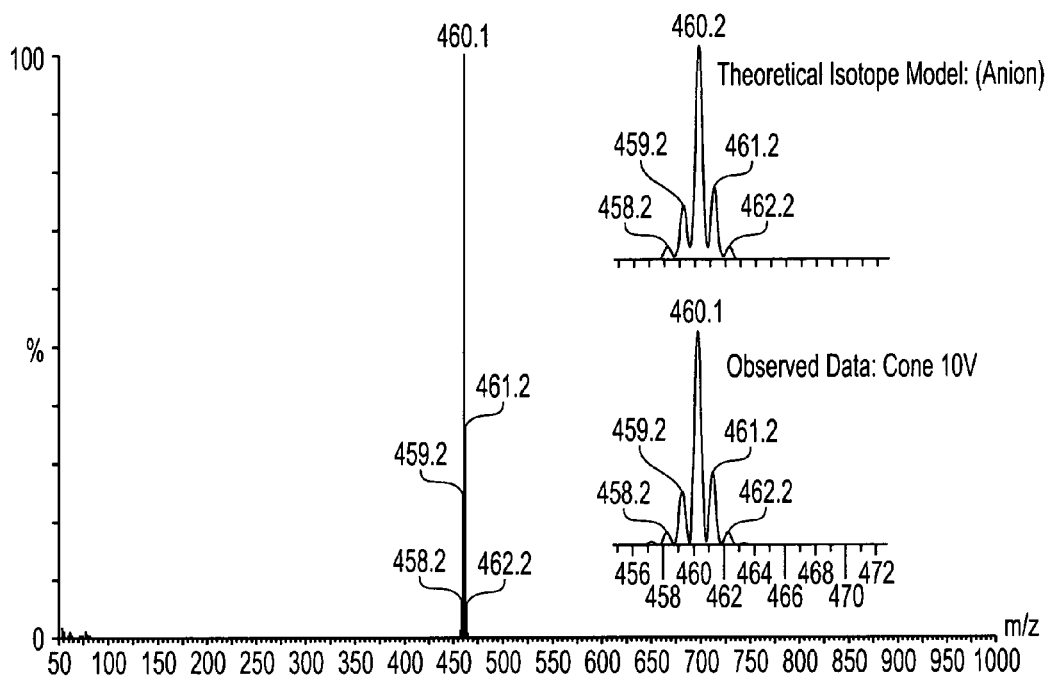
FIG. 16 shows the electrospray mass spectrograph of the complex of compound 6a bound to one cyanide anion.
Figure 17A:
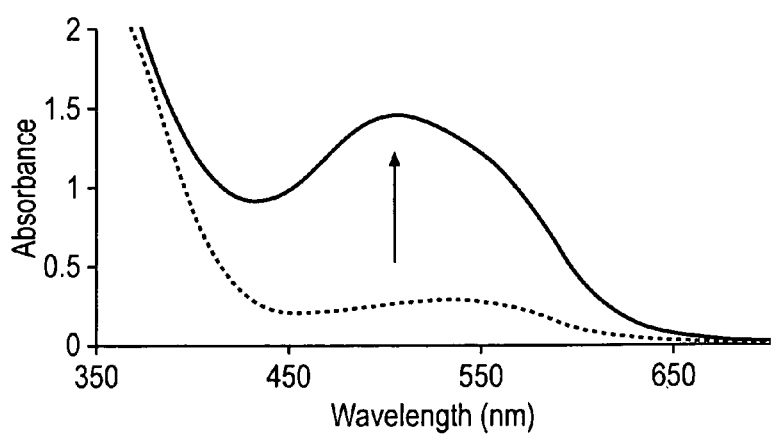
FIG. 17a-d show UV/Visible spectra of acetonitrile solutions containing Lewis acid receptors 6b or 1$^s$* (0.5 mM) and tetrazolium violet (1.0 mM) in the absence (grey trace) and presence (black trace) of added anion.
Figure 17B:
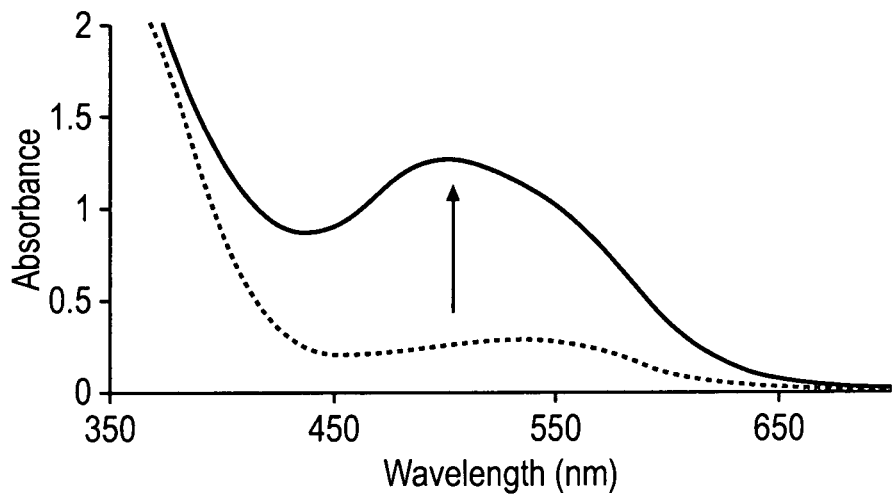

The binding of cyanide (as either KCN/18-crown-6 or [nBu$_4$N]$^+$[CN]$^-$.2H$_2$O$^y$) by compound 6a in a range of solvents (chloroform, dichloromethane, acetonitrile) is readily be demonstrated/quantified by a combination of spectroscopic techniques. Thus, the changes in $^{11}$B NMR chemical shift ($\delta_B$ 76 to −16) and IR-detected v(CN) stretching frequency (2080 to 2155 cm$^{-1}$) are in line with previous reports of cyanide complexation to boron-based Lewis acids. In addition, ESI-MS sampling of the reaction mixture (FIG. 16) reveals a 'flag-pole' mass spectrum with isotopic profile and measured exact mass consistent with the formulation [6.CN]$^-$. The thermodynamics of cyanide binding to compound 6a can readily be assessed by monitoring the intensity of the band at 510 nm (in the electronic spectrum of 6a) as a function of the concentration of added cyanide (FIG. 17b). A binding constant of 3.5(0.4)×10$^4$ mol$^{-1}$ dm$^3$ can be determined by fitting the resulting curve of absorbance vs. cyanide concentration in dichloromethane solution (FIG. 15).

Figure 13:
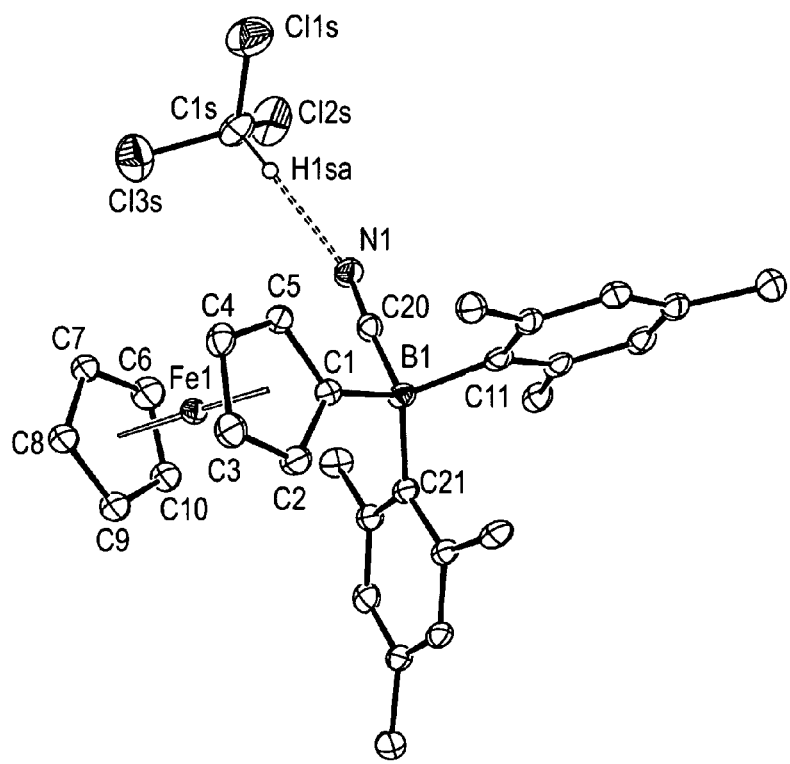
FIG. 13 shows the crystal structure of the organometallic compound 6a which is useful in the described detectors. The hydrogen atoms have been omitted for clarity and ORTEP ellipsoids set at the 50% probability level.
Figure 18:
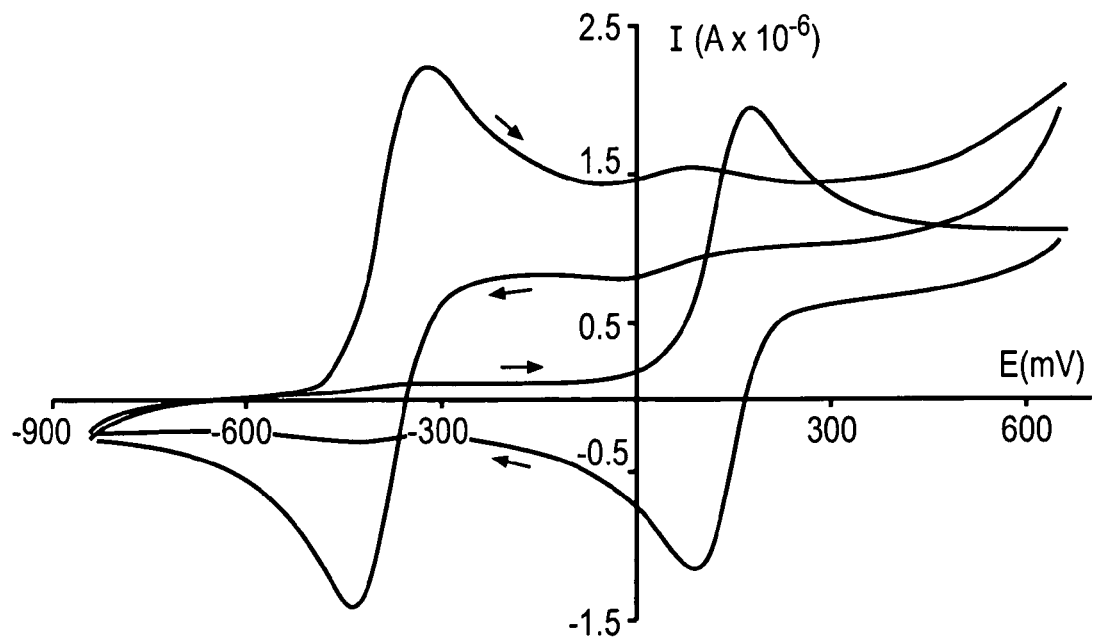
FIG. 18 shows cyclic voltammograms of acetonitrile solutions of compound 6a in the absence (right) and presence (left) of added cyanide ions.

Structural authentication of the mode of cyanide binding has been obtained by X-ray crystallography (FIG. 13) with the solid-state structure of crystals obtained from a mixed chloroform/hexanes solvent system revealing (i) an essentially linear C-bound cyanide complex with metrical parameters associated with the BCN unit in agreement with previous reports of cyanide/borane complexes [d(B—C)=1.621(3) Å, ∠B—C—N=169.8(3)°]; (ii) intermolecular hydrogen bonding between the cyanide nitrogen and a molecule of chloroform solvate [d(N . . . H)=2.143 Å; d(N . . . C)= 3.085 Å; ∠C—N . . . C=151.5°]; and (iii) significant elongation of the B—C$_{ipso}$ bond on cyanide binding [d(B—C$_{ipso}$)=1.639(4) Å, c.f. 1.546(7) Å and for the free receptor 6a]. The latter structural response is consistent with the conversion of a pendant three-coordinate boryl Lewis acid to an anionic four-coordinate borate, and is mirrored by changes in electrochemical behaviour. Thus, a cathodic shift of ca. −560 mV is measured for 6a in acetonitrile in the presence of cyanide (E$_{1/2}$=−383 (100) and +181 (80) mV with respect to FcH/FcH$^+$ for [6a.CN]$^-$ and 6a, respectively) (FIG. 18), which mirrors the behaviour of related ferrocene-derivatized Lewis acids on coordination of bases such as fluoride or trimethylphosphine.

A mixture of 6a (0.05 g, 0.12 mmol) and tetra-n-butylammonium cyanide dihydrate (1.1 equiv.) in [D]chloroform (5 mL) was stirred for 1 h, at which point the reaction was judged to be complete by $^{11}$B NMR spectroscopy (quantitative conversion to a single resonance at $\delta_B$ −16). Layering of the reaction mixture with diethyl ether led to the formation of [nBu$_4$N]$^{+[}$6a.CN]$^-$ as orange crystals suitable for X-ray diffraction (yield: 89%).

$^1$H NMR (300 MHz, [D]chloroform, 20° C.): δ 0.95 (m, 12H, CH$_3$ of″Bu$_4$N$^+$), 1.36 (m, 8H, CH$_2$ of″Bu$_4$N$^+$), 1.46 (m, 8H, CH$_2$ of ″Bu$_4$N$^+$), 2.09 (s, 18H, ortho- and para-CH$_3$ of Mes), 2.92 (m, 8H, CH$_2$ of″Bu$_4$N$^+$), 3.90 (s, 5H, Cp), 4.02 (s, 2H, CH of C$_5$H$_4$), 4.1 (s, 2H, CH of C$_5$H$_4$), 6.48 (s, 4H, aromatic CH of Mes).

$^{13}$C NMR (126 MHz, [D]chloroform, 20° C.): 13.8 (CH$_3$ of ["Bu$_4$N]$^+$), 19.8, 24.1 (CH$_2$ of ["Bu$_4$N]$^+$), 20.9 (para-CH$_3$ of Mes), 25.5 (br, ortho-CH$_3$ of Mes), 58.6 (NCH$_2$ of ["Bu$_4$N]$^+$), 68.1 (Cp), 67.4, 75.5 (C$_5$H$_4$), 128.9 (aromatic CH of Mes), 131.3 (para-quaternary of Mes), 141.7 (ortho-quaternary of Mes), 176.0 (CN$^-$), boron-bound quaternary carbons not observed.

[11]B (96 MHz, [D]chloroform, 20° C.): −16.1.

MS(ES neg): [6a.CN]$^-$=460.2 (100%), exact mass (calc. for [10]B, [54]Fe isotopomer) 457.1995, (obs.) 457.1988.

Elemental microanalysis: (calc. for C$_{46}$H$_{68}$BCl$_3$FeN$_2$ i.e. ["Bu$_4$N]$^{+}$[6a.CN]$^-$·CHCl$_3$) C, 67.21, H, 8.34, N, 3.41; (obs.) C, 66.83, H, 8.28, N, 3.23.

UV/Vis (CHCl$_3$): $\lambda_{max}$=460 nm, $\epsilon$=170 mol$^{-1}$ cm$^{-1}$ dm$^3$. IR (KBr): 2155 cm$^{-1}$ st, v(CN). E$_{1/2}$ vs. FcH/FcH$^+$ (peak-to-peak separation)=−383 (100) mV in CH$_3$CN.

Crystallographic data (for [nBu$_4$N]$^{+}$[6a.CN]$^-$·CHCl$_3$): C$_{46}$H$_{68}$BCl$_3$FeN$_2$, M$_r$=822.03, monoclinic, P2$_1$/c, a=11.9509(2), b=17.2939(2), c=21.5289(4) Å, β=92.344(1)°, V=4445.82(12) Å$^3$, Z=4, ρ$_c$=1.228 Mg m$^{-3}$, T=150(2) K, λ=0.71073 Å. 38935 reflections collected, 9981 independent [R(int)=0.0778], which were used in all calculations. R$_1$=0.0528, wR$_2$=0.1115 for observed unique reflections [F$^2$>2σ(F$^2$)] and R$_1$=0.1075, wR$_2$=0.1320 for all unique reflections. Max. and min. residual electron densities 0.51 and −0.46 e Å$^{-3}$.

Example 26

Data Characterizing the Response of 6b Towards Cyanide Ion (CN$^-$) Exposure (Formation of ["Bu$_4$N]$^{+}$[6b.CN]$^-$)

A mixture of 6b (0.05 g, 0.12 mmol) and tetra-n-butylammonium cyanide dihydrate (1.1 equiv) in [D]chloroform (5 mL) was stirred for 1 h after which time the reaction was deemed complete by $^{11}$B NMR spectroscopy quantitative conversion to a single resonance at δ$_B$ −16.8). Concentration of the reaction mixture and layering with diethylether led to the formation of ["Bu$_4$N]$^{+}$[6b.CN]$^-$ as orange microcrystals (yield: 91%).

$^1$H NMR (300 MHz, [D]chloroform, 20° C.): δ 0.96 (m, 12H, CH$_3$ of"Bu$_4$N$^+$), 1.34 (m, 8H, CH$_2$ of"Bu$_4$N$^+$), 1.47 (m, 8H, CH$_2$ of "Bu$_4$N$^+$), 1.75 s, 15H, Cp*), 1.95 (s, 6H, para-CH$_3$ of Mes), 2.06 (s, 12H, ortho-CH$_3$ of Mes), 2.94 (m, 8H, CH$_2$ of"Bu$_4$N$^+$), 3.52 (s, 2H, CH of C$_5$H$_4$), 3.68 (s, 2H, CH of C$_5$H$_4$), 6.43 (s, 4H, aromatic CH of Mes).

$^{13}$C NMR (126 MHz, [D$_6$]benzene, 20° C.): 15.5 (CH$_3$ of Cp*), 17.4 (CH$_3$ of ["Bu$_4$N]$^+$), 23.4, 27.5 (CH$_2$ of ["Bu$_4$N]$^+$), 24.7 (para-CH$_3$ of Mes), 30.0 (br, ortho-CH$_3$ of Mes), 61.6 (NCH$_2$ of ["Bu$_4$N]$^+$), 76.0, 81.2 (C$_5$H$_4$), 82.0 (quaternary of Cp*), 133.2 (aromatic CH of Mes), 134.6 (para-quaternary of Mes), 146.0 (ortho-quaternary of Mes), 175.6 (CN$^-$), boron-bound quaternary carbons not observed.

[11]B (96 MHz, [D]chloroform, 20° C.): =16.8.

MS(ES neg): [6b.CN]$^-$=530.4 (100%), exact mass (calc. for 56Fe, 10B isotopomer) 529.2730, (obs.) 529.2723.

UV/Vis (CH$_3$CN): $\lambda_{max}$=481 nm, $\epsilon$=295 mol$^{-1}$ cm$^{-1}$ dm$^3$.

IR (KBr): 2157 cm$^{-1}$ st, v(CN). E$_{1/2}$ vs. FcH/FcH$^+$ (peak-to-peak separation)=−691 (95) mV in CH$_3$CN.

Example 27

Crystallographic Data for Compound 6a

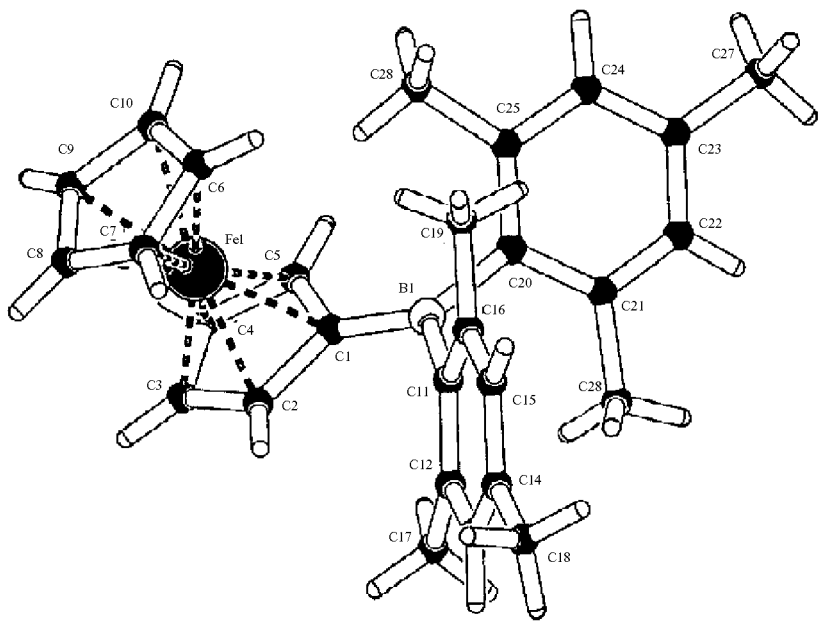

Crystal data and structure refinement details.

| | |
|---|---|
| Empirical formula | $C_{28}H_{31}BFe$ |
| Formula weight | 434.19 |
| Temperature | 120(2) K |
| Wavelength | 0.71073 Å |
| Crystal system | Monoclinic |
| Space group | $P2_1/n$ |
| Unit cell dimensions | a = 10.2980(4) Å  α = 90° |
| | b = 15.7275(8) Å  β = 104.958(3)° |
| | c = 14.0269(5) Å  γ = 90° |
| Volume | 2194.84(16) Å$^3$ |
| Z | 4 |
| Density (calculated) | 1.314 Mg/m$^3$ |
| Absorption coefficient | 0.699 mm$^{-1}$ |
| F(000) | 920 |
| Crystal | Plate; Red |
| Crystal size | 0.08 × 0.06 × 0.01 mm$^3$ |
| θ range for data collection | 2.99-25.03° |
| Index ranges | −12 ≤ h ≤ 12, −18 ≤ k ≤ 18, −16 ≤ l ≤ 16 |
| Reflections collected | 22801 |
| Independent reflections | 3855 [$R_{int}$ = 0.1177] |
| Completeness to θ = 25.03° | 99.7% |
| Absorption correction | Semi-empirical from equivalents |
| Max. and min. transmission | 0.9930 and 0.9462 |
| Refinement method | Full-matrix least-squares on F$^2$ |
| Data/restraints/parameters | 3855/0/277 |
| Goodness-of-fit on F$^2$ | 1.094 |
| Final R indices [F$^2$ > 2σ(F$^2$)] | R1 = 0.0658, wR2 = 0.1190 |
| R indices (all data) | R1 = 0.1189, wR2 = 0.1463 |
| Largest diff. peak and hole | 0.413 and −0.421 e Å$^{-3}$ |

Diffractometer:

Bruker-Nonius APEX II CCD camera (φ scans and ω scans to fill asymmetric unit).

Cell Determination:

DirAx (Duisenberg, A. J. M. (1992). J. Appl. Cryst. 25, 92-96.)

Data Collection:

Collect (Collect: Data collection software, R. Hooft, Nonius B. V., 1998).

Data Reduction and Cell Refinement:

Denzo (Z. Otwinowski & W. Minor, *Methods in Enzymology* (1997) Vol. 276: *Macromolecular Crystallography*, part A, pp. 307-326; C. W. Carter, Jr. & R. M. Sweet, Eds., Academic Press).

Absorption Correction:

Sheldrick, G. M. SADABS 2007/2—Bruker Nonius area detector scaling and absorption correction.

Structure Solution:

Sir2004 (Burla, M. C., Caliandro, R., Carrozzini, B., Cascarano, G., De Caro, L., Giacovazzo, C. & Polidori, G. (2004). J. Appl. Cryst. 37, 258).

Structure Refinement:

SHELXL97 (Sheldrick, G. M. (1997). University of Göttingen, Germany).

Graphics:

PLATON/PLUTON (Spek, A. L. (1990). Acta Cryst. A46, C34).

Special Details:

The hydrogen atoms were fixed as riding models.

TABLE 8

Atomic coordinates [×10$^4$], equivalent isotropic displacement parameters [Å$^2$ × 10$^3$] and site occupancy factors.

| Atom | x | y | z | $U_{eq}$ | S.o.f. |
|---|---|---|---|---|---|
| C1 | 2884(4) | 1381(3) | 1586(3) | 24(1) | 1 |
| C2 | 3023(5) | 2225(3) | 2011(4) | 29(1) | 1 |
| C3 | 3393(5) | 2802(3) | 1367(4) | 37(1) | 1 |
| C4 | 3525(5) | 2341(4) | 528(4) | 38(1) | 1 |
| C5 | 3233(5) | 1477(4) | 661(4) | 31(1) | 1 |
| C6 | 6286(5) | 1102(3) | 2615(4) | 32(1) | 1 |
| C7 | 6189(5) | 1858(4) | 3145(4) | 32(1) | 1 |
| C8 | 6442(5) | 2547(3) | 2574(4) | 31(1) | 1 |
| C9 | 6678(5) | 2224(3) | 1687(4) | 29(1) | 1 |
| C10 | 6593(5) | 1323(3) | 1727(4) | 28(1) | 1 |
| C11 | 2129(4) | 630(3) | 3092(3) | 23(1) | 1 |
| C12 | 1204(5) | 1183(3) | 3356(7) | 25(1) | 1 |
| C13 | 1005(5) | 1146(3) | 4304(4) | 28(1) | 1 |
| C14 | 1687(5) | 586(3) | 5018(3) | 27(1) | 1 |
| C15 | 2630(5) | 55(3) | 4764(3) | 28(1) | 1 |
| C16 | 2861(5) | 69(3) | 3832(3) | 24(1) | 1 |
| C17 | 327(4) | 1804(3) | 2644(3) | 29(1) | 1 |
| C18 | 1459(5) | 554(3) | 6037(4) | 35(1) | 1 |
| C19 | 3929(5) | −508(3) | 3630(4) | 30(1) | 1 |
| C20 | 1996(5) | −273(3) | 1412(3) | 23(1) | 1 |
| C21 | 651(5) | −576(3) | 1194(3) | 24(1) | 1 |
| C22 | 283(5) | −1328(3) | 699(3) | 24(1) | 1 |
| C23 | 1190(4) | −1859(3) | 410(3) | 23(1) | 1 |
| C24 | 2517(5) | −1569(3) | 605(3) | 25(1) | 1 |
| C25 | 2914(5) | −795(3) | 1081(3) | 25(1) | 1 |
| C26 | −463(5) | −64(3) | 1450(4) | 29(1) | 1 |
| C27 | 772(5) | −2690(3) | −88(4) | 28(1) | 1 |
| C28 | 4387(5) | −572(3) | 1247(4) | 30(1) | 1 |
| Fe1 | 4813(1) | 1880(1) | 1793(1) | 25(1) | 1 |
| B1 | 2384(5) | 584(4) | 2029(4) | 23(1) | 1 |

$U_{eq}$ is defined as one third of the trace of the orthogonalized $U^{ij}$ tensor.

TABLE 9

Bond lengths [Å] and angles [°].

| | |
|---|---|
| C1—C5 | 1.441(7) |
| C1—C2 | 1.447(7) |
| C1—B1 | 1.546(7) |
| C1—Fe1 | 2.085(5) |
| C2—C3 | 1.401(7) |
| C2—Fe1 | 2.019(5) |
| C2—H2 | 0.9500 |
| C3—C4 | 1.417(8) |
| C3—Fe1 | 2.037(5) |
| C3—H3 | 0.9500 |
| C4—C5 | 1.414(7) |
| C4—Fe1 | 2.054(5) |
| C4—H4 | 0.9500 |
| C5—Fe1 | 2.058(5) |
| C5—H5 | 0.9500 |
| C6—C10 | 1.405(7) |
| C6—C7 | 1.420(7) |
| C6—Fe1 | 2.055(5) |
| C6—H6 | 0.9500 |
| C7—C8 | 1.410(7) |
| C7—Fe1 | 2.053(5) |
| C7—H7 | 0.9500 |
| C8—C9 | 1.423(7) |
| C8—Fe1 | 2.041(5) |
| C8—H8 | 0.9500 |
| C9—C10 | 1.422(7) |
| C9—Fe1 | 2.038(5) |
| C9—H9 | 0.9500 |
| C10—Fe1 | 2.056(5) |
| C10—H10 | 0.9500 |
| C11—C12 | 1.408(7) |
| C11—C16 | 1.420(6) |
| C11—B1 | 1.581(7) |
| C12—C13 | 1.398(7) |
| C12—C17 | 1.517(6) |
| C13—C14 | 1.382(7) |
| C13—H13 | 0.9500 |
| C14—C15 | 1.394(7) |

TABLE 9-continued

Bond lengths [Å] and angles [°].

| | |
|---|---|
| C14—C18 | 1.507(7) |
| C15—C16 | 1.388(7) |
| C15—H15 | 0.9500 |
| C16—C19 | 1.509(7) |
| C17—H17A | 0.9800 |
| C17—H17B | 0.9800 |
| C17—H17C | 0.9800 |
| C18—H18A | 0.9800 |
| C18—H18B | 0.9800 |
| C18—H18C | 0.9800 |
| C19—H19A | 0.9800 |
| C19—H19B | 0.9800 |
| C19—H19C | 0.9800 |
| C20—C21 | 1.421(6) |
| C20—C25 | 1.417(7) |
| C20—B1 | 1.597(7) |
| C21—C22 | 1.375(7) |
| C21—C26 | 1.518(7) |
| C22—C23 | 1.388(7) |
| C22—H22 | 0.9500 |
| C23—C24 | 1.400(6) |
| C23—C27 | 1.492(6) |
| C24—C25 | 1.398(7) |
| C24—H24 | 0.9500 |
| C25—C28 | 1.515(6) |
| C26—H26A | 0.9800 |
| C26—H26B | 0.9800 |
| C26—H26C | 0.9800 |
| C27—H27A | 0.9800 |
| C27—H27B | 0.9800 |
| C27—H27C | 0.9800 |
| C28—H28A | 0.9800 |
| C28—H28B | 0.9800 |
| C28—H28C | 0.9800 |
| C5—C1—C2 | 104.7(4) |
| C5—C1—B1 | 129.3(5) |
| C2—C1—B1 | 125.9(4) |
| C5—C1—Fe1 | 68.7(3) |
| C2—C1—Fe1 | 66.9(3) |
| B1—C1—Fe1 | 130.8(3) |
| C3—C2—C1 | 110.0(5) |
| C3—C2—Fe1 | 70.5(3) |
| C1—C2—Fe1 | 71.8(3) |
| C3—C2—H2 | 125.0 |
| C1—C2—H2 | 125.0 |
| Fe1—C2—H2 | 124.3 |
| C2—C3—C4 | 107.7(5) |
| C2—C3—Fe1 | 69.1(3) |
| C4—C3—Fe1 | 70.4(3) |
| C2—C3—H3 | 126.1 |
| C4—C3—H3 | 126.1 |
| Fe1—C3—H3 | 125.9 |
| C3—C4—C5 | 108.2(5) |
| C3—C4—Fe1 | 69.1(3) |
| C5—C4—Fe1 | 70.0(3) |
| C3—C4—H4 | 125.9 |
| C5—C4—H4 | 125.9 |
| Fe1—C4—H4 | 126.6 |
| C4—C5—C1 | 109.3(5) |
| C4—C5—Fe1 | 69.7(3) |
| C1—C5—Fe1 | 70.6(3) |
| C4—C5—H5 | 125.4 |
| C1—C5—H5 | 125.4 |
| Fe1—C5—H5 | 125.9 |
| C10—C6—C7 | 108.6(5) |
| C10—C6—Fe1 | 70.0(3) |
| C7—C6—Fe1 | 69.7(3) |
| C10—C6—H6 | 125.7 |
| C7—C6—H6 | 125.7 |
| Fe1—C6—H6 | 126.1 |
| C8—C7—C6 | 107.4(4) |
| C8—C7—Fe1 | 69.4(3) |
| C6—C7—Fe1 | 69.9(3) |
| C8—C7—H7 | 126.3 |
| C6—C7—H7 | 126.3 |
| Fe1—C7—H7 | 126.0 |
| C7—C8—C9 | 108.6(5) |
| C7—C8—Fe1 | 70.3(3) |
| C9—C8—Fe1 | 69.4(3) |
| C7—C8—H8 | 125.7 |
| C9—C8—H8 | 125.7 |
| Fe1—C8—H8 | 126.1 |
| C8—C9—C10 | 107.2(5) |
| C8—C9—Fe1 | 69.7(3) |
| C10—C9—Fe1 | 70.4(3) |
| C8—C9—H9 | 126.4 |
| C10—C9—H9 | 126.4 |
| Fe1—C9—H9 | 125.1 |
| C6—C10—C9 | 108.1(5) |
| C6—C10—Fe1 | 70.0(3) |
| C9—C10—Fe1 | 69.0(3) |
| C6—C10—H10 | 125.9 |
| C9—C10—H10 | 125.9 |
| Fe1—C10—H10 | 126.6 |
| C12—C11—C16 | 117.3(4) |
| C12—C11—B1 | 124.3(4) |
| C16—C11—B1 | 118.3(4) |
| C13—C12—C11 | 119.9(4) |
| C13—C12—C17 | 116.4(4) |
| C11—C12—C17 | 123.6(4) |
| C14—C13—C12 | 123.0(5) |
| C14—C13—H13 | 118.5 |
| C12—C13—H13 | 118.5 |
| C13—C14—C15 | 116.9(5) |
| C13—C14—C18 | 122.2(5) |
| C15—C14—C18 | 120.8(4) |
| C16—C15—C14 | 122.1(4) |
| C16—C15—H15 | 119.0 |
| C14—C15—H15 | 119.0 |
| C15—C16—C11 | 120.7(5) |
| C15—C16—C19 | 118.5(4) |
| C11—C16—C19 | 120.8(4) |
| C12—C17—H17A | 109.5 |
| C12—C17—H17B | 109.5 |
| H17A—C17—H17B | 109.5 |
| C12—C17—H17C | 109.5 |
| H17A—C17—H17C | 109.5 |
| H17B—C17—H17C | 109.5 |
| C14—C18—H18A | 109.5 |
| C14—C18—H18B | 109.5 |
| H18A—C18—H18B | 109.5 |
| C14—C18—H18C | 109.5 |
| H18A—C18—H18C | 109.5 |
| H18B—C18—H18C | 109.5 |
| C16—C19—H19A | 109.5 |
| C16—C19—H19B | 109.5 |
| H19A—C19—H19B | 109.5 |
| C16—C19—H19C | 109.5 |
| H19A—C19—H19C | 109.5 |
| H19B—C19—H19C | 109.5 |
| C21—C20—C25 | 115.5(4) |
| C21—C20—B1 | 119.6(4) |
| C25—C20—B1 | 124.9(4) |
| C22—C21—C20 | 121.5(4) |
| C22—C21—C26 | 116.7(4) |
| C20—C21—C26 | 121.7(4) |
| C21—C22—C23 | 123.2(4) |
| C21—C22—H22 | 118.4 |
| C23—C22—H22 | 118.4 |
| C22—C23—C24 | 116.3(4) |
| C22—C23—C27 | 121.9(4) |
| C24—C23—C27 | 121.8(4) |
| C25—C24—C23 | 121.9(5) |
| C25—C24—H24 | 119.0 |
| C23—C24—H24 | 119.0 |
| C24—C25—C20 | 121.5(4) |
| C24—C25—C28 | 115.7(4) |
| C20—C25—C28 | 122.8(4) |
| C21—C26—H26A | 109.5 |
| C21—C26—H26B | 109.5 |
| H26A—C26—H26B | 109.5 |
| C21—C26—H26C | 109.5 |
| H26A—C26—H26C | 109.5 |
| H26B—C26—H26C | 109.5 |
| C23—C27—H27A | 109.5 |
| C23—C27—H27B | 109.5 |

TABLE 9-continued

Bond lengths [Å] and angles [°].

| | |
|---|---|
| H27A—C27—H27B | 109.5 |
| C23—C27—H27C | 109.5 |
| H27A—C27—H27C | 109.5 |
| H27B—C27—H27C | 109.5 |
| C25—C28—H28A | 109.5 |
| C25—C28—H28B | 109.5 |
| H28A—C28—H28B | 109.5 |
| C25—C28—H28C | 109.5 |
| H28A—C28—H28C | 109.5 |
| H28B—C28—H28C | 109.5 |
| C2—Fe1—C3 | 40.4(2) |
| C2—Fe1—C9 | 148.7(2) |
| C3—Fe1—C9 | 114.1(2) |
| C2—Fe1—C8 | 115.9(2) |
| C3—Fe1—C8 | 102.7(2) |
| C9—Fe1—C8 | 40.8(2) |
| C2—Fe1—C7 | 107.7(2) |
| C3—Fe1—C7 | 123.7(2) |
| C9—Fe1—C7 | 68.4(2) |
| C8—Fe1—C7 | 40.3(2) |
| C2—Fe1—C6 | 130.2(2) |
| C3—Fe1—C6 | 163.5(2) |
| C9—Fe1—C6 | 68.0(2) |
| C8—Fe1—C6 | 67.7(2) |
| C7—Fe1—C6 | 40.4(2) |
| C2—Fe1—C4 | 68.0(2) |
| C3—Fe1—C4 | 40.5(2) |
| C9—Fe1—C4 | 104.7(2) |
| C8—Fe1—C4 | 122.7(2) |
| C7—Fe1—C4 | 160.3(2) |
| C6—Fe1—C4 | 155.5(2) |
| C2—Fe1—C10 | 168.9(2) |
| C3—Fe1—C10 | 150.6(2) |
| C9—Fe1—C10 | 40.6(2) |
| C8—Fe1—C10 | 68.0(2) |
| C7—Fe1—C10 | 67.9(2) |
| C6—Fe1—C10 | 40.0(2) |
| C4—Fe1—C10 | 119.7(2) |
| C2—Fe1—C5 | 68.2(2) |
| C3—Fe1—C5 | 68.1(2) |
| C9—Fe1—C5 | 126.7(2) |
| C8—Fe1—C5 | 161.6(2) |
| C7—Fe1—C5 | 158.0(2) |
| C6—Fe1—C5 | 124.9(2) |
| C4—Fe1—C5 | 40.2(2) |
| C10—Fe1—C5 | 111.8(2) |
| C2—Fe1—C1 | 41.25(19) |
| C3—Fe1—C1 | 69.0(2) |
| C9—Fe1—C1 | 166.36(19) |
| C8—Fe1—C1 | 152.8(2) |
| C7—Fe1—C1 | 121.89(19) |
| C6—Fe1—C1 | 113.1(2) |
| C4—Fe1—C1 | 68.5(2) |
| C10—Fe1—C1 | 131.46(19) |
| C5—Fe1—C1 | 40.69(19) |
| C1—B1—C11 | 119.7(4) |
| C1—B1—C20 | 122.0(4) |
| C11—B1—C20 | 118.1(4) |

TABLE 10

Anisotropic displacement parameters [Å$^2$ × 10$^3$].

| Atom | U$^{11}$ | U$^{22}$ | U$^{33}$ | U$^{23}$ | U$^{13}$ | U$^{12}$ |
|---|---|---|---|---|---|---|
| C1 | 18(2) | 29(3) | 23(3) | 1(2) | 1(2) | 0(2) |
| C2 | 22(3) | 25(3) | 41(3) | 1(2) | 10(2) | 4(2) |
| C3 | 23(3) | 25(3) | 61(4) | 17(3) | 7(3) | 5(2) |
| C4 | 21(3) | 48(4) | 40(3) | 21(3) | −3(2) | −2(2) |
| C5 | 18(3) | 43(3) | 28(3) | 1(2) | −2(2) | −3(2) |
| C6 | 24(3) | 31(3) | 35(3) | 2(2) | −6(2) | 0(2) |
| C7 | 24(3) | 45(3) | 25(3) | −6(3) | 4(2) | −3(2) |
| C8 | 26(3) | 30(3) | 35(3) | −6(2) | 4(2) | −5(2) |
| C9 | 18(3) | 40(3) | 31(3) | −4(2) | 7(2) | −4(2) |
| C10 | 21(3) | 29(3) | 30(3) | −5(2) | 3(2) | 2(2) |
| C11 | 22(2) | 16(2) | 26(3) | −2(2) | 0(2) | −4(2) |

TABLE 10-continued

Anisotropic displacement parameters [Å$^2$ × 10$^3$].

| Atom | U$^{11}$ | U$^{22}$ | U$^{33}$ | U$^{23}$ | U$^{13}$ | U$^{12}$ |
|---|---|---|---|---|---|---|
| C12 | 24(3) | 22(3) | 26(3) | −2(2) | 2(2) | −3(2) |
| C13 | 25(3) | 27(3) | 33(3) | −5(2) | 9(2) | −4(2) |
| C14 | 26(3) | 28(3) | 26(3) | −2(2) | 5(2) | −4(2) |
| C15 | 32(3) | 25(3) | 22(3) | 3(2) | 1(2) | −2(2) |
| C16 | 19(2) | 20(3) | 32(3) | −4(2) | 3(2) | −6(2) |
| C17 | 22(2) | 28(3) | 35(3) | 0(2) | 4(2) | 1(2) |
| C18 | 41(3) | 39(3) | 28(3) | −2(2) | 13(2) | 3(3) |
| C19 | 32(3) | 23(3) | 30(3) | 3(2) | 2(2) | −1(2) |
| C20 | 22(3) | 24(3) | 23(2) | −1(2) | 4(2) | 2(2) |
| C21 | 25(3) | 27(3) | 19(2) | 4(2) | 2(2) | 5(2) |
| C22 | 21(2) | 26(3) | 22(2) | 3(2) | 2(2) | −3(2) |
| C23 | 27(2) | 23(3) | 17(2) | 5(2) | 0(2) | −3(2) |
| C24 | 29(3) | 21(3) | 24(2) | 0(2) | 7(2) | 4(2) |
| C25 | 22(2) | 29(3) | 22(2) | 2(2) | 2(2) | −4(2) |
| C26 | 21(3) | 33(3) | 31(3) | −2(2) | 2(2) | 1(2) |
| C27 | 31(3) | 22(3) | 29(3) | −5(2) | 2(2) | 0(2) |
| C28 | 31(3) | 24(3) | 34(3) | −3(2) | 8(2) | 3(2) |
| Fe1 | 21(1) | 24(1) | 29(1) | 2(1) | 3(1) | −1(1) |
| B1 | 15(3) | 27(3) | 25(3) | 1(2) | 1(2) | 2(2) |

The anisotropic displacement factor exponent takes the form: $-2\pi^2[h^2a^{*2}U^{11}+\ldots+2hka^*b^*U^{12}]$.

TABLE 11

Hydrogen coordinates [×10$^4$] and isotropic displacement parameters [Å$^2$ × 10$^3$].

| Atom | x | y | z | U$_{eq}$ | S.o.f. |
|---|---|---|---|---|---|
| H2 | 2884 | 2368 | 2635 | 35 | 1 |
| H3 | 3531 | 3396 | 1472 | 45 | 1 |
| H4 | 3768 | 2573 | −27 | 46 | 1 |
| H5 | 3261 | 1031 | 211 | 38 | 1 |
| H6 | 6164 | 540 | 2825 | 39 | 1 |
| H7 | 5991 | 1894 | 3768 | 38 | 1 |
| H8 | 6452 | 3131 | 2753 | 37 | 1 |
| H9 | 6859 | 2549 | 1165 | 35 | 1 |
| H10 | 6721 | 937 | 1238 | 33 | 1 |
| H13 | 373 | 1523 | 4465 | 34 | 1 |
| H15 | 3130 | −328 | 5244 | 33 | 1 |
| H17A | −619 | 1698 | 2616 | 43 | 1 |
| H17B | 472 | 1730 | 1986 | 43 | 1 |
| H17C | 563 | 2387 | 2871 | 43 | 1 |
| H18A | 2231 | 808 | 6511 | 53 | 1 |
| H18B | 1355 | −38 | 6219 | 53 | 1 |
| H18C | 643 | 873 | 6041 | 53 | 1 |
| H19A | 4496 | −722 | 4256 | 45 | 1 |
| H19B | 4483 | −190 | 3281 | 45 | 1 |
| H19C | 3500 | −988 | 3222 | 45 | 1 |
| H22 | −635 | −1493 | 547 | 28 | 1 |
| H24 | 3167 | −1908 | 409 | 30 | 1 |
| H26A | −1324 | −355 | 1194 | 44 | 1 |
| H26B | −504 | 502 | 1152 | 44 | 1 |
| H26C | −280 | −10 | 2168 | 44 | 1 |
| H27A | 1084 | −3154 | 382 | 43 | 1 |
| H27B | 1168 | −2752 | −649 | 43 | 1 |
| H27C | −210 | −2710 | −323 | 43 | 1 |
| H28A | 4925 | −924 | 1781 | 44 | 1 |
| H28B | 4523 | 30 | 1429 | 44 | 1 |
| H28C | 4666 | −676 | 640 | 44 | 1 |

Example 28

Binding constant determination for compound 6a with fluoride in dichloromethane.

Binding constants were determined using the method reported by Gabbai, (S. Sole and F. P. Gabbai, Chem. Commun., 2004, 1284-1285) using the program LabFit (www-.labfit.net). Experimental data of Abs/Abs$_o$ vs. [F$^-$] were fitted to the expression $$Abs/Abs_o = Y = (0.5/A)*(A-X-1/B+[(A+X+1/B)**2-4*A*X)**0.5$$

Where A=[FcBMes$_2$]$_o$ and B=K$_F$ associated with the reaction:

i.e. K$_F$=[FCBMeS$_2$F$^-$]/[FCBMeS$_2$][F$^-$]

Figure 14:
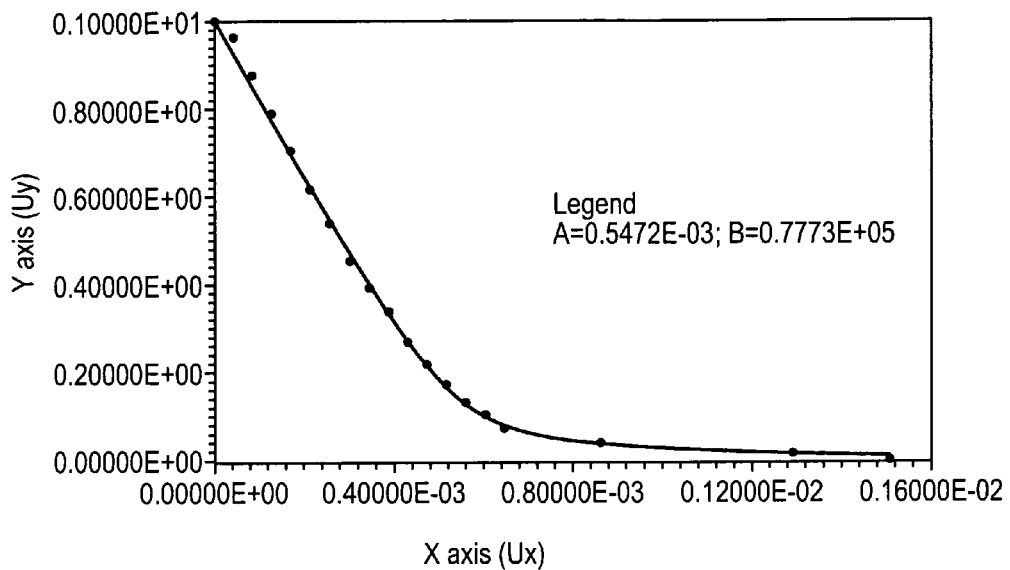
FIG. 14 shows the plot used for determining the binding constant of compound 6a in the presence of F$^-$ anions.

FIG. 14 shows experimental data (points) and the best-fit line obtained using the above expression (A=5.5×10$^{-4}$), B=(7.8×10$^4$), R$^2$=0.9987. Hence K$_F$=7.8(1.2)×10$^4$ mol$^{-1}$ dm$^3$.

Example 29

Binding constant determination for 6a with cyanide in dichloromethane.

The binding constant of 6a for cyanide in dichloromethane (K$_{CN}$) was evaluated in an analogous manner to K$_F$ in Example 28.

FIG. 15 shows experimental data (points) and the best-fit line obtained using the above expression (A=7.9×10$^-$), B=(3.5×10$^4$), R$^2$=0.9987. Hence K$_{CN}$=3.5(0.4)×10$^4$ mol$^{-1}$ dm$^3$.

Example 30

Demonstration of a detector system suitable for distinguishing between F$^-$ and CN$^-$ analytes.

While the redox potential measured for [6a.CN]$^-$ is not compatible with oxidation by atmospheric oxygen, the use of the pentamethylated analogue 6b results in a ca. −300 mV cathodic shift in the redox potentials of both the free receptor and the cyanide adduct. Thus, 6b and [6b.CN]$^-$ are oxidized at −176(75) and −691(95) mV (with respect to FcH/FcH$^+$), thereby offering a convenient electrochemical window for choice of a redox-matched oxidant which will oxidize the desired cyanide adduct but not the 'free' receptor. The tetrazolium dyes, offer a range of compatible redox potentials and offer a vastly enhanced change in extinction coefficient (and hence greater sensitivity) than atmospheric oxygen. The results of monitoring the exposure of 6b to either cyanide or fluoride, in the presence of the compatible redox-active dye tetrazolium violet, by UV/Visible spectroscopy are shown in FIGS. 17a, 17b. Furthermore, a significant colour change is observed on exposure of solutions of 6b in acetonitrile/methanol (Solution mainly acetonitrile, but trace of methanol to aid solubility) to fluoride and cyanide ions in the presence of MTT.

Each sample contains ca 1 mg tetrazolium violet in acetonitrile/methanol (>100:1) and ca. 3 mg of each of the compounds 1$^{s*}$ and 6b.

One sample containing compound 1$^{s*}$ and one containing compound 6b then had excess cyanide added (6b changes colour but not 1s*). One sample containing compound 1$^{s*}$ and one containing compound 6b had excess fluoride added (both change colour). One sample containing compound 1$^{s*}$ and one containing compound 6b had excess chloride added (control reaction—neither changes colour)

On exposure to cyanide ions, the pale pink solution of 6b+MTT turns rapidly dark purple and in the presence of fluoride ions it turns rapidly deep blue. In each case, the reaction of the compounds was tested in the presence of ca. 1 mM of F$^-$ or CN$^-$ ions.

Compound 6b is shown to give a colorimetric response on exposure to either fluoride or cyanide.

The competing sensor response of compounds 6a and 6b with fluoride can readily be understood in terms of the known (high) B—F bond strength and quantified by a binding constant for 6a with fluoride in dichloromethane solution (determined from UV/Vis based titration data) of 7.8(1.2)×10$^4$ mol$^{-1}$ dm$^3$ (FIG. 14). This figure is comparable to that measured for cyanide and similar to that measured by Solé and Gabbaï for the related Lewis acid BMes$_3$ in tetrahydrofuran [3.3(0.4)×10$^5$ mol$^{-1}$ dm$^3$]. Although the positive sensor responses demonstrated by dimesitylboryl complexes 6a and 6b are characteristic of either fluoride or cyanide, discrimination can be achieved by the use of a weaker Lewis acid receptor.

Figure 17C:
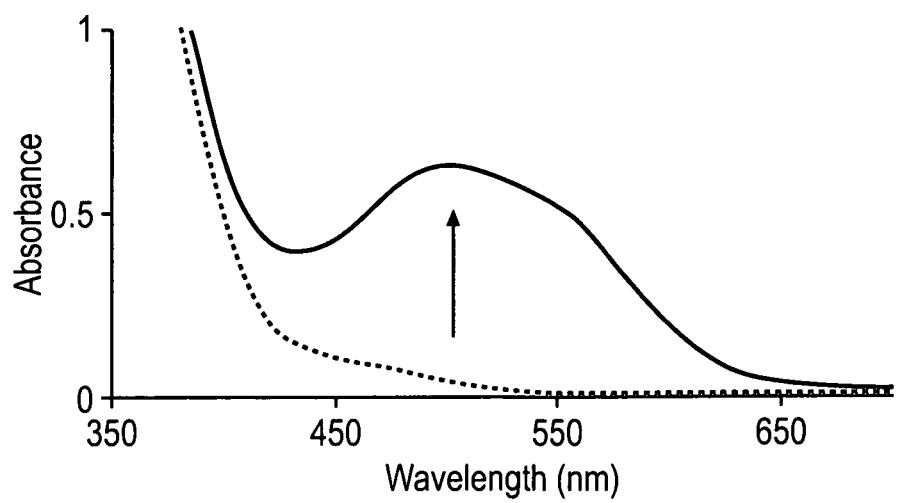
Figure 17D:
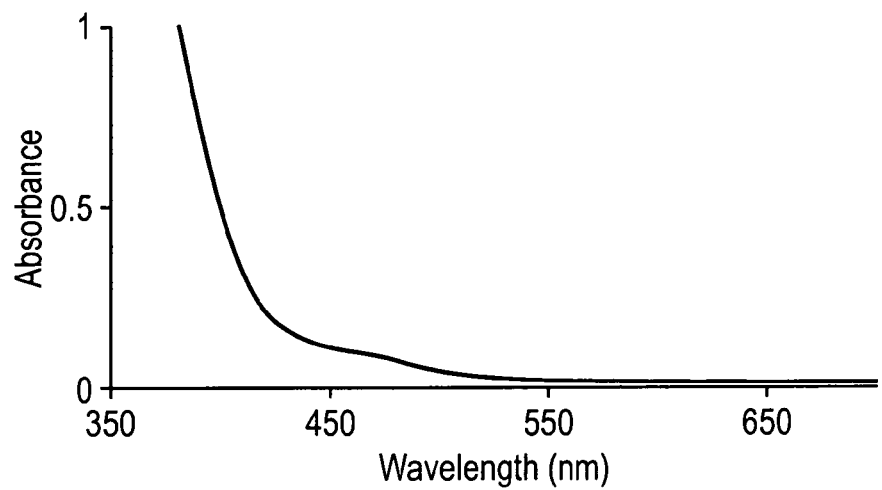

Dialkoxy arylboronic esters have been shown to display a unique binding affinity for fluoride, and the pentamethylferrocene-functionalized stilbene diolate analogue of 6b, Fc*B(OR)$_2$ [1$^{s*}$: (OR)$_2$=S,S—OCH(Ph)CH(Ph)O] undergoes a −580 mV electrochemical shift on fluoride binding [from −169(80) to −749(95) mV with respect to FcH/FcH$^+$]. In combination with the same tetrazolium violet redox dye in the presence of MTT, a colorimetric response is observed on exposure of 1$^{s*}$ to fluoride (the nearly clear solution of 1$^{s*}$+MTT in acetonitrile/methanol turns quickly grey/blue on exposure to fluoride ions). By contrast, a null response is observed when excess cyanide is added to solutions of 1$^{s*}$ in acetonitrile/methanol under identical conditions (FIGS. 17c and 17d).

Thus, while the stronger Lewis acid 6b gives positive colorimetric responses to both cyanide AND fluoride, 1$^{s*}$ senses fluoride but NOT cyanide under the same conditions.

Scheme 1: Synthetic routes to ferrocene functionalised boronic esters from known compounds of the types FeC$_{10}$H$_{10-x}$(BBr$_2$)$_x$ (x = 1, 2, 4) and FeC$_{10}$H$_{10-x}$[B(OH)$_2$]$_x$ (x = 1, 2). Ethyltris(boryl) systems (3) were synthesized by analogous routes from the known compound 1-Et-1', 3, 3'-(BBr$_2$)$_3$($\eta^5$-C$_5$H$_3$)$_2$Fe [literature preparations of starting materials: FcBBr$_2$ T. Renk, W. Ruf, W. Siebert, J. Organomet. Chem. 120 (1976) 1; Fc(BBr$_2$)$_2$ B. Wrackmeyer, U. Dörfler, W. Milius, M. Herberhold, Z. Naturforsch., Teil B. 51 (1996) 851; EtFc(BBr$_2$)$_3$ K. Ma, M. Scheibitz, S. Scholz, M. Wagner, J. Organomet. Chem. 652 (2002) 11; Fc(BBr$_2$)$_4$ A. Appel, H. Nöth, M. Schmidt, Chem. Ber. 128 (1995) 621; FcB(OH)$_2$ S. McVey, I. G. Morrison, P. L. Pauson, J. Chem. Soc. C (1967) 1847; Fc[B(OH)$_2$]$_2$ R. Knapp, M. Rehahn, J. Organomet. Chem. 452 (1993) 235; Fc = ferrocenyl core, FeC$_{10}$H$_{10-x}$].

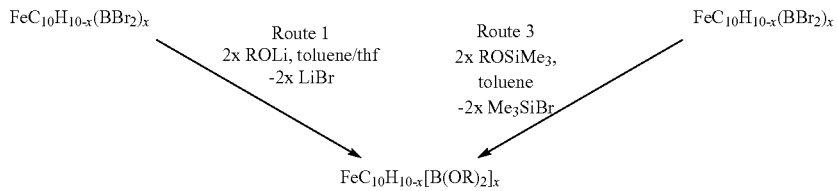

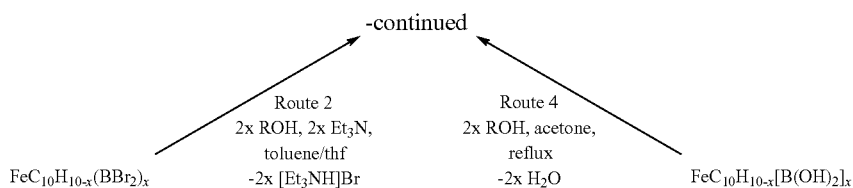

Scheme 2: Mode of action of 2⁵ as a calorimetric fluoride ion sensor.

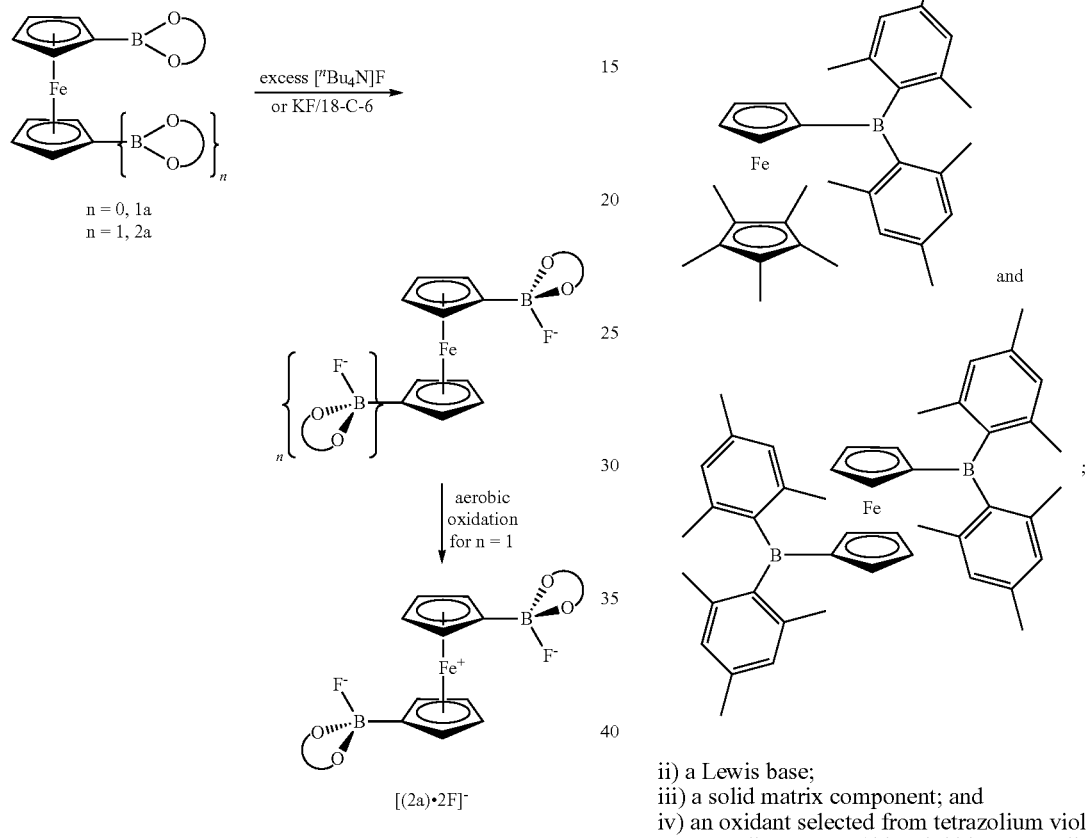

The invention claimed is:

1. A detector for detecting an analyte compound which is a fluorine-containing compound or a cyanide-containing compound, said detector comprising:
   i) an organometallic compound selected from the group consisting of

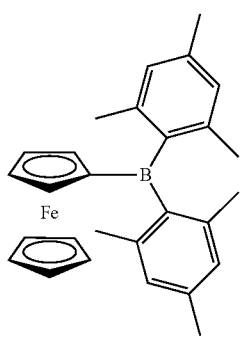

ii) a Lewis base;
   iii) a solid matrix component; and
   iv) an oxidant selected from tetrazolium violet, nitro blue tetrazolium, MTT (thiazolyl blue tetrazolium bromide), 5-cyano-2,3-bis(4-methylphenyl)-2H-tetrazolium chloride (CTC), 2,3,5-triphenyl-tetrazolium chloride, and derivatives thereof.

2. A detector according to claim 1 for detection of an analyte that is a fluorine-containing compound, wherein in the presence of the analyte, the organometallic compound forms a complex with one or more fluorine atoms from the analyte to produce a detectable change.

3. A detector according to claim 2, wherein the detectable change is selected from: a color change, a change in the electronic or infrared spectrum, or a change in electrochemical behavior.

4. A detector according to claim 2, wherein the detectable change is quantitatively related to an amount of fluorine-containing compound.

5. A detector according to claim 1, wherein in the presence of a fluorine-containing compound, the organometallic compound forms a complex with one or more fluorine atoms from the fluorine-containing compound to produce a detectable change, and the oxidant oxidizes the complex formed by the organometallic compound in the presence of the one or more fluorine atoms or cyanide groups, but does not oxidize the organometallic compound alone.

6. A detector according to claim 1, wherein in the presence of a cyanide-containing compound, the organometallic compound forms a complex with one or more cyanide groups from the cyanide-containing compound to produce a detectable change, and the oxidant oxidizes the complex formed by the organometallic compound in the presence of the one or more cyanide groups, but does not oxidize the organometallic compound alone.

7. A detector according to claim 1, wherein in the presence of a fluorine-containing compound, the organometallic compound forms a complex with one or more fluorine atoms from the fluorine-containing compound to produce a detectable change, in the presence of a cyanide-containing compound, the organometallic compound forms a complex with one or more cyanide groups from the cyanide-containing compound to produce a detectable change, and the oxidant oxidizes the complex formed by the organometallic compound in the presence of the one or more fluorine atoms or cyanide groups, but does not oxidize the organometallic compound alone.

8. A detector according to claim 1, wherein the organometallic compound is a first organometallic compound and the detector further comprises a second organometallic compound,
wherein in the presence of an analyte which is a cyanide-containing compound, the second organometallic compound does not form a complex with one or more cyanide groups from the analyte and therefore does not produce a detectable change, and in the presence of an analyte which is a fluoride-containing compound, the first organometallic compound and the second organometallic compound each form a complex with one or more fluoride groups from the analyte and therefore do produce a detectable change.

9. A detector according to claim 1, further comprising hydrolysis catalyst which catalyzes release of a fluorine atom or cyanide group from a fluorine-containing compound or cyanide-containing compound respectively.

10. A detector according to claim 1, wherein the Lewis base and the solid matrix component are a single component comprising a Lewis basic solid matrix component.

11. A detector according to claim 1, which is suitable for detecting an analyte selected from:
hydrogen fluoride gas;
hydrofluoric acid;
an acetyl fluoride compound;
sulphur tetrafluoride;
diethylamino sulphur trifluoride;
cyanogen fluoride;
fluoropyridinium salts;
methylphosphonofluoridic acid, 1-methylethylester (GB, Sarin);
methylphosphonofluoridic, 1,2,2-trimethylpropyl ester (GD, Soman);
methylphosphonofluoridic, cyclohexylester (GF, cyclohexylsarin);
alkylphosphonofluoridic, alkylester or arylester; and
dialkylfluorophosphates (DFPs).

12. A detector according to claim 1, which is suitable for detecting an analyte selected from:
hydrogen cyanide;
Tabun (CA) (ethyl N,N-dimethylphosphoramidocyanidate);
cyanogen;
cyanogen fluoride;
cyanogen chloride (CK);
cyanogen bromide;
cyanogen iodide; and
cyanogen azide.

13. A method of sample analysis comprising the steps of:
a) exposing a detector according to claim 1 to a sample which may or may not contain a fluorine-containing compound and/or a cyanide-containing compound;
b) identifying the presence or absence of a detectable change in the detector;
c) correlating the presence or absence of the detectable change in the detector with the presence or absence of a fluorine-containing compound and/or a cyanide containing compound; and
d) providing an output to indicate the presence or absence of a fluorine-containing compound and/or a cyanide containing compound.

14. A method according to claim 13, wherein the correlating step c) is quantitative and wherein the output in step d) indicates the amount of fluorine-containing compound or cyanide containing compound present in the sample.

15. A method according to claim 13, wherein the sample may contain a fluorine-containing compound selected from:
hydrogen fluoride gas;
hydrofluoric acid;
an acetyl fluoride compound;
sulphur tetrafluoride;
diethylamino sulphur trifluoride;
cyanogen fluoride;
fluoropyridinium salts;
methylphosphonofluoridic acid, 1-methylethylester (GB, Sarin);
methylphosphonofluoridic, 1,2,2-trimethylpropyl ester (GD, Soman);
methylphosphonofluoridic, cyclohexylester (GF, cyclohexylsarin);
alkylphosphonofluoridic, alkylester or arylester; and
dialkylfluorophosphates (DFPs).

16. A method according to claim 13, wherein the sample may contain a cyanide-containing compound selected from:
hydrogen cyanide;
Tabun (CA) (ethyl N,N-dimethylphosphoramidocyanidate);
cyanogen;
cyanogen fluoride;
cyanogen chloride (CK);
cyanogen bromide;
cyanogen iodide; and
cyanogen azide.

17. A method of detecting a fluorine-containing compound comprising the steps of:
a) exposing a detector according to claim 1 to a sample which may or may not contain a fluorine-containing compound;
b) identifying the presence or absence of a detectable change in the detector;
c) correlating the presence of the detectable change in the detector with the presence of a fluorine-containing compound; and
d) providing an output to indicate the presence of a fluorine-containing compound.

18. A method of detecting a cyanide-containing compound comprising the steps of:
a) exposing a detector according to claim 8 to a sample which may or may not contain a fluorine-containing compound and/or a cyanide-containing compound;
b) identifying the presence or absence of a detectable change in the first organometallic compound;
c) identifying the presence or absence of a detectable change in the second organometallic compound;

d) correlating the presence of the detectable change in the first organometallic compound and the absence of the detectable change in the second organometallic compound with the presence of a cyanide containing compound; and
e) providing an output to indicate the presence of a cyanide containing compound.

\* \* \* \* \*